US011921120B2

(12) United States Patent
Rawls et al.

(10) Patent No.: US 11,921,120 B2
(45) Date of Patent: Mar. 5, 2024

(54) COMPOSITIONS AND METHODS FOR IDENTIFYING AND MODULATING METABOLIC HEALTH

(71) Applicant: Duke University, Durham, NC (US)

(72) Inventors: John F. Rawls, Chapel Hill, NC (US); James E. N. Minchin, Chapel Hill, NC (US)

(73) Assignee: Duke University, Durham, NC (US)

(*) Notice: Subject to any disclaimer, the term of this patent is extended or adjusted under 35 U.S.C. 154(b) by 306 days.

(21) Appl. No.: 17/200,886

(22) Filed: Mar. 14, 2021

(65) Prior Publication Data

US 2021/0278419 A1 Sep. 9, 2021

Related U.S. Application Data

(62) Division of application No. 15/558,889, filed as application No. PCT/US2016/022958 on Mar. 17, 2016.

(60) Provisional application No. 62/134,161, filed on Mar. 17, 2015.

(51) Int. Cl.
| | |
|---|---|
| G01N 33/68 | (2006.01) |
| A61K 38/26 | (2006.01) |
| A61K 38/28 | (2006.01) |
| A61K 39/395 | (2006.01) |
| A61K 45/06 | (2006.01) |

(52) U.S. Cl.
CPC ......... *G01N 33/6893* (2013.01); *A61K 38/26* (2013.01); *A61K 38/28* (2013.01); *A61K 39/39541* (2013.01); *A61K 45/06* (2013.01); *G01N 2800/042* (2013.01)

(58) Field of Classification Search
CPC ......... G01N 33/6893; G01N 2800/042; A61K 38/26; A61K 38/28; A61K 39/39541; A61K 45/06
See application file for complete search history.

(56) References Cited

U.S. PATENT DOCUMENTS

2006/0182825 A1* 8/2006 Prasad ............... A61K 31/16
514/625

FOREIGN PATENT DOCUMENTS

WO WO-2008054200 A2 * 5/2008 ........... A23C 9/1526
WO 2014107484 A1 7/2014

OTHER PUBLICATIONS

Sabaliauskas N.A., et al., "High-Throughput Zebrafish Histology," Methods, 2006, vol. 39(3), pp. 1246-1254.

Sakurai A., et al., "Semaphorin 3E Initiates Antiangiogenic Signaling Through Plex D1 by Regulating Arf6 and R-Ras," Molecular and Cellular Biology, 2010, vol. 30(12), pp. 3086-3098.

Salans L.B., et al., "The Role of Adipose Cell Size and Adipose Tissue Insulin Sensitivity in the Carbohydrate Intolerance of Human Obesity," Journal of Clinical Investigation, 1968, vol. 47(1), pp. 153-165.

Semova I., et al., "Microbiota Regulate Intestinal Absorption and Metabolism of Fatty Acids in the Zebrafish," Cell Host & Microbe, 2012, vol. 12(3), pp. 277-288.

Shungin et al., "New Genetic Loci Link Adipose and Insulin Biology to Body Fat Distribution," Nature, 2015, vol. 518 (7538), pp. 187-196.

Snijder MB., et al., "What Aspects of Body Fat are Particularly Hazardous and How do We Measure Them?," International Journal of Epidemiology, 2006, vol. 35(1), pp. 83-92.

Spencer M., et al., "Adipose Tissue Extracellular Matrix and Vascular Abnormalities of Obesity and Insulin Resistance," The Journal of Clinical Endocrinology and Metabolism, 2011, vol. 96(12), E1990-E1998.

Strimbu K., "What are Biomarkers?," Curr Opin HIV AIDS, 2010, vol. 5(6), pp. 463-466.

Sun K., et al., "Adipose Tissue Remodeling and Obesity," The Journal of Clinical Investigation, 2011, vol. 121(6), pp. 2094-2101.

Sun M., et al., "Collagen V is a Dominant Regulator of Collagent Fibrillogenesis: Dysfunctional Regulation of Structure and Function in a Corneal-Stroma-Specific col5a1-Null Mouse Model," Journal of Cell Science, 2011, vol. 124, pp. 4096-4105.

Tingaud-Sequiera A., et al., "Zebrafish Obesogenic Test: a Tool for Screening Molecules that Target Adiposity, "Journal of Lipid Research, 2011, vol. 52(9), pp. 1765-1772.

Torres-Vazquez J., et al., "Semaphorin-Plexin Signaling Guides Patterning of the Developing Vasculature," Developmental Cell, 2004, vol. 7(1 ), pp. 117-123.

Tuomi T., "Type 1 and Type 2 Diabetes: What Do they Have in Common?," Diabetes, 2005 , vol. 54, Issue 2, pp. S40-S45.

Uriel S., et al., "Extraction and Assembly of Tissue-Derived Gels for Cell Culture and Tissue Engineering, " Tissue Engineering: Part C, 2009, vol. 15(3), pp. 309-321.

Van Der Sar A.M., et al., "A Star with Stripes: Zebrafish as an Infection Model," Trends In Microbiology, 2004, vol. 12(10), pp. 451-457.

Walters J.W., et al., "Visualization of Lipid Metabolism in the Zebrafish Intestine Reveals a Relationship between NPC1L1-Mediated Cholesterol Uptake and Dietary Fatty Acid," Chemistry & Biology, 2012, vol. 19(7), pp. 913-925.

Wenstrup R.J., et al., "Regulation of Collagen Fibril Nucleation and Intial Fibril Assembly Involves Coordinate Interactions with Collagens V and XI in Developing Tendon," The Journal of Biological Chemistry, 2011, vol. 286(23), pp. 20455-20465.

Wood G.C., et al., "The Formation of Fibrils from Collagen Solutions," The Biochemical Journal, 1960, vol. 75, pp. 588-598.

Written Opinion for International Application No. PCT/US2016/022958 dated Aug. 15, 2016 (6 pages).

(Continued)

*Primary Examiner* — Changhwa J Cheu
(74) *Attorney, Agent, or Firm* — POLSINELLI PC

(57) ABSTRACT

This invention provides reagents, methods and biochemical markers for identifying and providing therapeutic intervention for individuals with metabolic dysfunction, or individuals at risk for metabolic dysfunction.

12 Claims, 44 Drawing Sheets

Specification includes a Sequence Listing.

(56) References Cited

OTHER PUBLICATIONS

Ahima R.S., et al., "The Health Rish of Obesity—Better Metrics Imperative," Science, 2013, vol. 341(6148), pp. 856-858.
Arner E., et al., "Adipose Tissue MicroRNAs as Regulators of CCL2 Production in Human Obesity," Diabetes, 2012, vol. 61(8), pp. 1986-1993.
Arner E., et al., "Health and Obesity: Not Just Skin Deep," Science, 2013, vol. 342(6158), pp. 558-559.
Bouraoui L., et al., "Regulation of Proliferation and Differentiation of Adipocyte Precursor Cells in Rainbow Trout (*Oncorhynchus mykiss*)," The Journal of Endocrinology, 2008, vol. 198(3), pp. 459-469.
Capiotti K.M., et al., "Persistent Impaired Glucose Metabolism in a Zebrafish Hyperglycemia Model," Comparative Biochemistry and Physiology, Part B, 2014, vol. 171, pp. 58-65.
Cardona A., et al., "An Integrated Micro-and Macro Architectural Analysis of the *Drosophila* Brain by Computer-Assisted Serial Section Electron Microscopy," PLoS Biology, 2010, vol. 8(10), e1000502.
Cardona A., et al., "TrakEM2 Software for Neural Circuit Reconstruction," PloS One, 2012, vol. 7(6), e38011.
Carten J.D., et al., "Visualizing Digestive Organ Morphology and Function Using Differential Fatty Acid Metabolism in Live Zebrafish," Developmental Biology, 2011, vol. 360(2), pp. 276-285.
Chi N.C., et al., "Foxn4 Directly Regulates tbx2b Expression and Atrioventricular Canal Formation," Genes Development, 2008, vol. 22(6), pp. 734-739.
Childs S., et al., "Patterning of Angiogenesis in the Zebrafish Embryo," Developmental, 2002, vol. 129(4), pp. 973-982.
Dahlman I., et al., "Alpha2-Heremans-Schmid Glycoprotein Gene Polymorphisms are Associated with Adipocyte Insulin Action," Diabetologia, 2004, vol. 47(11), pp. 1974-1979.
Dahlman I., et al., "Downregulation of Electron Transport Chain Genes in Visceral Adipose Tissue in Type 2 Diabetes Independent of Obesity and Possibly Involving Tumor Necrosis Factor-alpha," Diabetes, 2006, vol. 55(6), pp. 1792-1799.
Eames S.C., et al., "Blood Sugar Measurement in Zebrafish Reveals Dynamics of Glucose Homeostasis," Zebrafish, 2010, vol. 7(2), pp. 205-213.
Flynn E.J., et al., "Ontogeny and Nutritional Control of Adipogenesis in Zebrafish (*Danio rerio*)," Journal of Lipid research, 2009, vol. 50(8), pp. 1641-1652.
Folch J., et al., "A Simple Methods for the Isolation and Purification of Total Lipids from Animal Tissues," Journal of Biological Chemistry, 1957, vol. 226, pp. 497-509.
Gay C.M., et al., "Diverse Functions for the Semaphorin Receptor PlexinDI in Development and Disease," Developmental Biology, 2011, vol. 349(1), pp. 1-19.
Gharib H., "American Association of Clinical Endocrinologists Medical Guidelines for Clinical Practice for Growth Hormone Use in Adults and Children—2003 Update," Endocrine Practice, 2003, vol. 9(1), pp. 64-76.
Gitler A.D., et al., "PlexinDI and Semaphorin Signaling are Required in Endothelial Cells for Cardovascular Development," Developmental Cell, 2004, vol. 7(1), pp. 107-116.
Gokmen-Polar Y., et al., "Elevated Protein Kinase C Betall is an Early Promotive Event In Colon Carcinogenesis," Cancer Research, Feb. 2001, vol. 61 (4), pp. 1375-1381.
Goodyear L.J., et al., "Insulin Receptor Phosphorylation, Insulin Receptor Substrate-1 Phosphorylation, and Phosphatidylinositol 3-Kinase Activity are Decreased in Intact Skeletal Muscle Strips from Obese Subjects," The Journal of Clinical Investigation, 1995, vol. 95(5), pp. 2195-2204.
Hageman R.S., et al., "High-Fat Diet Leads to Tissue-Specific Changes Reflecting Risk Factors for Diseases in DRA/2J Mice," Physiological Genomics, 2010, vol. 42, No. 1, pp. 55-66.
Haynes P.A., et al., "Proteome Analysis: Biological Assay or Data Archive?," Electrophoresis, 1998, vol. 19(11), pp. 1862-1871.
Hoffstedt J., et al., "Regional Impact of Adipose Tissue Morphology On the Metabolic Profile In Morbid Obesity," Diabetologia, 2010, vol. 53(12), pp. 2496-2503.
Iannuccelli E., et al., "NEMO: a Tool for Analyzing Gene and Chromosome Territory Distributions from 3D-FISH Experiments," Bioinformatics, 2010, vol. 26(5), pp. 696-697.
Imrie D., et al., "White Adipose Tissue Development in Zebrafish is Regulated by Both Developmental Time and Fish Size," Developmental Dynamics, 2010, vol. 239(11), pp. 3013-3023.
International Preliminary Report on Patentability for International Application No. PCT/US2016/022958, dated Sep. 28, 2017 (8 pages).
International Search Report for International Application No. PCT/US2016/022958 dated Aug. 15, 2016 (4 pages).
Ippei., et al., "Semaphorin-induced inflammation contributes to insulin resistance in dietary obesity," Circulation, 2012, vol. 126, Suppl. Symposium (Abstract).
Jin et al., "Cellular and Molecular Analyses of Vascular Tube and Lumen Formation in Zebrafish," Development, 2005, vol. 132(23), pp. 5199-5209.
Jun et al., "Taking Aim at the Extracellular Matrix: CNN Proteins as Semerging Therapeutic Targets," Nature Revies Drug Discovery, 2011, vol. 10, pp. 945-963.
Kanther M., et al., "Microbial Colonization Induces Dynamic Temporal and Spatial Patterns of NF-[kappa]B Activation in the Zebrafish Digestive Tract," Gastroenterology, 2011, vol. 141(1), pp. 197-207.
Kavanaugh A., "Biomarkers in Rheumatology: Promise and Pitfalls," Future Rheumatol, 2008, vol. 3(4), pp. 303-305.
Kim et al., "Obesity-Associated Improvements in Metabolic Profile through Expansion of Adipose Tissue," The Journal of Clinical Investigation, 2007, vol. 117(9), pp. 2621-2637.
Konopka J.B., et al., "Variable Expression of the Translocated C-abl Oncogene in Philadelphia-Chromosome-Positive B-Lymphoid Cell Lines from Chronic Myelogenous Leukemia Patients," Proceedings of the National Academy of Sciences of the United States of America, 1986, vol. 83(11), pp. 4049-4052.
Kushminski C.M., et al., "MitoNEET-Driven Alterations in Adipocyte Mitochondrial Activity Reveal a Crucial Adaptive Process that Preserves Insulin Sensitivity in Obesity," Nature Medicine, 2012, vol. 18(10), pp. 1539-1549.
Lackey D.E., et al., "Contributions of Adipose Tissue Architectural and Tensile Properties Toward Defining Healthy and Unhealthy Obesity," American Journal of Physiology Endocrinology and Metabolism, 2014, vol. 306(3), pp. E233-E246.
Lawson N.D., et al., "In Vivo Imaging of Embryonic Vascular Development Using Transgenic Zebrafish," Developemental Biology, 2002, vol. 248(2), pp. 307-318.
Marchant J.K., et al., "Reduction of Type V Collagen Using a Dominant-Negative Strategy Alters the Regulation of Fibrillogenesis and Results in the Loss of Corneal-Specific Fibril Morphology," The Journal of Cell Biology, 1996, vol. 135(5), pp. 1415-1426.
Mariman E.C.M., et al., "Adipocyte Extracellular Matrix Compostion, Dynamics and Role in Obesity," Cellular and Molecular Life Sciences, 2010, vol. 67(8), pp. 1277-1292.
Marza E., et al., "Developmental Expression and Nutritional Regulation of a Zebrafish Gene Homologous to Mammalian Microsomal Triglyceride Transfer Protein Large Subunit," Developmental Dynamics, 2004, vol. 232(2), pp. 506-518.
Mayeux R., "Biomarkers: Potential Uses and Limitations," NeuroRx, 2004, vol. 1(2), pp. 182-188.
Mcmenamin S.K., et al., "Dwarfism and Increased Adiposity in the gh1 Mutant Zebrafish Vizzini," Endocrinology, 2013, vol. 154(4), pp. 1476-1478.
Minchin J.E.N., et al., "In Vivo Analysis of White Adipose Tissue in Zebrafish," Methods in Cell Biology, 2011, vol. 105, pp. 63-86.
Nakajima I., et al., "Extracellular Matrix Development During Differentiation into Adipocytes with a Unique Increase in Type V and VI Collagen," Biology of the cell, 2002, vol. 94(3), pp. 197-203.

(56) References Cited

OTHER PUBLICATIONS

Nakajima I., et al., "Positive Effect of Collagen V and VI on Triglyceride Accumulation During Differentiation in Cultures of Bovine Intramuscular Adipocytes," Differentiation, 2002, vol. 70, pp. 84-91.

Parichy D.M., et al., "Normal Table of Post-Embryonic Zebrafish Development Staging be Externally Visible Anatomy of the Living Fish," Developmental Dynamics, 2009, vol. 238(12), pp. 2975-3015.

Rawls J.F., et al., "In Vivo Imaging and Genetic Analysis Link Bacterial Motility and Symbiosis in the Zebrafish Gut," PNAS, 2007, vol. 104(18), pp. 7622-7627.

Romano N., et al., "Distribution of Macrophages During Fish Development an Immunohistochemical Study in Carp (*Cyprinus carpio*, L.), " Anatomy and Embroyology, 1998, vol. 198(1), pp. 31-41.

Ruiz-Alcaraz A.J., et al., "A Novel Regulation of IRS1 (insulin receptor substrate-1) Expression Following Short Term Insulin Administration," The Biochemical Journal, 2005, vol. 392, pp. 345-352.

Ryden M., et al., "Comparative Studies of the Role of Hormone-Sensitive Lipase and Adipose Triglyceride Lipase in Human Fat Cell Lipolysis," American Journal of Physiology Enocrinology and Metabolism, 2007, vol. 292(6), pp. E1847-E1855.

\* cited by examiner

| Group | N | μ2 | μ3 |
|---|---|---|---|
| sibling + ctrl vMO | 7 | 75.98 | — |
| sibling + col5a1 vMO | 6 | 78.93 | — |
| plxnd1 + ctrl vMO | 8 | 61.17 | — |
| plxnd1 + col5a1 vMO | 12 | 72.97 | 122.59 |

FIG. 2E

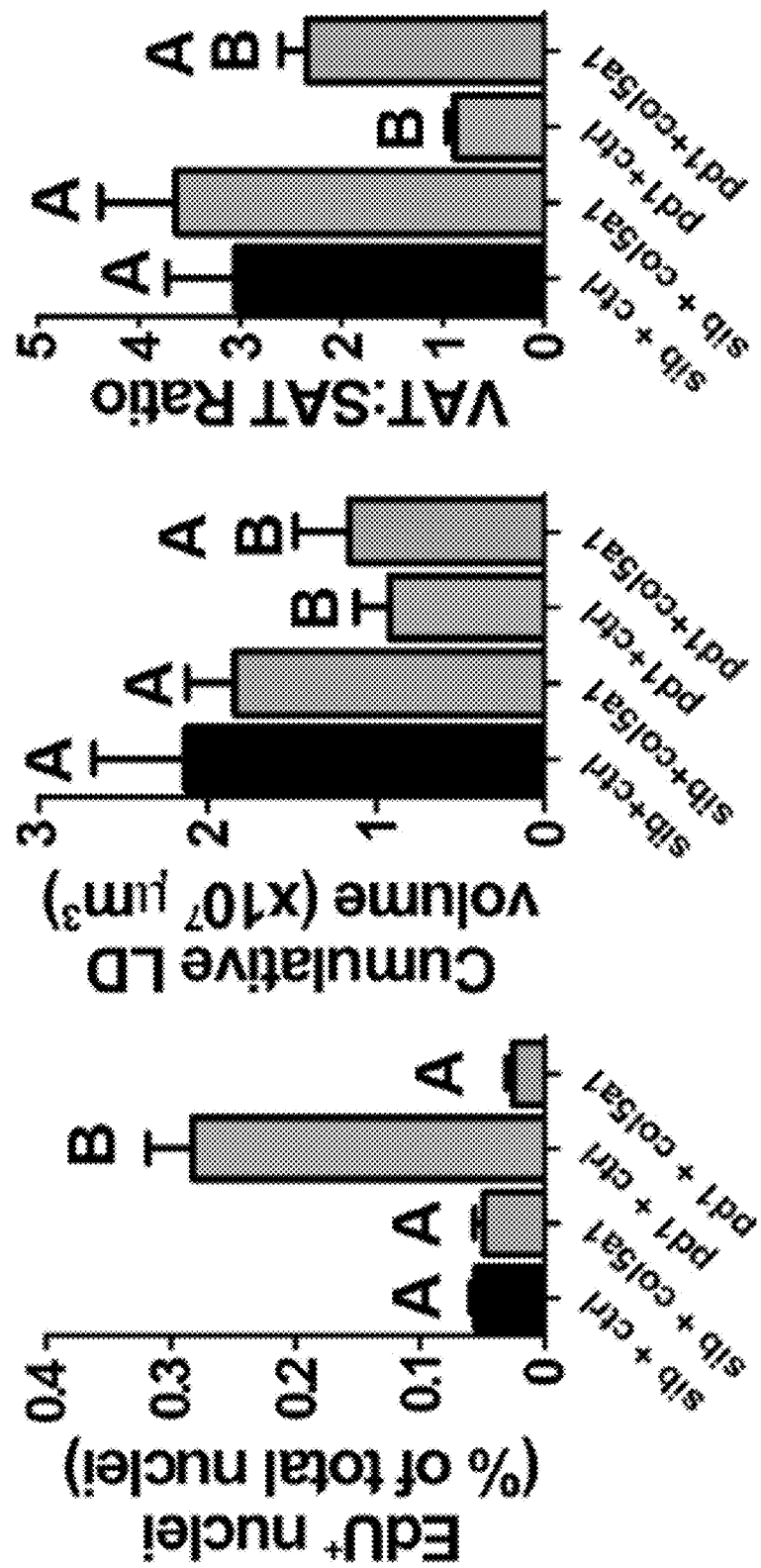

| Genotype | Diet | N | μ1 | μ2 |
|---|---|---|---|---|
| *plxnd1/+* | control | 11 | 9.16 μm | 74.23 μm |
| *plxnd1/+* | high fat | 11 | 9.74 μm | 156.69 μm |
| *plxnd1* | control | 12 | 9.79 μm | 57.09 μm |
| *plxnd1* | high fat | 12 | 13.73 μm | 82.29 μm |

FIG. 4C

| Genotype | Diet | N | μ1 |
|---|---|---|---|
| *plxnd1/+* | control | 11 | 67.71 μm |
| *plxnd1/+* | high fat | 11 | 86.54 μm |
| *plxnd1* | control | 12 | 52.99 μm |
| *plxnd1* | high fat | 12 | 98.48 μm |

FIG. 4D

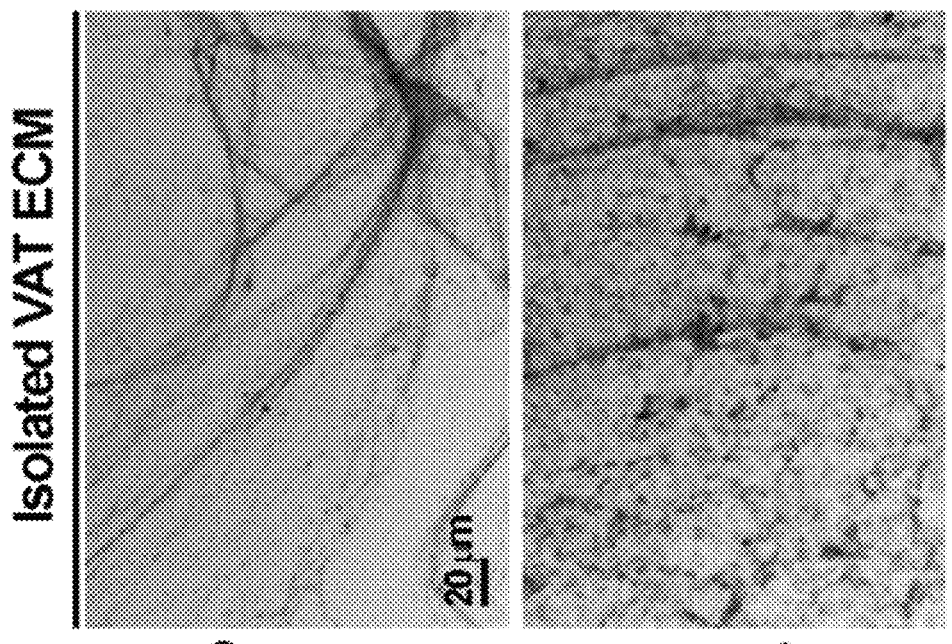
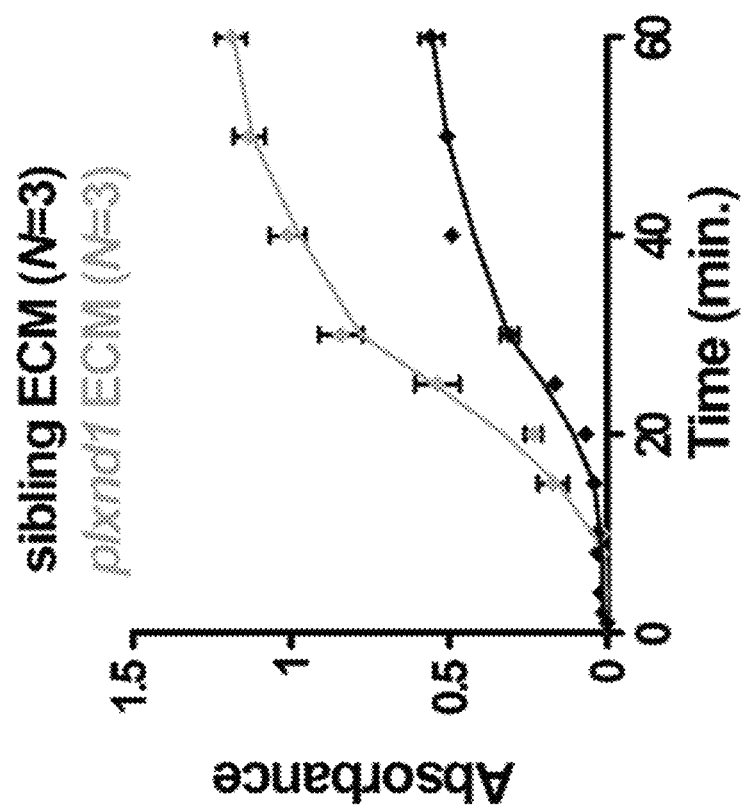
FIG. 13C
FIG. 13B

SEQUENCE LISTING

```
<160> NUMBER OF SEQ ID NOS: 57

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
catcacgcat cgctaaagag                                                   20

<210> SEQ ID NO 2
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 2
gctctcagat tcccttcttt gtc                                               23

<210> SEQ ID NO 3
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 3
gagagcaaca tgttcctgat tggaatgct                                         29

<210> SEQ ID NO 4
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 4
tctgaggtcc ggcttgcagt gaattgg                                           27

<210> SEQ ID NO 5
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 5
ggctttaaga ctggcggttg ttgtaa                                            26
```

<210> SEQ ID NO 6
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 6
ttaagatgag gtgcaaaggt cacgg                                    25

<210> SEQ ID NO 7
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 7
atattcagag cagagtaaat cag                                      23

<210> SEQ ID NO 8
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 8
gggtgcagat gagcgcagtt c                                        21

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
caacatgccc cctcaccact                                          20

<210> SEQ ID NO 10
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 10
cgacacacat gttgttgtg                                           19

<210> SEQ ID NO 11
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 11
gactgattac tatcgcaagg g                                        21

<210> SEQ ID NO 12
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 12
tccaggtatc ctccgtccat                                            20

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
agaaccccaa actgatgctg                                            20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
atctgctgtt tgatggcaca                                            20

<210> SEQ ID NO 15
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 15
cacttgtccc tctaagaagt tgca                                       24

<210> SEQ ID NO 16
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 16
ggttgattcc gataacgaac ga                                         22

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
ggcaaacttg tgcagaaaca                                            20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 18
gaactgagcc tggcatcttc                                            20

```
<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
atcagcgcct acattgatcc                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
ttgcttggct gtcgtagatg                                               20

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 21
ctgaggggaa caagagcaag                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 22
agtctggtac ggcaggtacg                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
tgccgcatac acaagaagag                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 24
atgtggttca cgtcactgga                                               20

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 25
accaggcagt ccagaacatc                                          20

<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26
ggtttccatt ctcagcatcc                                          20

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 27
gaacttcctc aggctgctgt                                          20

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 28
tgtaagccac gctgttcttg                                          20

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 29
caggaaggcc aggactacaa                                          20

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
cgttcacctg gaaatcctct                                          20

<210> SEQ ID NO 31
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 31
caccctatgc cttatcagtc ttc                                      23

<210> SEQ ID NO 32
<211> LENGTH: 22

-continued

```
<212> TYPE: DNA
<213> ORGANISM: Artificial Sequence
<220> FEATURE:
<223> OTHER INFORMATION: Synthetic Oligonucleotide

<400> SEQUENCE: 32
tgtttcattt gctcaatctc ca                                              22

<210> SEQ ID NO 33
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 33
tacacgtggt caaggaa                                                    17

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
tcccctcaca ccagtaggtc                                                 20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
agggtaaaca tggtccagca                                                 20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
accgattgca ccactttctc                                                 20

<210> SEQ ID NO 37
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 37
gattactgcc acacccacat tc                                              22

<210> SEQ ID NO 38
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 38
```
tcctcaaact cctcctccac a                                              21

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
gatgtgtgct gctcctttga                                                20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
gccccaaagt ctccttttc                                                 20

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
ggagggatcc tgtctgactg                                                20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 42
ttgctacctt gagccttgct                                                20

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 43
gaccaaacca gcctgacaat                                                20

<210> SEQ ID NO 44
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 44
tgcatgtaaa aggcagatgg                                                20

<210> SEQ ID NO 45
<211> LENGTH: 20
<212> TYPE: DNA
<213> ORGANISM: Artificial Sequence

```
<220> FEATURE:
<223> OTHER INFORMATION: Synthetic Oligonucleotide

<400> SEQUENCE: 45
atgcttccgc agatcttcat                                                   20

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 46
accgtcatga gctcgtctct                                                   20

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 47
gcatgtttcg actggtcaac                                                   20

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
cctgctgaca cactccatgt                                                   20

<210> SEQ ID NO 49
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 49
aagaggagcc agctgttgaa                                                   20

<210> SEQ ID NO 50
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 50
atggtttagg cagggttct                                                    20

<210> SEQ ID NO 51
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 51
tttcccagag atgggttgtg                                                   20
```

-continued

```
<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52
aggaacgact gactgccttt                                               20

<210> SEQ ID NO 53
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 53
cagacggtgt aacgaaacta cag                                           23

<210> SEQ ID NO 54
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 54
gggtgcagaa acctcacagt                                               20

<210> SEQ ID NO 55
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(25)
<223> OTHER INFORMATION: Morpholino (standard nucleic acid bases bound
      to morpholine rings)

<400> SEQUENCE: 55
gaaacatgga tgctacagag agaga                                         25

<210> SEQ ID NO 56
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(25)
<223> OTHER INFORMATION: Morpholino (standard nucleic acid bases bound
      to morpholine rings)

<400> SEQUENCE: 56
gagttcctac ttacctcaaa cacct                                         25

<210> SEQ ID NO 57
<211> LENGTH: 25
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
```

-continued

```
<222> LOCATION: (1)..(25)
<223> OTHER INFORMATION: Morpholino (standard nucleic acid bases bound
      to morpholine rings)

<400> SEQUENCE: 57
cctcttacct cagttacaat ttata                                              25
```

COMPOSITIONS AND METHODS FOR IDENTIFYING AND MODULATING METABOLIC HEALTH

CROSS-REFERENCE TO RELATED APPLICATIONS

This application is a division of U.S. patent application Ser. No. 15/558,889, filed Sep. 15, 2017, which is a U.S. national phase application of International Patent Application No. PCT/US2016/022958, filed Mar. 17, 2016, which claims the benefit of U.S. provisional application No. 62/134,161, filed Mar. 17, 2015, all of which are incorporated herein by reference in their entirety.

STATEMENT REGARDING FEDERALLY SPONSORED RESEARCH OR DEVELOPMENT

This invention was made with government support under R56 DK 091356-01 awarded by the National Institutes of Health. The government has certain rights in the invention.

INCORPORATION BY REFERENCE OF SEQUENCE LISTING PROVIDED ELECTRONICALLY

This application contains a Sequence Listing submitted as an electronic .txt file named "16_275_WO_US_DIV_2021_03_14_Sequence_Listing", having a size of 11 KB and created on 14 Mar. 2021. The information contained in this electronic .txt file is incorporated herein by reference in its entirety.

BACKGROUND OF THE INVENTION

Field of the Invention

This disclosure provides reagents, methods and biochemical markers for identifying and treating individuals with metabolic dysfunction, and for determining efficacy of a therapeutic intervention to correct metabolic dysfunction. Specifically, embodiments of the present disclosure relate to novel methods of identifying and treating metabolic disease mediated by PLEXIN D1 (PLXND1) and COLLAGEN5A1 (COL5A1), wherein the distribution and morphology of adipose tissue (AT) is disrupted relative to normal, healthy individuals.

Description of Related Art

Adipose Tissue Distribution and Morphology

The regional distribution and morphology of AT are strong predictors of metabolic disease (Salans L B, Knittle J L, & Hirsch J (1968), The Journal of clinical investigation 47(1):153-165; Ahima R S & Lazar M A (2013), Science 341(6148):856-858; Amer E & Amer P (2013), Science 342(6158):558-559.) Excess lipid deposition in visceral adipose tissue (VAT) (adipose associated with visceral organs) is associated with increased susceptibility to insulin resistance and type 2 diabetes (Hoffstedt J, et al. (2010), Diabetologia 53(12):2496-2503) whereas expansion of subcutaneous adipose tissue (SAT) (adipose between muscle and skin) is associated with reduced risk of metabolic disease and is even protective against hyperglycemia and dyslipidemia. (Id.; Fox C S, et al. (2007), Circulation 116(1):39-48; Snijder M B, van Dam R M, Visser M, & Seidell J C (2006), International journal of epidemiology 35(1):83-92; Kim J Y, et al. (2007), The Journal of clinical investigation 117(9):2621-2637.)

In turn, hypertrophic AT morphology (few large adipocytes) is associated with insulin resistance and AT dysfunction; whereas hyperplastic AT morphology (many small adipocytes) is associated with improved metabolic parameters. (Id.; Sun K, Kusminski C M, & Scherer P E (2011), The Journal of clinical investigation 121(6):2094-2101; Kusminski C M, et al. (2012), Nature medicine 18(10): 1539-1549.)

PLEXIN D1 Association with Metabolic Disease

Genome-wide association studies have implicated the PLEXIN D1 (PLXND1) gene as one of dozens of genes whose expression pattern are associated with body fat distribution and type 2 diabetes in humans. (Shungin D, et al. (2015), Nature 518(7538):187-196.)

Prior to the present disclosure, whether or how Plxnd1 plays a direct, causal role in AT morphology, distribution, and metabolism is unknown.

Plxnd1 is a transmembrane receptor that controls the migration, proliferation and survival of diverse cell types. (Gay C M, Zygmunt T, & Torres-Vazquez J (2011), Developmental biology 349(1):1-19.) Mutation of Plxnd1 in mouse and zebrafish leads to hypervascularization in many tissues. (Gitler A D, Lu M M, & Epstein J A (2004), Developmental cell 7(1):107-116; Torres-Vazquez J, et al. (2004), Developmental cell 7(1):117-123.) Vascular endothelial cell Plxnd1 modulates extracellular matrix (ECM) synthesis and composition by regulating the collagen receptor, β1-Integrin. (Sakurai A, et al. (2010), Molecular and cellular biology 30(12):3086-3098.) In turn, ECM provides a supportive microenvironment for AT growth and function. (Mariman E C & Wang P (2010), Cellular and molecular life sciences: CMLS 67(8): 1277-1292.)

Type V Collagens and ECM Dynamics During Adipogenesis

Type V collagens are ECM proteins that regulate collagen fiber assembly, geometry and strength. (Wenstrup R J, et al. (2011), The Journal of biological chemistry 286(23):20455-20465; Sun M, et al. (2011), Journal of cell science 124(Pt 23):4096-4105.). In addition, type V collagens are upregulated during adipogenesis and can stimulate adipocyte differentiation in vitro. Spencer M, et al. (2011), The Journal of clinical endocrinology and metabolism 96(12):E1990-1998; Nakajima I, Muroya S, Tanabe R, & Chikuni K (2002), Differentiation; research in biological diversity 70(2-3):84-91; Nakajima I, Muroya S, Tanabe R, & Chikuni K (2002), Biology of the cell 94(3):197-203.)

Prior to the present disclosure, whether or how type V collagens mediate metabolic health through a role in AT morphology, distribution, and metabolism was unknown.

Therefore, there is a need in the art to identify factors that regulate AT distribution and morphology, and that comprise molecular targets for identifying and treating subjects with metabolic dysfunction. In addition, there is a need in the art to determine whether and how the PLXND1 gene exerts control over AT distribution, morphology, and metabolism, and by extension metabolic health. Similarly, there is a need in the art to identify whether and how type V collagens exert control over AT distribution, morphology, and metabolism, and by extension metabolic health. Still further, there is a need to develop clinical methods to identify and treat metabolic diseases characterized by abnormal or dysfunctional AT distribution and morphology.

SUMMARY OF THE INVENTION

Against this backdrop, embodiments of the present disclosure address one or more of the above-identified needs, among others, recognized by those skilled in the art, and provide several benefits over existing clinical methods of identification and therapeutic intervention in subjects with metabolic dysfunction.

In embodiments, the invention disclosed herein provides methods for treating a subject (i.e. providing a "therapeutic treatment") for subjects, or patients, with metabolic dysfunction. In embodiments, methods of treatment are provided for subjects suffering from, or suspected to suffer from, or with a propensity toward, metabolic dysfunction. In certain embodiments, the disclosure provides methods for preventing metabolic dysfunction in a subject. In still further embodiments, the disclosure provides methods for treating or preventing metabolic dysfunction in combination with other therapies.

In some embodiments, the disclosure provides methods of treating or preventing metabolic dysfunction, where such metabolic dysfunction is based on, or characterized by, changes in the ratio of Visceral Adipose Tissue (VAT) to Subcutaneous Adipose Tissue (SAT). In further embodiments, the disclosure provides therapeutic treatment in subjects with metabolic dysfunction based on changes in the prevalence of hypertrophic AT morphology (i.e., AT morphology characterized by being comprised of relatively few large adipocytes) and hyperplastic AT morphology (i.e., AT morphology characterized by being comprised of many small adipocytes).

In still further embodiments, the disclosure provides methods of treating or preventing metabolic dysfunction, including, but not limited to or mutually exclusive with, diabetes mellitus type II; impaired glucose tolerance or insulin resistance; high blood pressure; central obesity and difficulty losing weight; high cholesterol; combined hyperlipidemia; including elevated LDL; decreased HDL; elevated triglycerides; and fatty liver (especially in concurrent obesity).

In embodiments, the disclosure provides methods for treating a subject with metabolic dysfunction, including insulin resistance and/or related conditions, in a subject in need thereof, the method comprising the step of decreasing the level or activity of the Plxnd1 gene, or products of the Plxnd1 gene. The level of the Plxnd1 gene, or products of the Plxnd1 gene, may be decreased by methods disclosed in the various embodiments.

In further embodiments, disclosure pertains to a method for preventing and/or treating metabolic dysfunction, including insulin resistance and/or related conditions, in a subject in need thereof, the method comprising the step of decreasing the level or activity of one or more genes, or their products, selected from collagen, type I, alpha 2 (COL1A2 in human, col1a2 in zebrafish); collagen, type II, alpha 1 (COL2A1 in human, col2a1a col2a1b in zebrafish); collagen, type IV, alpha 1 (COL4A1 in human, col4a1 in zebrafish); collagen, type V, alpha 2 (COL5A2 in human, col5a2a col5a2b in zebrafish); collagen, type V, alpha 3 (COL5A3 in humans, col5a3a col5a3b in zebrafish); collagen, type VI, alpha 1 (COL6A1 in human, col6a1 in zebrafish); fibronectin 1 (FN1 in human, fn1a/fn1b in zebrafish); aggrecan (ACAN in human, acana/acanb in zebrafish); laminin, alpha 1 (LAMA1 in human, lama1 in zebrafish); glypican 4 (GPC4 in human, gpc4 in zebrafish); and secreted protein, acidic, cysteine-rich (osteonectin) (SPARC in human, sparc in zebrafish). The level of the one or more genes, or products of the one or more genes, may be decreased by methods disclosed in the various embodiments herein.

In still further embodiments, this disclosure pertains to a method for preventing and/or treating metabolic dysfunction, including insulin resistance and/or related conditions, in a subject in need thereof, the method comprising the step of increasing the level or activity of the COL5A1 gene, or products of the COL5A1 gene. The level of the COL5A1 gene, or products of the COL5A1, may be increased by methods disclosed in the various embodiments.

In embodiments, the invention disclosed herein provides methods for identifying a subject with metabolic dysfunction. In embodiments, metabolic dysfunction identified in a subject according to the present methods is based on changes in the ratio of Visceral Adipose Tissue (VAT) to Subcutaneous Adipose Tissue (SAT). In some embodiments, the disclosure further provides methods for identifying a subject with metabolic dysfunction based on changes in the prevalence of hypertrophic AT morphology (i.e., AT morphology characterized by being comprised of relatively few large adipocytes) and hyperplastic AT morphology (i.e., AT morphology characterized by being comprised of many small adipocytes).

The disclosure also provides methods for predicting whether a subject is suffering from a metabolic dysfunction, or is at elevated risk for metabolic dysfunction. In these embodiments, the methods comprise the steps of: (a) isolating a biosample from a subject; (b) determining a level or concentration of one or more biomarkers present in the biosample; and (c) identifying the subject as suffering from a metabolic dysfunction, or is at elevated risk for metabolic dysfunction, when the level or concentration of one or more biomarkers is increased or decreased relative to a control level or range.

The disclosure also provides methods for identifying a subject that is eligible for reimbursement of an insurance claim for treatment of metabolic dysfunction. In these embodiments, the methods comprise the steps of: (a) isolating a biosample from a subject; (b) determining a level or concentration of one or more biomarkers present in the biosample; and (c) as eligible for reimbursement of the insurance claim when the concentration of one or more biomarkers is increased or decreased relative to an insurance control value. In these embodiments, the insurance control value refers to an amount or range of amounts of a biochemical marker such as Plxnd1 and Col5a1.

The disclosure further provides methods for determining the efficacy of a treatment for metabolic dysfunction in a subject. In these embodiments, the methods comprise the steps of: (a) treating a subject for a metabolic dysfunction; (b) isolating a biosample from the subject; (c) determining a level or concentration of one or more biomarkers present in the biosample; and (d) determining the efficacy of the treatment for metabolic dysfunction when the concentration of one or more biomarkers is increased or decreased relative to a pre-treatment level or pre-treatment range of the one or more biomarkers.

Specific preferred embodiments of the present invention will become evident from the following more detailed description of certain preferred embodiments and the claims.

BRIEF DESCRIPTION OF THE DRAWINGS

The following detailed description can be best understood when read in conjunction with the following drawings in which:

FIG. 1 shows that reduced VAT volume and hyperplastic morphology underlie an altered body fat distribution in plxnd1 mutant zebrafish.

FIG. 2 shows that Col5a1 is essential for maintenance of the hyperproliferative and hyperplastic state of plxnd1 mutant VAT.

FIG. 2(E) shows means of probability density functions to represent VAT-LD diameter distributions from sibling or plxnd1 animals injected with either control or col5a1 Vivo-Morpholino (vMO). VAT-LD diameters were modelled using a mixture of 2 or 3 normal distributions. The mean 40 of each distribution is indicated ($\mu$1, $\mu$2 and $\mu$3). FIG. 2(F) shows that injection of col5a1 vMO normalizes the hyperproliferation observed in plxnd1 VAT. FIG. 2(G) shows that injection of col5a1 vMO increases VAT cumulative volume in plxnd1 mutants. FIG. 2(H) shows that injection of col5a1 vMO increases the VAT:SAT ratio in plxnd1 mutants.

FIG. 3 shows that the extracellular matrix of plxnd1 mutant VAT is sufficient to induce hyperplastic morphology in a Col5a1-dependent manner.

FIG. 4 shows that VAT fails to expand in homozygous plxnd1 mutants fed a high-fat diet, leading to disproportionately large increases in SAT.

FIG. 4(C) shows means of probability density functions of VAT LD sizes. All groups exhibited bimodal LD size distributions. FIG. 4(D) shows means of probability density functions of SAT LD sizes. All groups exhibited unimodal LD size distributions.

FIG. 5 shows that mutation of plxnd1 protects zebrafish from high-fat diet induced insulin resistance.

FIG. 6 shows plxnd1 zebrafish mutants have reduced lipid storage in VAT.

FIG. 7 shows hyperplastic VAT morphology in plxnd1 zebrafish.

FIG. 8 shows plxnd1 mutant SAT is indistinguishable from wild-type siblings.

FIG. 9 shows the experimental design and validation of col5a1 targeted Vivo-Morpholino experiments.

FIG. 11 shows plxnd1 mutant VAT has increased fibrous collagen as indicated by Masson's trichrome staining.

FIG. 12 shows altered ECM composition in plxnd1 VAT.

FIG. 13 shows Isolation and characterisation of ECM from zebrafish VAT.

FIG. 13(B) shows a turbidity assay revealing increased fibrillogenesis in plxnd1 mutant VAT. FIG. 13(C) shows maximum intensity projections of isolated VAT ECM stained with 5-DTAF from siblings and plxnd1 reveals the increased fibrous structure of plxnd1 mutant VAT ECM.

FIG. 14 shows mixing of sibling and plxnd1 ECM induces an intermediate proliferation and morphology phenotype.

FIG. 15 shows adipose quantification in plxnd1 mutants fed a high-fat diet.

FIG. 16 shows PLXND1 mRNA levels are associated with reduced Insulin-stimulated lipogenesis in SAT in humans.

FIG. 19 shows PLXND1 mRNA levels were higher in human SAT than VAT.

DETAILED DESCRIPTION OF THE INVENTION

Figure 1A:
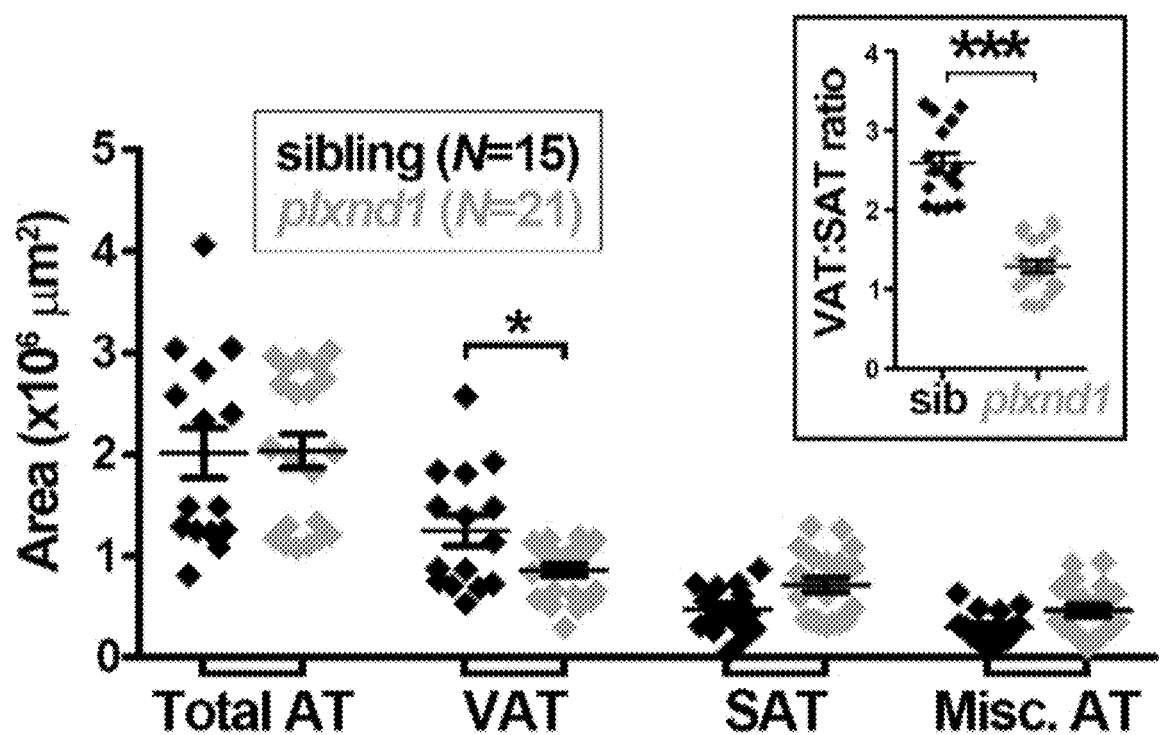
FIG. 1(A) shows VAT area is reduced in plxnd1 zebrafish (P=0.0115), leading to a decreased VAT:SAT ratio (inset, P<0.0001). There were trends towards increases in SAT (P=0.142), miscellaneous AT (P=0.053) and total adiposity (P=0.085).
Figure 1B:
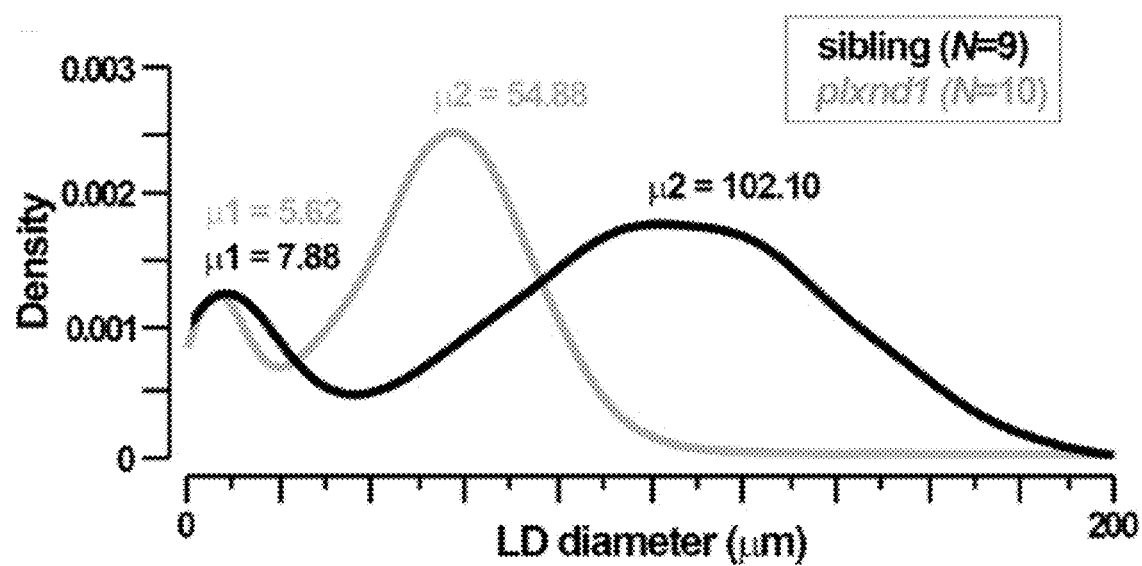
FIG. 1(B) shows probability density functions to represent VAT-LD diameter distributions. VAT-LD diameters were modelled using a mixture of 2 normal distributions. The mean ($\mu$) of each distribution is indicated ($\mu$1 and $\mu$2).

All publications, patents and patent applications cited herein are hereby expressly incorporated by reference for all purposes.

Before describing the disclosed methods and compositions in detail, a number of terms will be defined. As used herein, the singular forms "a", "an", and "the" include plural referents unless the context clearly dictates otherwise.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of this invention.

For the purposes of describing and defining this invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Provided herein are methods for identifying, preventing, or treating a subject at risk for metabolic dysfunction and its associated disorders. Metabolic dysfunction will be recognized in the art as including a spectrum of disorders. In embodiments of the present disclosure, conditions associated with metabolic dysfunction include, but are not limited to or mutually exclusive with, diabetes mellitus type II (also referred to as Type 2 diabetes, or T2D); impaired glucose tolerance or insulin resistance; high blood pressure; central obesity and difficulty losing weight; high cholesterol; combined hyperlipidemia; including elevated LDL; decreased HDL; elevated triglycerides; and fatty liver (especially in concurrent obesity).

In embodiments, the metabolic dysfunction of the present disclosure is characterized by abnormal distribution or morphology of adipose tissue (AT). In embodiments, the metabolic dysfunction of the present disclosure comprises an abnormal distribution of AT accumulating in visceral adipose tissue (VAT). In some embodiments, the metabolic dysfunction of the present disclosure comprises an abnormal distribution resulting in an elevated proportion of VAT relative to subcutaneous adipose tissue (SAT).

In still further embodiments, the metabolic dysfunction of the present disclosure comprises hypertrophic VAT morphology in effected subjects, relative to hyperplastic VAT morphology in subjects not suffering from metabolic dysfunction. As used herein, "hypertrophic AT morphology" comprises adipose tissues with a reduced number of adipocytes that are of increased size, and "hypertrophic VAT morphology" comprises visceral adipose tissues with a reduced number of adipocytes that are of increased size. As used herein, "hyperplastic AT morphology" comprises adipose tissues with an increased number of adipocytes that are of decreased size, and "hyperplastic VAT morphology" comprises visceral adipose tissues with an increased number of adipocytes that are of reduced size.

Those skilled in the art will recognize that hypertrophic morphology and hyperplastic morphology are relative terms. Thus, hypertrophic AT morphology in a subject suffering from metabolic dysfunction is optionally measured relative to normal AT morphology in a healthy subject. Similarly, hyperplastic AT morphology is optionally measured relative to the AT morphology in a subject suffering from metabolic dysfunction.

Alternatively, hyperplastic AT morphology is measured relative to the AT morphology of a normal subject, as, for example, wherein such hyperplastic morphology confers a protective or prophylactic effect on the subject.

As used herein "metabolic syndrome" refers to a patient that has a collection of indicators codified in the United States with the publication of the National Cholesterol Education Program Adult Treatment Panel III (ATP III) guidelines in 2001. Disorders associated with metabolic syndrome include elevated diabetes risk, hypertension, obesity, abnormal lipid metabolism (e.g. dyslipidemia), central adiposity, oxidative stress and its many manifestations including, stroke, ischemia, and atherosclerosis.

As used herein, the term "insulin resistance" has its common meaning in the art. Insulin resistance is a physiological condition where the natural hormone insulin becomes less effective at lowering blood sugars. The resulting increase in blood glucose may raise levels outside the normal range and cause adverse health effects such as metabolic syndrome, dyslipidemia and subsequently type 2 diabetes mellitus. The term "insulin resistance-related complications" and "insulin resistance-related conditions" as used herein encompass, without limitation, metabolic syndrome, dyslipidemia and type 2 diabetes mellitus, as well as insulin resistance in endocrine diseases (e.g., obese subjects with type 1 diabetes mellitus, Cushing's disease and lipodystrophy syndromes).

In embodiments, this disclosure pertains to a method for preventing and/or treating metabolic dysfunction, including insulin resistance and/or related conditions, in a subject in need thereof, the method comprising the step of decreasing the level or activity of the Plxnd1 gene, or products of the Plxnd1 gene. The level of the Plxnd1 gene, or products of the Plxnd1 gene, may be decreased by methods disclosed in the various embodiments.

In other embodiments, this disclosure pertains to a method for preventing and/or treating metabolic dysfunction, including insulin resistance and/or related conditions, in a subject in need thereof, the method comprising the step of decreasing the level or activity of one or more genes, or their products, selected from collagen, type I, alpha 2 (COL1A2 in human, col1a2 in zebrafish); collagen, type II, alpha 1 (COL2A1 in human, col2a1a col2a1b in zebrafish); collagen, type IV, alpha 1 (COL4A1 in human, col4a1 in zebrafish); collagen, type V, alpha 2 (COL5A2 in human, col5a2a col5a2b in zebrafish); collagen, type V, alpha 3 (COL5A3 in humans, col5a3a col5a3b in zebrafish); collagen, type VI, alpha 1 (COL6A1 in human, col6a1 in zebrafish); fibronectin 1 (FN1 in human, fn1a/fn1b in zebrafish); aggrecan (ACAN in human, acana acanb in zebrafish); laminin, alpha 1 (LAMA1 in human, lama1 in zebrafish); glypican 4 (GPC4 in human, gpc4 in zebrafish); and secreted protein, acidic, cysteine-rich (osteonectin) (SPARC in human, sparc in zebrafish). The level of the one or more genes, or products of the one or more genes, may be decreased by methods disclosed in the various embodiments herein.

In still further embodiments, this disclosure pertains to a method for preventing and/or treating metabolic dysfunction, including insulin resistance and/or related conditions, in a subject in need thereof, the method comprising the step of increasing the level or activity of the Col5a1 gene, or products of the Col5a1 gene. The level of the Col5a1 gene, or products of the Col5a1, may be increased by methods disclosed in the various embodiments.

In yet additional embodiments, this disclosure pertains to a method for preventing and/or treating metabolic dysfunction, including insulin resistance and/or related conditions, in a subject in need thereof, the method comprising the step of increasing or decreasing the level or activity of components in the intracellular pathway mediated by Plxnd1 signaling. In some embodiments, the methods of the present disclosure comprise modulating the level or activity of components upstream of Plxnd1 signaling. In embodiments, modulating the level or activity of components upstream of Plxnd1 signaling comprises modulating the genes, or gene products, of, without limitation, members of the Neuropilin or Semaphorin family of proteins.

As used herein, the term active pharmaceutical ingredient (API) means a compound or compounds with the ability to modulate metabolic dysfunction in a subject. In some embodiments, an API of present disclosure is capable of modulating the levels or activity of the Plxnd1 gene, or of products of the Plxnd1 gene. In other embodiments, an API of present disclosure is capable of modulating the levels or activity of the Col5a1 gene, or of products of the Col5a1 gene. In certain embodiments, an API of the present disclosure is capable of modulating the Plxnd1/Col5a1 pathway. In still further embodiments, an API according to the present disclosure comprises a molecule that regulates ECM components in visceral adipose tissues.

In some embodiments, an API of the present disclosure comprises an interfering molecule. As used herein, the term "interfering molecule" refers to any molecule that is capable of disrupting, or inhibiting, an intracellular signaling pathway. In preferred embodiments, the interfering molecule is capable of disrupting the signaling pathway. An interfering molecule of the invention, for example, can inhibit the activity of a protein that is encoded by a gene either directly or indirectly. Direct inhibition can be accomplished, for example, by binding to a protein and thereby preventing the protein from binding an intended target, such as a receptor. Indirect inhibition can be accomplished, for example, by binding to a protein's intended target, such as a receptor or binding partner, thereby blocking or reducing activity of the protein.

Furthermore, an interfering molecule of the invention can inhibit a gene by reducing or inhibiting expression of the gene, inter alia by interfering with gene expression (transcription, processing, translation, post-translational modification), for example, by interfering with the gene's mRNA and blocking translation of the gene product or by post-translational modification of a gene product, or by causing changes in intracellular localization.

Examples of suitable interfering molecules include, but are not limited to, small molecules, antibodies, antisense RNAs, cDNAs, dominant-negative forms of molecules such as, without limitation, Plxnd1, Neuropilin, or Semaphorin peptides, protein kinase inhibitors, combinations thereof, and the like.

In still other embodiments, an API according to the present disclosure comprises an agonist. As used herein, the term "agonist" is used in the broadest sense and includes any molecule that mimics a biological activity of a native polypeptide disclosed herein. An agonist can be any chemical compound, nucleic acid molecule, peptide or polypeptide can enhance activity of a gene product (e.g., by stabilizing the gene product, preventing its proteolytic degradation or increasing its enzymatic or binding activity or directly activating expression of a gene).

An agonist of the invention can increase the activity of a protein that is encoded by a gene either directly or indirectly. Direct activation can be accomplished, for example, by binding to a protein and thereby enhancing binding of the protein to an intended target, such as a receptor. Indirect activation can be accomplished, for example, by binding to a protein's intended target, such as a receptor or binding partner, and enhancing activity, e.g. by increasing the effective concentration of the target. Furthermore, an agonist of the invention can activate a gene by increasing expression of the gene, e.g., by increasing gene expression (transcription, processing, translation, post-translational modification), for example, by stabilizing the gene's mRNA or blocking degradation of the mRNA transcript, or by post-translational modification of a gene product, or by causing changes in intracellular localization.

Suitable agonist molecules specifically include agonist antibodies or antibody fragments, fragments or amino acid sequence variants of native polypeptides, peptides, small organic molecules, etc. Methods for identifying agonists of a native polypeptide may comprise contacting a native polypeptide with a candidate agonist molecule and measuring a detectable change in one or more biological activities normally associated with the native polypeptide.

In some embodiments, an agonist of the present disclosure comprises a molecule capable of activating components downstream in the Plxnd1 signaling pathway. In some embodiments, an agonist of the present disclosure is capable of activating or increasing levels or activity of the Col5a1 gene, or of products of the Col5a1 gene. In other embodiments, an agonist of the present disclosure is capable of activating components of the Plxnd1 pathway that are negatively regulated by the Plxnd1 gene product.

As used herein an "effective" amount or a "therapeutically effective amount" of a pharmaceutical ingredient refers to a nontoxic but sufficient amount of the ingredient to provide the desired effect. For example one desired effect would be the prevention or treatment of insulin resistance, hypoglycemia, hyperglycemia, or other forms of metabolic dysfunction, as measured, for example, by an increase in blood glucose level. An alternative desired effect for the peptides of the present disclosure would include treating hyperglycemia, e.g., as measured by a change in blood glucose level closer to normal, or inducing weight loss/preventing weight gain, e g, as measured by reduction in body weight, or preventing or reducing an increase in body weight, or normalizing body fat distribution.

In embodiments, an effective or therapeutically effective amount is capable of reducing the level of VAT in a subject. In some embodiments, an effective or therapeutically effective amount is capable of reducing the VAT:SAT ratio in a subject. In other embodiments, an effective or therapeutically effective amount is capable of reducing the level or proportion of hypertrophic VAT morphology in a subject. In still other embodiments, an effective or therapeutically effective amount is capable of increasing the level or proportion of hyperplastic VAT morphology in a subject.

The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

As used herein, the term "patient" or "subject" refers to mammals, including humans, animal pets, farm animals, zoo animals, and the like. Further, the patient or subject of the present disclosure may refer to any vertebrate species. In one embodiment, the patient or subject is a human.

As used herein, the terms "treating" or "treatment" refer to the administration of one or more APIs to a patient who has a condition or disorder or a predisposition toward a condition or disorder, with the purpose to alleviate, relieve, remedy, ameliorate, improve, slow or stop the progression or worsening of the disease, or at least one symptom of the disease, condition or disorder, or the predisposition toward the condition or disorder. Thus, "treating" includes prophylaxis of the specific disorder or condition, or alleviation of the symptoms associated with a specific disorder or condition and/or preventing or eliminating said symptoms. For example, as used herein the term "treating diabetes" will refer in general to altering glucose blood levels in the direction of normal levels and may include increasing or decreasing blood glucose levels depending on a given situation.

Methods well known to those skilled in the art can be used to practice embodiments of the present disclosure. See, for example, techniques as described in Maniatis et al., 1989, MOLECULAR CLONING: A LABORATORY MANUAL, Cold Spring Harbor Laboratory, New York; Ausubel et al., 1989, CURRENT PROTOCOLS IN MOLECULAR BIOLOGY, Greene Publishing Associates and Wiley Interscience, New York; Sambrook, J. et al., 2001, "MOLECULAR CLONING: A LABORATORY MANUAL," 3.sup.rd edition, Cold Spring Harbor Laboratory Press. The contents of the above are incorporated in their entirety herein by reference.

Additional methods well known to those skilled in the art can be used to prepare pharmaceutically acceptable compositions and methods of treatment according to the present disclosure. See, for example, Goodman & Gilman, 2005, THE PHARMACOLOGICAL BASIS OF THERAPEUTICS," 11th Edition, McGraw-Hill. The contents of the above are incorporated in their entirety herein by reference.

Additional methods well known to those skilled in the art can be used for therapeutic intervention in subjects with metabolic dysfunction. (See e.g. Physician's Desk Reference, Medical Economics Company, Inc. Montvale, N.J. (54th Edition) 2000; American Association of Clinical Endocrinologists Medical Guidelines for Clinical Practice for Growth Hormone use in Adults and Children-2003 Update, AACE Growth Hormone Task Force, Endocrine Practice (2003), 9:65-76.)

The disclosure also provides methods for predicting whether a subject is suffering from a metabolic dysfunction, or is at elevated risk for metabolic dysfunction. In these embodiments, the methods comprise the steps of: (a) isolating a biosample from a subject; (b) determining a level or concentration of one or more biomarkers present in the biosample; and (c) identifying the subject as suffering from a metabolic dysfunction, or is at elevated risk for metabolic dysfunction, when the level or concentration of one or more biomarkers is increased or decreased relative to a control level or range.

The disclosure also provides methods for identifying a subject that is eligible for reimbursement of an insurance claim for treatment of metabolic dysfunction. In these embodiments, the methods comprise the steps of: (a) isolating a biosample from a subject; (b) determining a level or concentration of one or more biomarkers present in the biosample; and (c) as eligible for reimbursement of the insurance claim when the concentration of one or more biomarkers is increased or decreased relative to an insurance control value. In these embodiments, the insurance control value refers to an amount or range of amounts of a biochemical marker.

The insurance control value refers to an amount or range of amounts of one or more biochemical markers found in a comparable biosample in subjects not suffering from metabolic dysfunction, and used as an insurance reimbursement criterion by, inter alia, a health insurer. In another embodiment, insurance coverage of an individual is assessed as a function of actuarial data that is obtained from individuals with changes in concentration of the one or more biomarkers disclosed herein. A control level according to embodiments of the present methods is based on a database of biochemical marker such comprising one or more biomarkers from previously tested subjects who did not exhibit or develop metabolic dysfunction over a clinically relevant time frame. Additionally, a control level according to embodiments of the present methods is based on an individual that did not file a reimbursement claim based on metabolic dysfunction within an actuarially relevant time period.

The disclosure also provides methods for determining the efficacy of a treatment for metabolic dysfunction in a subject. In these embodiments, the methods comprise the steps of: (a) treating a subject for a metabolic dysfunction; (b) isolating a biosample from the subject; (c) determining a level or concentration of one or more biomarkers present in the biosample; and (d) determining the efficacy of the treatment for metabolic dysfunction when the concentration of one or more biomarkers is increased or decreased relative to a pretreatment level or pre-treatment range of the one or more biomarkers.

As used herein "pre-treatment level" or "pre-treatment range" refers to a level or concentration of one or more biomarkers in a biosample isolated from a subject before administering treatment for a disorder characterized by metabolic dysfunction. A pretreatment level or pre-treatment range includes, without limitation, an average of multiple measurements of the level or concentration of one or more biomarkers, or range of one or more biomarkers, based on multiple measurements from a subject.

In some embodiments of the present disclosure, the level or concentration of one or more biomarkers is increased relative to a control level or range. In other embodiments, the level or concentration of one or more biomarkers is decreased relative to a control level or range. In still other embodiments, the level or concentration of one or more biomarkers is decreased, whereas the level or concentration of other biomarkers are increased, relative to a control level or range.

In embodiments, the level or concentration of one or more biomarkers changes by at least about 10 percent, for example, by at least about 25, 30, 35, 40, 45, 50, 55, 60, 65, 70, 75, 80, 85, 90, 95 or 100 percent, relative to a control level or range. In some embodiments, the level or concentration of one or more biomarkers changes by at least about 2-fold, for example, at least about 4, 6, 8, 10, 20, 40, 60, 80, or 100 fold, relative to a control level or range.

As used herein, the term "biological sample" or "biosample" or "sample" isolated from a subject includes, but is not limited to, a tissue or bodily fluid obtained from an animal, preferably a mammal and most preferably a human. For example, a biological sample can be biopsy material, bone marrow samples, blood, blood plasma, serum or cellular fraction thereof, urine, feces, saliva, tears, or cells derived from a biological source. In one embodiment, the mammal is a human suspected of having or previously diagnosed as having or in need of screening for metabolic dysfunction, in particular insulin resistance or diabetes. In certain embodiments, a biological sample is a sample of adipose tissue.

As used herein "concentration" refers to both percent concentration and absolute concentration of a biomarker. "Percent concentration" refers to the comparative concentration of a biomarker with respect to another. "Absolute concentration" refers to a direct measurement of the biomarker without comparison to other detected species.

A "control level" as used herein refers to an amount or range of amounts of a biochemical marker, such as, without limitation, Plxnd1 or Col5a1, found in a comparable biosample in subjects not suffering from metabolic dysfunction, metabolic syndrome or Type II diabetes. The control level can also be based on a database of biochemical markers such as from previously tested subjects who did not convert to metabolic dysfunction, metabolic syndrome or diabetes over a clinically relevant time.

In embodiments, the one or more biomarkers comprise the genes, or gene products, selected from collagen, type I, alpha 2 (COL1A2 in human, col1a2 in zebrafish); collagen, type II, alpha 1 (COL2A1 in human, col2a1a col2a1b in zebrafish); collagen, type IV, alpha 1 (COL4A1 in human, col4a1 in zebrafish); collagen, type V, alpha 2 (COL5A2 in human, col5a2a col5a2b in zebrafish); collagen, type V, alpha 3 (COL5A3 in humans, col5a3a col5a3b in zebrafish); collagen, type VI, alpha 1 (COL6A1 in human, col6a1 in zebrafish); fibronectin 1 (FN1 in human, fn1a/fn1b in zebrafish); aggrecan (ACAN in human, acana acanb in zebrafish); laminin, alpha 1 (LAMA1 in human, lama1 in zebrafish); glypican 4 (GPC4 in human, gpc4 in zebrafish); and secreted protein, acidic, cysteine-rich (osteonectin) (SPARC in human, sparc in zebrafish). In some embodiments, the control sample is a biological sample from a normal subject, i.e. an individual with normal metabolic function, or one who responds to therapy for a condition characterized by metabolic dysfunction. In a particular aspect, the biological sample is comprised of adipose tissue.

In some embodiments, a panel of biomarkers capable of predicting the occurrence of metabolic dysfunction, determining the efficacy of a treatment for metabolic dysfunction is provided. Embodiments of a biomarker panel are comprised of two or more biomarkers. In one embodiment, a biomarker panel comprises the genes, or gene products of PLXND1/plxnd1 and COL5A1 col5a1.

In other embodiments, the subject is then included or enrolled in an insurance plan based on the insurable status of the subject or wherein the rate or cost of the insurance is based on the insurable status of the subject. Alternatively, the subject is then excluded from an insurance plan based on the insurable status of the subject. In some such instances, an organization that provides medical insurance requests or otherwise obtains information concerning a subject's biochemical marker status and uses that information to determine an appropriate medical insurance premium or reimbursement of an insurance claim relating to treatment of the subject.

The invention will be further described in the following examples, which do not limit the scope of the invention described in the claims.

The Examples that follow are illustrative of specific embodiments of the invention and various uses thereof. They are set forth for explanatory purposes only and are not to be taken as limiting the invention.

EXAMPLES

Example 1 Methods of Zebrafish Plxnd1 Engineering and Analysis

Zebrafish husbandry and staging. To test the role of Plxnd1 in body fat distribution, Zebrafish were genetically engineered to disrupt the function of the Plxnd1 gene according to methods known to the art, described in the present disclosure, as well as methods and references incorporated herein. Zebrafish were raised, fed, and housed as described. (Westerfield M (2000) *The Zebrafish Book-A guide for the laboratory use of zebrafish (Danio rerio)*. University of Oregon Press, Eugene, Oreg.; Flynn E J, et al. (2009), Journal of lipid research 50(8):1641-1652; Imrie D & Sadler K C (2010), Developmental dynamics. 239(11): 3013-3023.) The plxnd$^{fov01b}$ null mutation was maintained on transgenic Tg(fli1a:egfp)$^{y1}$ (hereafter referred to as fli1a: EGFP) or Tg(kdr1:HsHRAS-mCherry)$^{s896}$ (hereafter referred to flk1:mCherry) on Ekkwill backgrounds. (Torres-Vazquez J, et al. (2004), Developmental cell 7(1):117-123; Childs S, et al. (2002), Development 129(4):973-982; Chi N C, et al. (2008), Genes Dev 22(6):734-739; Jin S W, et al. (2005), Development 132(23):5199-5209; Lawson N D & Weinstein B M (2002), Developmental biology 248(2):307-318. VAT surrounding the pancreas and SAT at the horizontal myoseptum were used as representative VAT and SATs. (Imrie D & Sadler K C (2010), Developmental dynamics. 239(11):3013-3023.) Experiments were conducted on zebrafish between 30-50 days post fertilization, unless otherwise stated, and standard length (SL) was used to stage zebrafish. (Parichy D M, et al. (2009), Developmental dynamics 238(12):2975-3015.)

Zebrafish lipid staining, imaging and morphometrics. Nile Red (Sigma, #N1 142) and LipidTOX (Invitrogen, #H34476) staining were undertaken as described. (Minchin J E & Rawls J F (2011), Methods in cell biology 105C:63-86.) Live Nile Red stained animals were imaged on a Leica M205 stereomicroscope. For confocal analyses, zebrafish were euthanized in 1.34 g/L MS222, AT dissected and fixed in 4% paraformaldehyde overnight at 4 C before staining with LipidTOX. Hoechst and 5-Ethynyl Uridine (EdU) were used from the Click-iT EdU Imaging Kit (Invitrogen, #C10338). 5-DTAF (Anaspec, #81001) was used at 200 pg/ml in 0.1M NaHCO$_3$ for 2 h. (Lackey D E, et al. (2014), American journal of physiology. Endocrinology and metabolism 306(3):E233-246.) Specimens were mounted as described (Minchin J E & Rawls J F (2011), Methods in cell biology 105C:63-86.). Z-stacks were obtained either on (i) an Olympus FV1000MPE multiphoton confocal microscope equipped with a 20×1NA water dipping objective, or (ii) a Zeiss 780LSM equipped with a 20×1NA water dipping objective. All operations on Z-stacks were conducted in Fiji/ImageJ version 1.47n. Z-stacks were deconvolved and processed before segmentation. LDs were segmented using the fast marching method and distance weighted interpolation as implemented within TrakEM2. (Cardona A, et al. (2010), PLoS biology 8(10); Cardona A, et al. (2012), PLoS one 7(6):e38011. LD volume and Feret's diameter were quantified using the 3D suite. (Iannuccelli E, et al. (2010), Bioinformatics 26(5):696-697.) Analyses were performed by multiple operators with no knowledge of specimen genotype.

Zebrafish Immunofluorescence and Histological Staining. Immunohistochemistry was performed as previously described (Kanther M, et al. (2011), Gastroenterology 141(1):197-207.) Immunohistochemistry was conducted with antibodies to Type V collagen (Col5) (Rockland, #600-401-107S), Laminin (Sigma, #L-9393), WCL15 (Romano N, et al. (1998), Anatomy and embryology 198(1):31-41; van der Sar A M, et al. (2004), Trends in microbiology 12(10):451-457), and Alexa 568 (Invitrogen, #A-1 1011). Transmission electron microscopy was carried out as described previously. (Flynn E J, et al. (2009), Journal of lipid research 50(8): 1641-1652.) Whole 10-12 mm SL fish were processed for paraffin sectioning and Masson's trichrome, combined Masson's and Elastin, periodic acid Schiff (PAS) and Alcian Blue stains. (Sabaliauskas N A, et al. (2006), Methods 39(3):246-254.)

Figure 18:
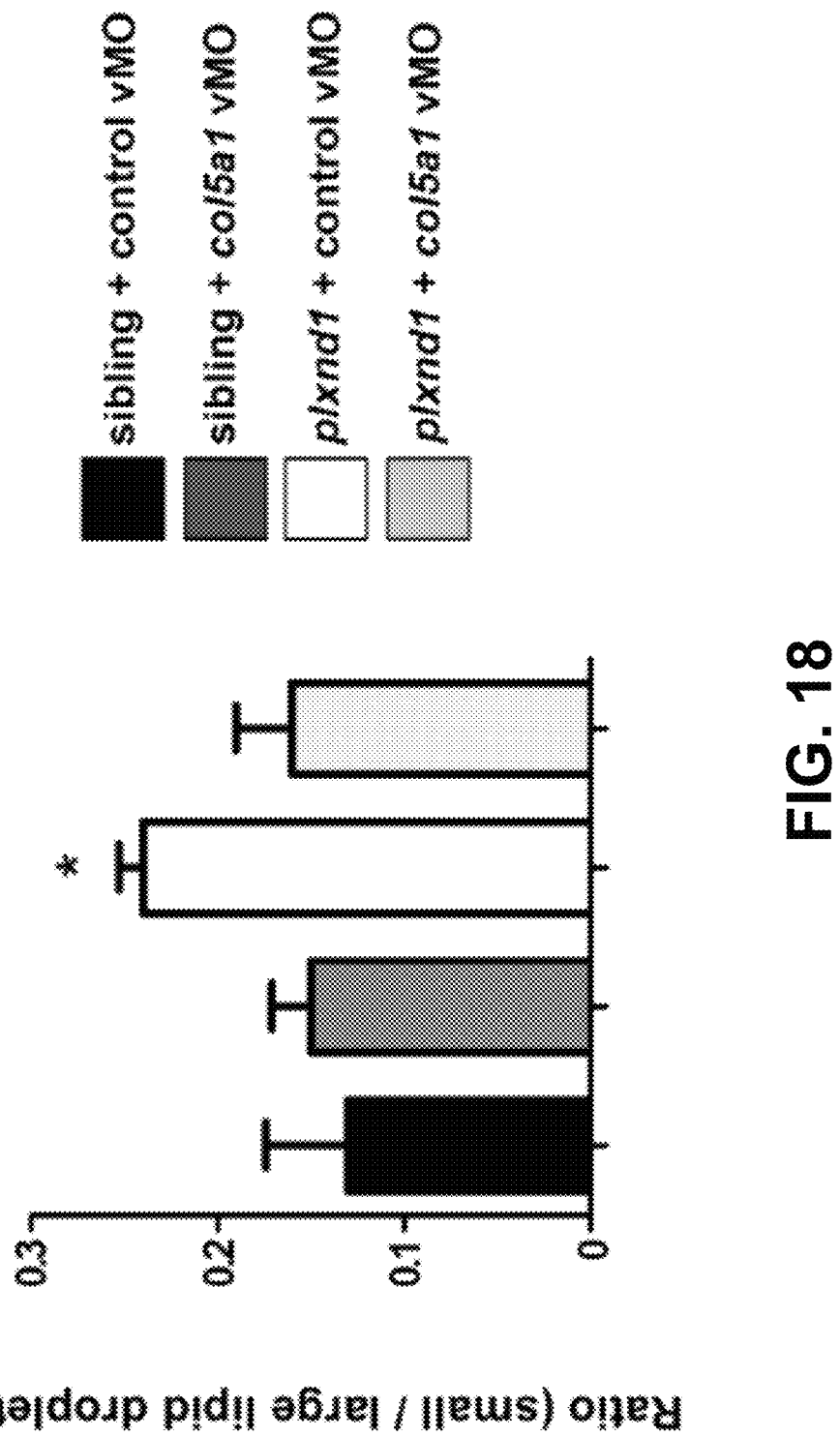
FIG. 18 shows quantification of the ratio of lipid droplets from zebrafish VAT categorized into small (<20 pm-60 p.m diameter) and large (>60 p.m diameter) lipid droplets for the indicated genotypes and vMOs. Only plxnd1 mutants injected with control vMO exhibited an increase in the ratio of small:large LDs.

Zebrafish qRT-PCR. RNA extraction, PCR and quantitative RT-PCR (qRT-PCR) was performed as previously described using total RNA from dissected whole VAT tissue of 10 mm zebrafish. (Rawls J F, et al. (2007), PNAS 104(18):7622-7627.) VAT and SAT were dissected from adult Ekkwill strain wild-type zebrafish and used to assess plxnd1 mRNA levels (FIG. 18(B)). Samples contained 5-8 siblings or mutants per group, and qRT-PCR was ran with three biological replicate groups, and reactions ran in triplicate. Primer sequences are listed in Table 1.

TABLE 1

| Gene symbol | Gene name | Forward (5'-3') (SEQ ID NO.) | Reverse (5'-3') (SEQ ID NO.) |
|---|---|---|---|
| pck1 | Phosphoenolpyruvate carboxykinase 1 | CATCACGCATCGCTAAAG AG (SEQ ID NO.: 01) | GCTCTCAGATTCCCTTCTT TGTC (SEQ ID NO.: 02) |
| irs1 | insulin receptor substrate 1 | GAGAGCAACATGTTCCTG ATTGGAATGCT (SEQ ID NO.: 03) | TCTGAGGTCCGGCTTGCAG TGAATTGG (SEQ ID NO.: 04) |
| irs2 | insulin receptor substrate 2 | GGCTTTAAGACTGGCGGT TGTTGTAA (SEQ ID NO.: 05) | GTCACGG (SEQ ID NO.: 06) TTAAGATGAGGTGCAAAG |
| ptpn6 | protein tyrosine phosphatase, non-receptor type 6 | ATATTCAGAGCAGAGTAA ATCAG (SEQ ID NO.: 07) | GGGTGCAGATGAGCGCAG TTC (SEQ ID NO.: 08) |
| insra | insulin receptor a | CAACATGCCCCCTCACCA CT (SEQ ID NO.: 09) | CGACACACATGTTGTTGTG (SEQ ID NO.: 10) |
| insrb | insulin receptor b | GACTGATTACTATCGCAA GGG (SEQ ID NO.: 11) | TCCAGGTATCCTCCGTCCA T (SEQ ID NO.: 12) |
| Plxnd1 | Plexin D1 | AGAACCCCAAACTGATGC TG (SEQ ID NO.: 13) | ATCTGCTGTTTGATGGCAC A (SEQ ID NO.: 14) |
| 18S | | CACTTGTCCCTCTAAGAAG TTGGTTGATTCCGATAACG GCA (SEQ ID NO.: 15) | AACGA (SEQ ID NO.: 16) |
| fabp11a | Fatty acid binding protein 11a | GGCAAACTTGTGCAGAAA CA (SEQ ID NO.: 17) | GAACTGAGCCTGGCATCTT C SEQ ID NO.: 18) |
| cebpa | CCAAT/enhancer binding protein (C/EBP), alpha | ATCAGCGCCTACATTGAT CC (SEQ ID NO.: 19) | TTGCTTGGCTGTCGTAGAT G (SEQ ID NO.: 20) |
| cebpb | CCAAT/enhancer binding protein (C/EBP), beta | CTGAGGGGAACAAGAGC AAG (SEQ ID NO.: 21) | AGTCTGGTACGGCAGGTA CG (SEQ ID NO.: 22) |
| pparg | peroxisome proliferator- activated receptor gamma | TGCCGCATACACAAGAAG AG (SEQ ID NO.: 23) | ATGTGGTTCACGTCACTGG A (SEQ ID NO.: 24) |
| toll a2 | collagen, type I, alpha 2 | ACCAGGCAGTCCAGAAC ATC (SEQ ID NO.: 25) | GGTTTCCATTCTCAGCATC C (SEQ ID NO.: 26) |
| col2a1a | collagen, type II, alpha 1a | GAACTTCCTCAGGCTGCT GT (SEQ ID NO.: 27) | TGTAAGCCACGCTGTTCTT G (SEQ ID NO.: 28) |

TABLE 1-continued

| Gene symbol | Gene name | Forward (5'-3') (SEQ ID NO.) | Reverse (5'-3') (SEQ ID NO.) |
|---|---|---|---|
| col4a1 | collagen, type IV, alpha 1 | CAGGAAGGCCAGGACTA CAA (SEQ ID NO.: 29) | CGTTCACCTGGAAATCCTC T (SEQ ID NO.: 30) |
| col5a1 | procollagen, type V, alpha 1 | CACCCTATGCCTTATCAG TCTTC (SEQ ID NO.: 31) | TGTTTCATTTGCTCAATCT CCA (SEQ ID NO.: 32) |
| col5a2a | collagen, type V, alpha 2a | TACACGTGGTCAAGGAA (SEQ ID NO.: 33) | TCCCCTCACACCAGTAGGT C (SEQ ID NO.: 34) |
| col5a3a | collagen, type V, alpha 3a | AGGGTAAACATGGTCCAG CA (SEQ ID NO.: 35) | ACCGATTGCACCACTTTCT C SEQ ID NO.: 36) |
| col5a3b | collagen, type V, alpha 3b | GATTACTGCCACACCCAC ATTC (SEQ ID NO.: 37) | TCCTCAAACTCCTCCTCCA CA (SEQ ID NO.: 38) |
| col6a1 | collagen, type VI, alpha 1 | GATGTGTGCTGCTCCTTT GA (SEQ ID NO.: 39) | GCCCCAAAGTCTCCTTTTT C (SEQ ID NO.: 40) |
| Fn1 | fibronectin 1a | GGAGGGATCCTGTCTGAC TG (SEQ ID NO.: 41) | TTGCTACCTTGAGCCTTGC T (SEQ ID NO.: 42) |
| acana | aggrecan a | GACCAAACCAGCCTGACA AT (SEQ ID NO.: 43) | TGCATGTAAAAGGCAGAT GG (SEQ ID NO.: 44) |
| lama1 | laminin, alpha 1 | ATGCTTCCGCAGATCTTC AT (SEQ ID NO.: 45) | ACCGTCATGAGCTCGTCTC T (SEQ ID NO.: 46) |
| gpc4 | glypican 4 | GCATGTTTCGACTGGTCA AC (SEQ ID NO.: 47) | CCTGCTGACACACTCCATG T SEQ ID NO.: 48) |
| sparc | secreted protein, acidic, cysteine-rich (osteonectin) | AAGAGGAGCCAGCTGTTG AA (SEQ ID NO.: 49) | ATGGTTTAGGCAGGGGTT CT (SEQ ID NO.: 50) |
| col5a1 | procollagen, type V, alpha 1 | TTTCCCAGAGATGGGTTG TG (SEQ ID NO.: 51) | AGGAACGACTGACTGCCT TT (SEQ ID NO.: 52) |
| col5a1 | procollagen, type V, alpha 1 | CAGACGGTGTAACGAAA CTACAG (SEQ ID NO.: 53) | GGGTGCAGAAACCTCACA GT (SEQ ID NO.: 54) |

Zebrafish Plxnd1 Mutants have Reduced Lipid Accumulation in VAT and Altered Body Fat Distribution.

Homozygous plxnd1 null zebrafish mutants and their phenotypically normal siblings were stained with the neutral lipid dye Nile Red, and individual ATs were categorized into; (i) VAT, (ii) SAT or (iii) miscellaneous AT (cranial or associated with the skeleton). Total AT area, and the AT area for each category, was then measured (AT area is known to accurately predict triacylglyceride content in zebrafish). (Tingaud-Sequeira A, et al. (2011), Journal of lipid research 52(9):1765-1772.)

Figures 6A, 6B:
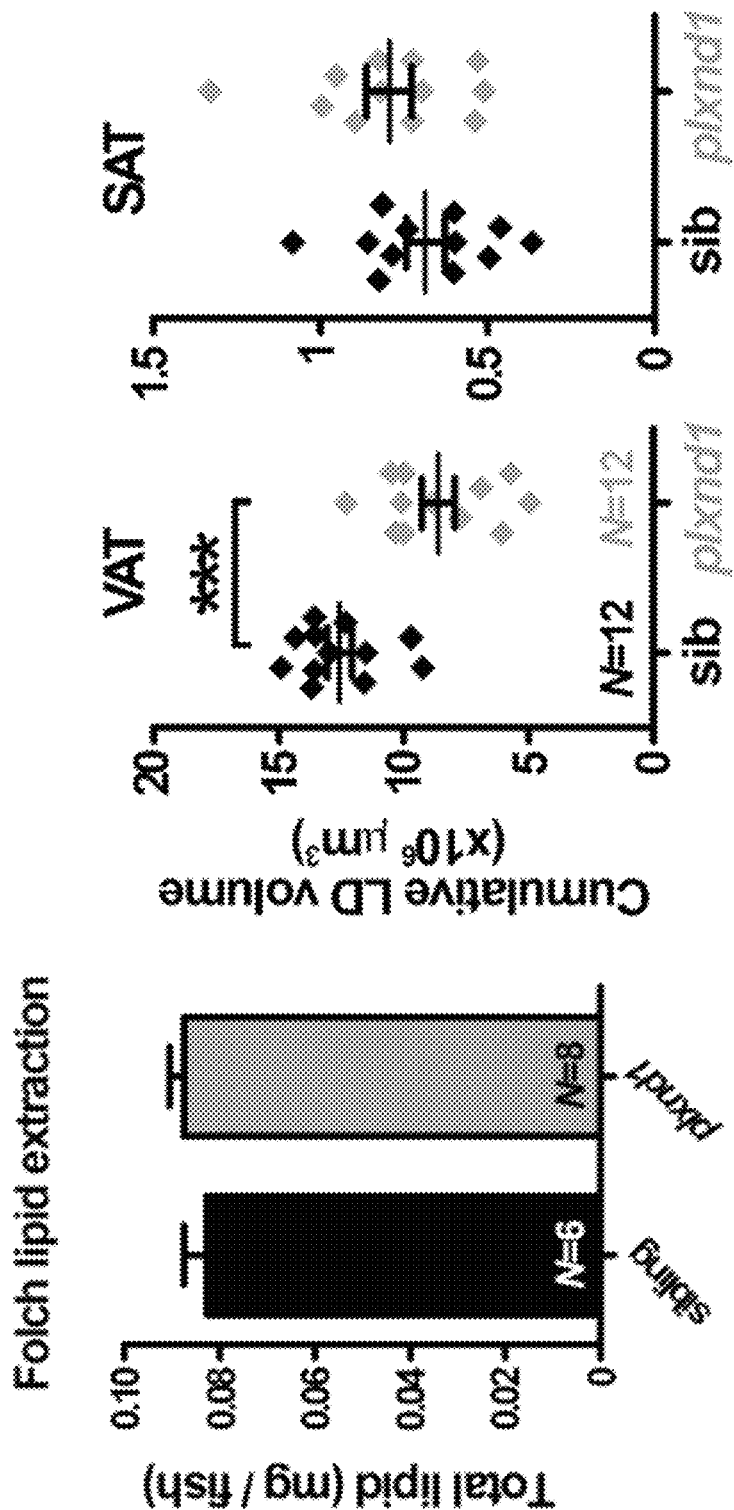
FIG. 6(A) shows Folch lipid extraction revealing similar total lipid levels per fish between siblings and plxnd1 mutants.
FIG. 6(B) shows quantification of the cumulative lipid droplet volume in VAT (left panel) or SAT (right panel).
Figure 6C:
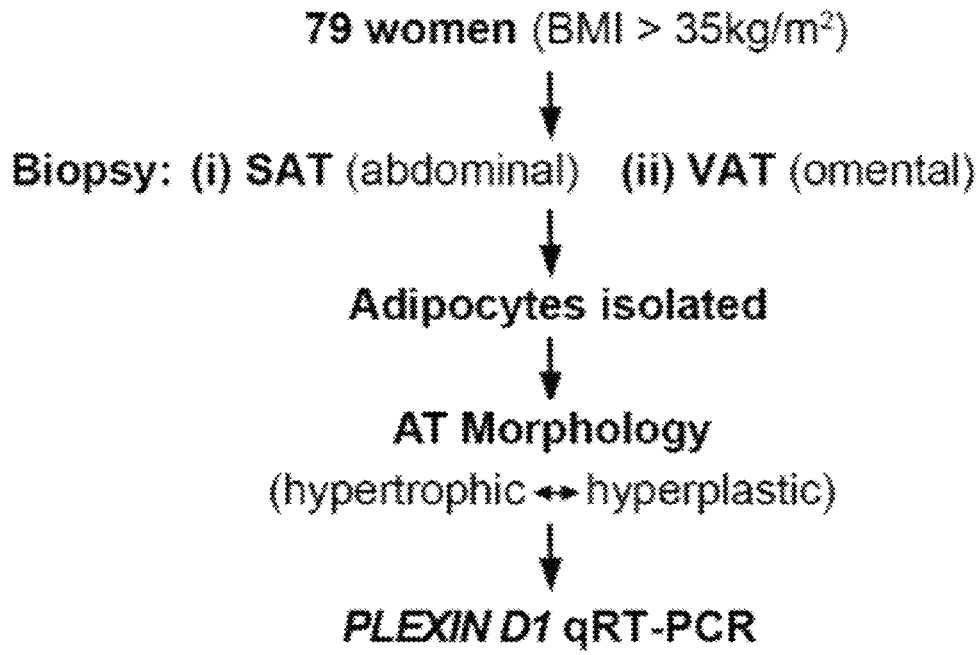
FIG. 6(C) shows the experimental strategy examining the relationship between PLXND1 mRNA levels and AT morphology.

Total AT area per zebrafish was indistinguishable between plxnd1 mutants and siblings (FIG. 1(A)), and total extracted lipid levels (Folch, J., M. Lees, and G. H. Sloane Stanley (1957) Journal of biological chemistry 226: 497-509.) per fish were identical (FIG. 6(A)). However, VAT area and volume were significantly decreased in plxnd1 mutants (FIG. 1(A), FIG. 6(B)). By contrast, no significant change was observed between plxnd1 mutants and siblings in SAT or miscellaneous AT-localized lipid storage (FIG. 1(A), FIG. 6(B)). The decrease in VAT area in plxnd1 mutants led to a reduced VAT:SAT ratio (FIG. 1(A)).

Figure 1D:
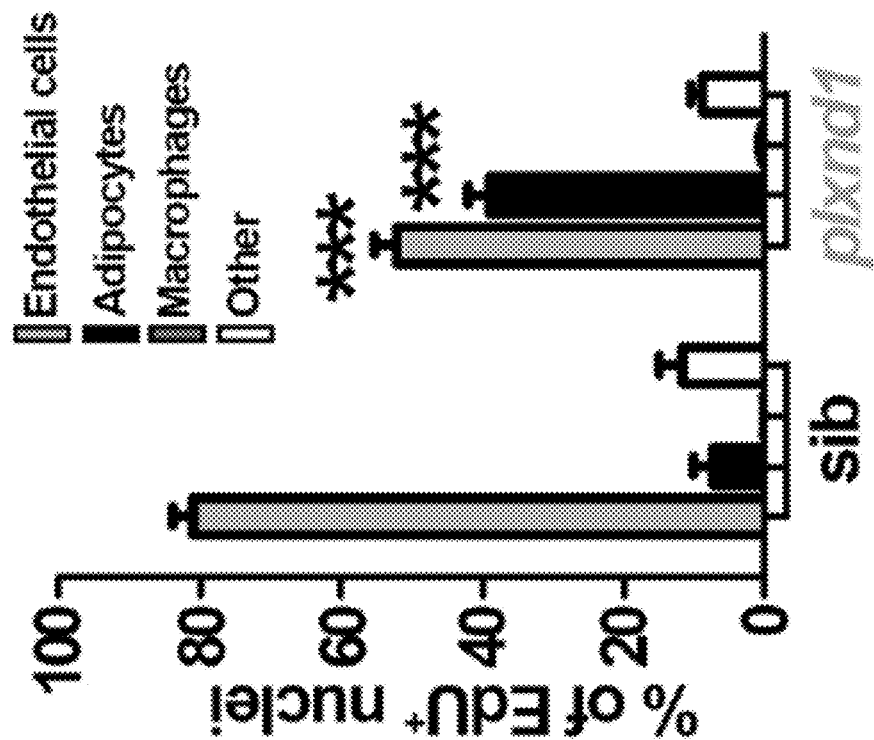
FIG. 1(D) shows quantification of EdU+ nuclei colocalizing with lipid droplet-containing adipocytes, AT macrophages, and endothelial cells from plxnd1 and wild type sibling variants of the fli1a:EGFP transgenic line.
Figure 1C:
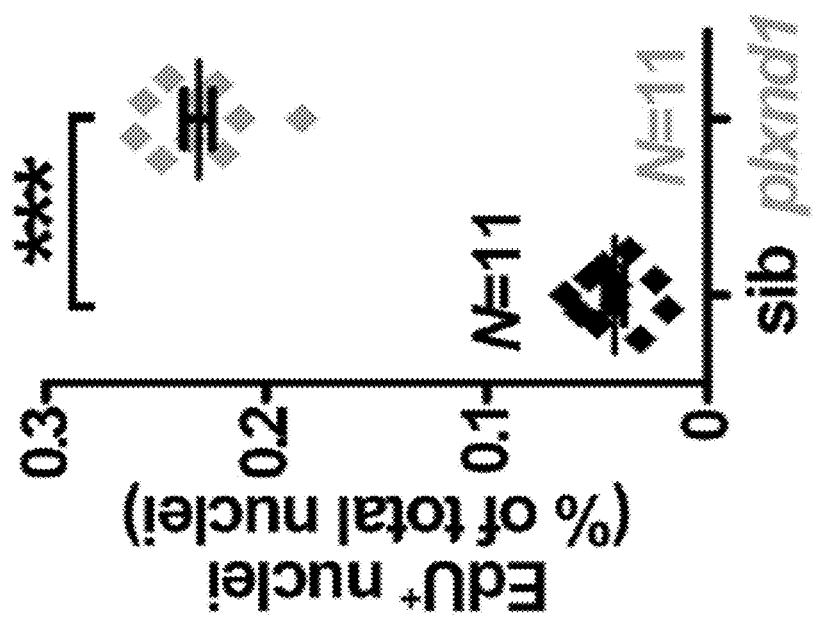
FIG. 1(C) shows quantification of EdU+ nuclei normalized to total nuclei from Z-stacks.
Figure 1E:
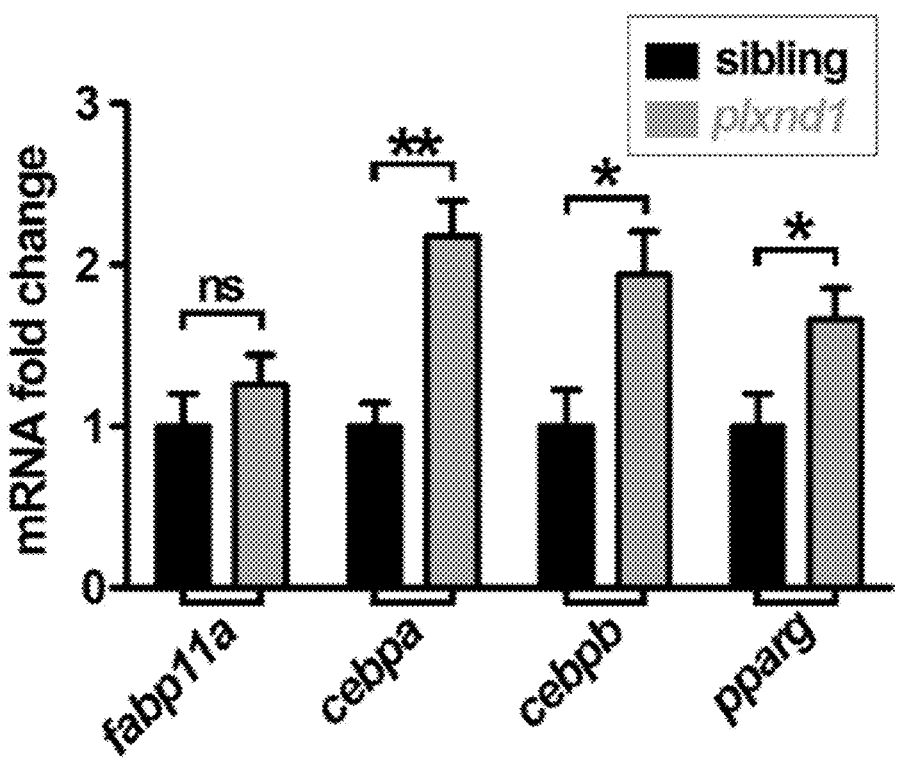
FIG. 1(E) shows that mRNA levels for adipocyte differentiation markers cebpa, cebpb and pparg were increased in plxnd1 VAT by qRT-PCR. Fabp11a, a homolog of mammalian Fabp4/aP2, was unchanged.
Figure 7A:
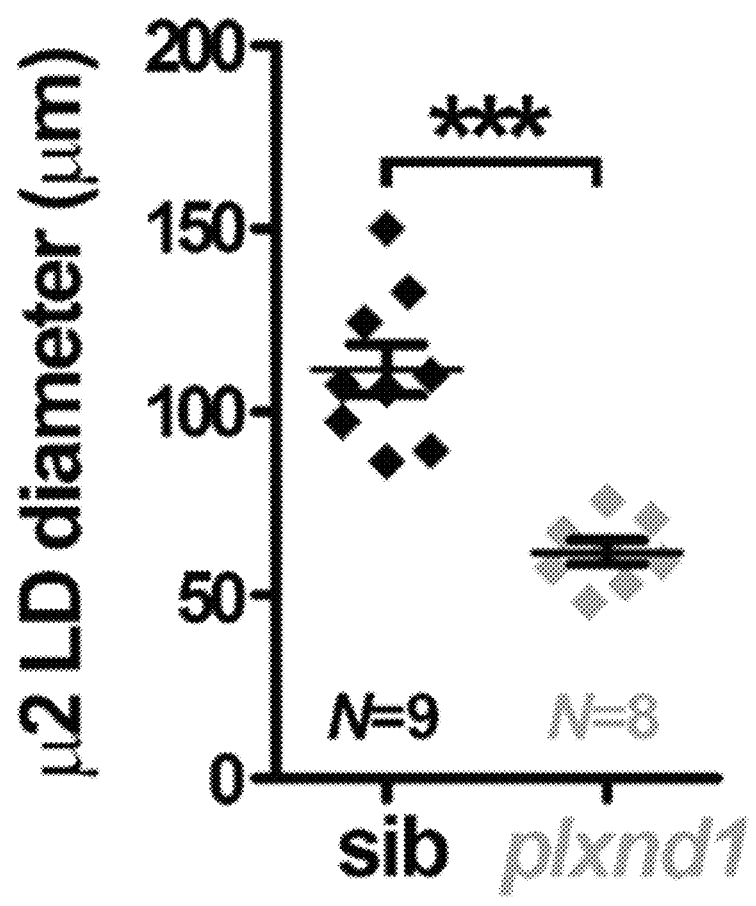
FIG. 7(A) shows comparison of $\mu$2 VAT-LD diameter between plxnd1 and siblings. $\mu$2 VAT-LD diameter was significantly smaller in plxnd1.
Figure 7B:
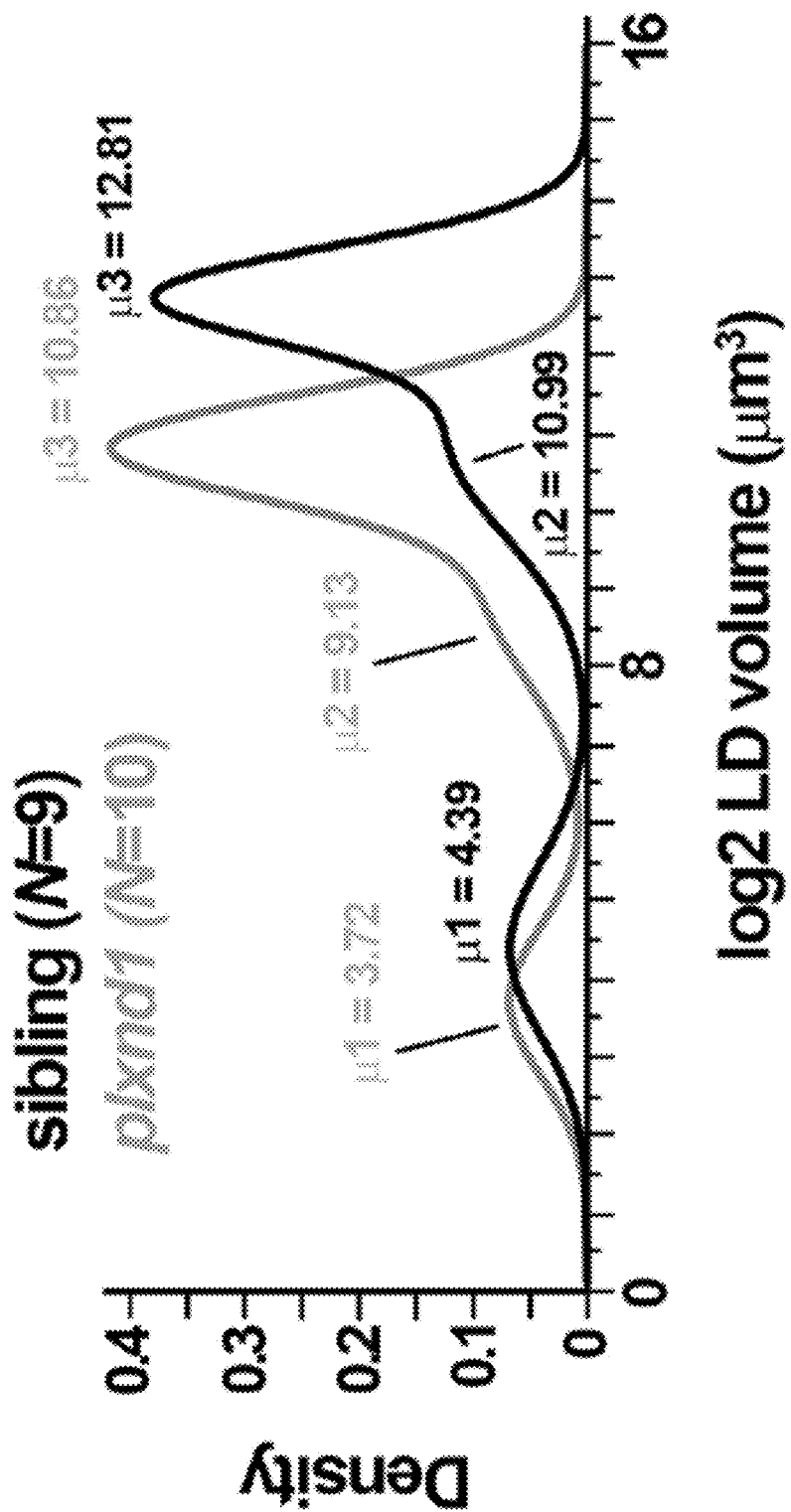
FIG. 7(B) shows a loge distribution of LD volumes revealing a trimodal distribution with plxnd1 LDs smaller than sibling LDs.
Figure 7C:
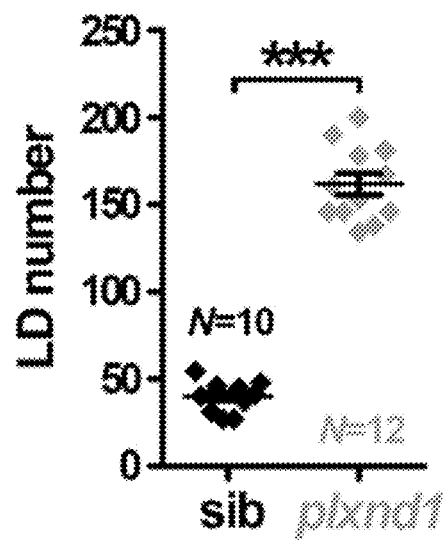
FIG. 7(C) shows a plxnd1 mutants have increased LD number per confocal Z-stack.
Figure 7D:
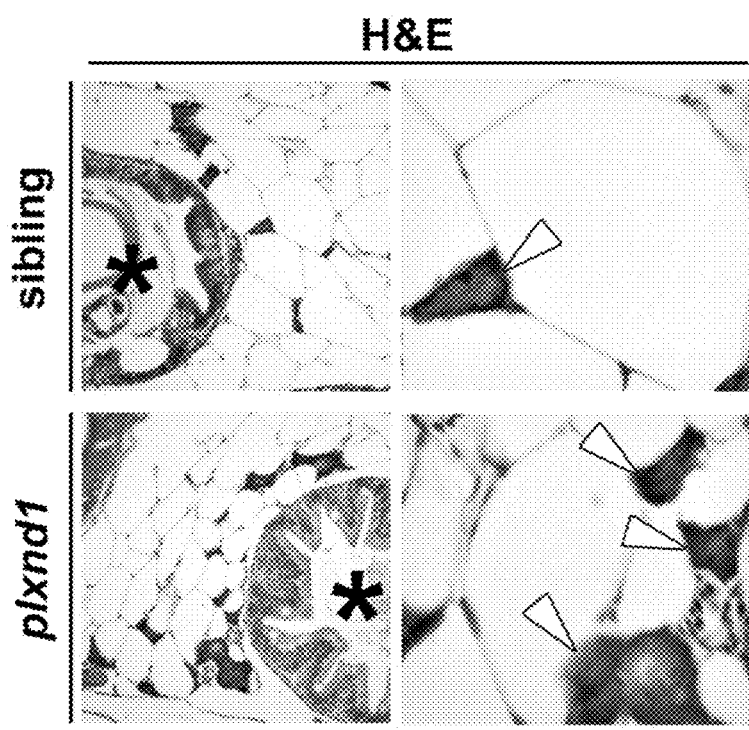
FIG. 7(D) shows stained histological sections indicating the hyperplastic morphology of plxnd1 VAT. Adipocytes are the large, light staining circular structures. The darker staining structures surrounding adipocytes are exocrine pancreatic tissue embedded within the VAT (arrows). Asterisks indicate intestinal tissue.
Figure 7E:
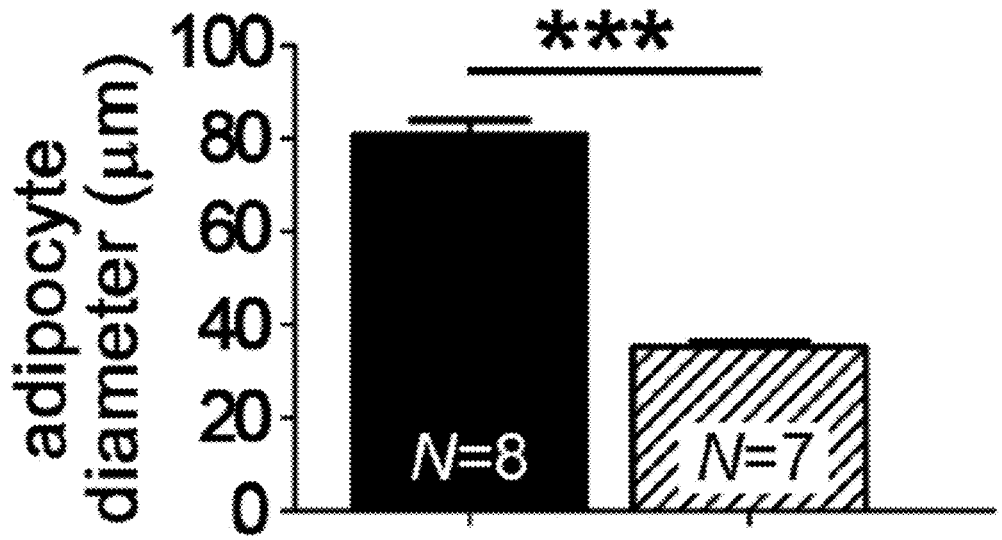
FIG. 7(E) shows VAT adipocyte diameter measured in histological sections.
Figure 7F:
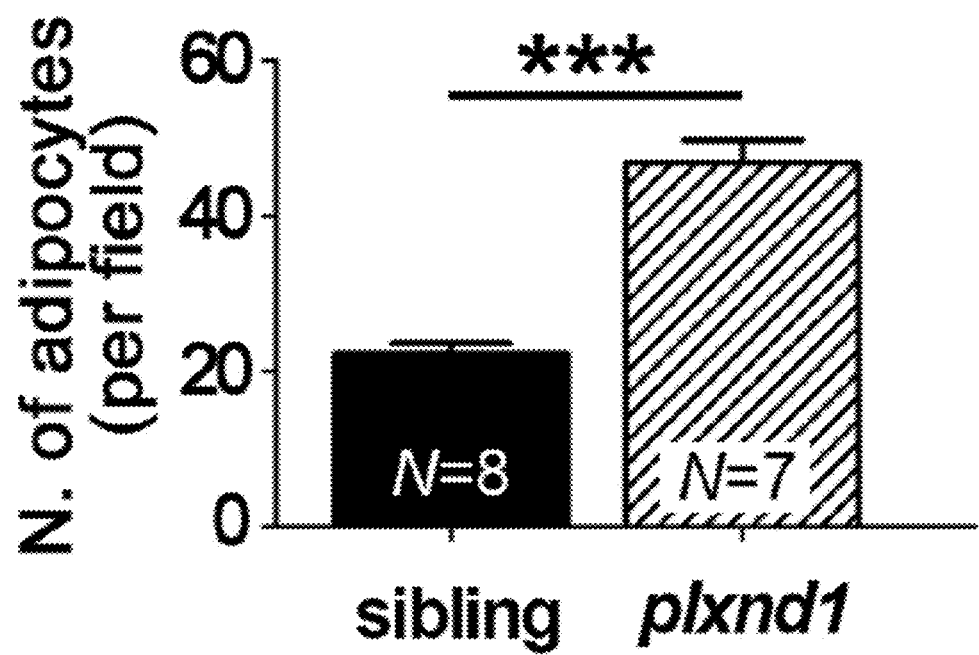
FIG. 7(F) shows number of VAT adipocytes per histological field.
Figure 8A:
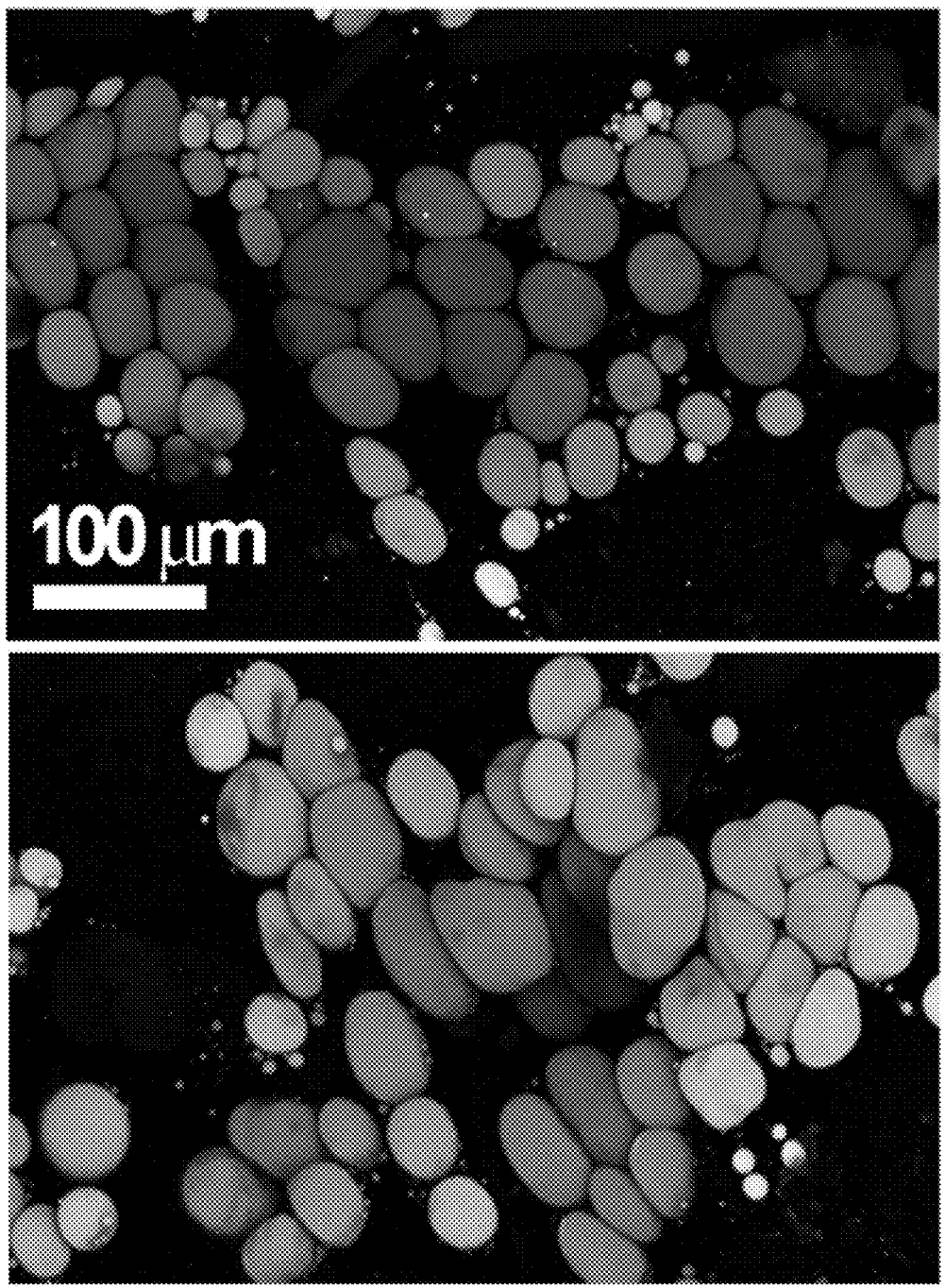
FIG. 8(A) shows maximum intensity projections of SAT LDs in plxnd1 mutants and siblings labelled with LipidTOX.
Figure 8C:
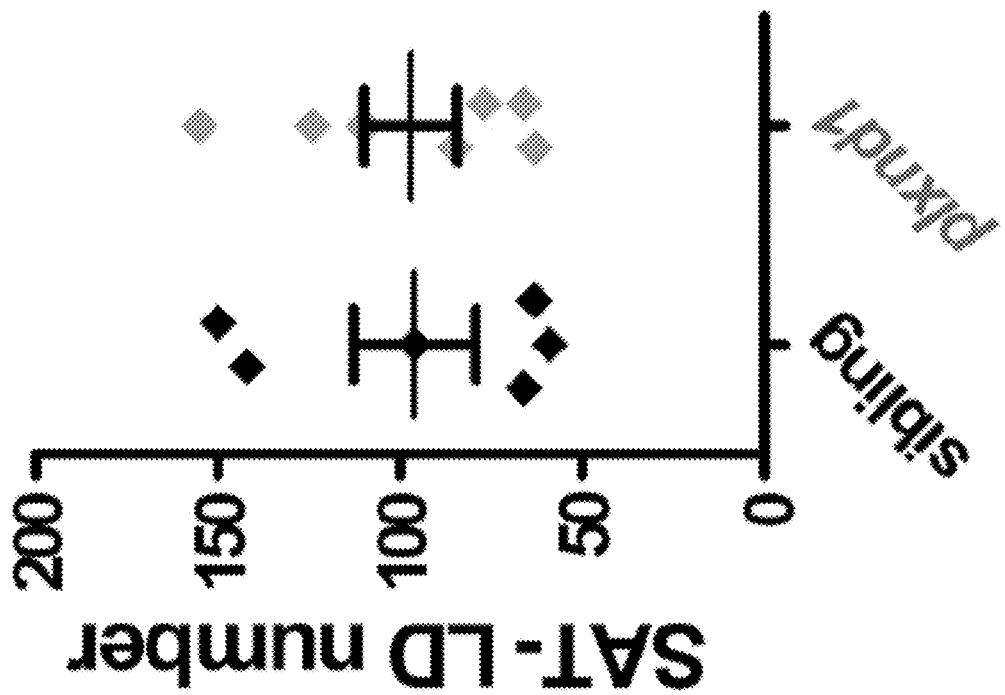
FIG. 8(C) shows SAT-LD number per confocal Z-stack was not different between plxnd1 and siblings.
Figure 8B:
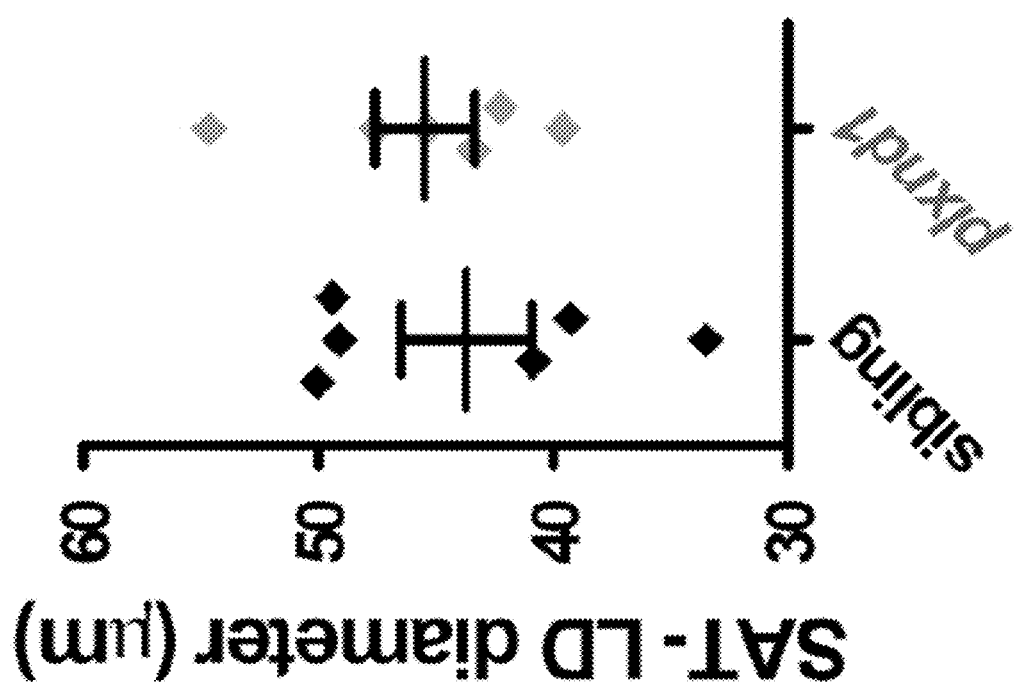
FIG. 8(B) shows mean SAT-LD diameter was not significantly different between plxnd1 and siblings.
Figure 8D:
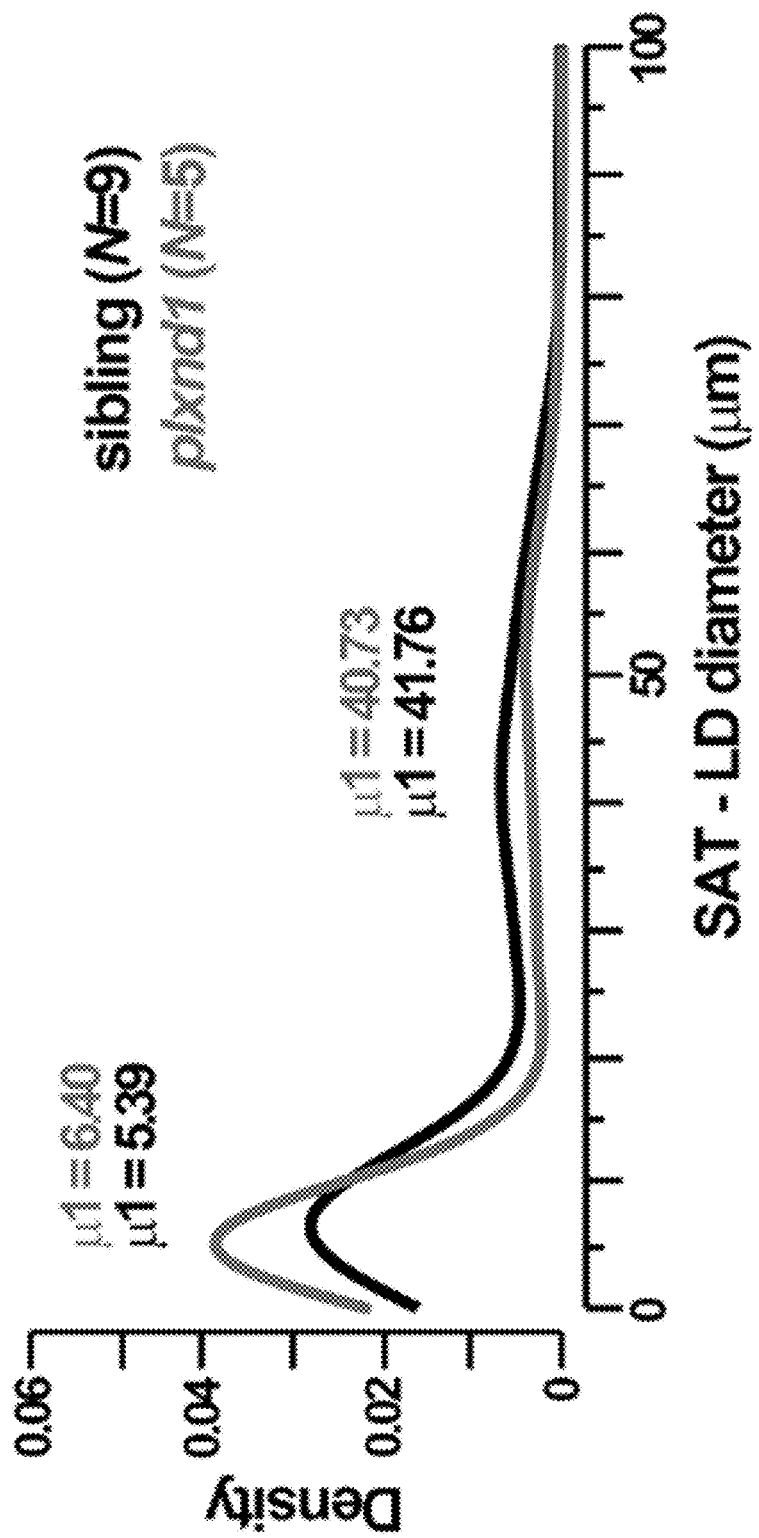
FIG. 8(D) shows the probability density function of SAT-LD diameters modelled using a mixture of 2 normal distributions. The mean ($\mu$) of each distribution is indicated ($\mu 1$ and $\mu 2$). Dispersion ($\sigma$) of each distribution was sibling $\sigma 1=2.51$, sibling $\sigma 2=16.77$, plxnd1 $\sigma 1=2.57$ and plxnd1 $\sigma 2=15.63$. Probabilities ($\pi$) are sibling $\pi 1=0.73$, sibling $\pi 2=0.27$, plxnd1 $\pi 1=0.59$ and plxnd1 $\pi 2=0.41$.

Plxnd1 Deficiency Induces a Hyperproliferative and Hyperplastic State in Zebrafish VAT LD number and size were quantified as measures of hyperplastic and hypertrophic AT morphology. (McMenamin S K, et al. (2013), Endocrinology 154(4):1476-1487.) Both sibling and plxnd1 mutant VAT had a bimodal distribution of LD sizes containing a population of very small LDs that was unaltered between genotypes (FIG. 1(D)), and a second population of large LDs that was significantly smaller in plxnd1 mutants compared to siblings (FIG. 1(D) and FIG. 7(A)). Measurements of LD volume supported the smaller size of plxnd1 mutant VAT LDs (FIG. 7(B)). Furthermore, plxnd1 mutants had a greater number of LDs per unit volume (FIG. 7(C)), and histology confirmed the hyperplastic morphology of plxnd1 mutant VAT (FIG. 7(D)-7(F)).

plxnd1 mutant VAT had a greater number of EdU±proliferating cells than sibling VAT (FIG. 1(C)), of which the majority of EdU+ nuclei belonged to either adipocytes or endothelial cells (FIG. 1(D)). Further, qRT-PCR revealed increased expression of adipocyte differentiation genes (FIG. 1(E)). By contrast, the morphology of plxnd1 SAT was indistinguishable from siblings (FIG. 8). Together, these data demonstrate that plxnd1 deficiency induces adipocyte hyperproliferation, induction of adipocyte differentiation genes and hyperplastic VAT morphology, without affecting SAT morphology.

Example 2: PLXND1 mRNA is Positively Associated with Hypertrophic Morphology in Human VAT, but not SAT Human gene expression and morphology methods. Subjects were investigated in the morning after an overnight fast. To relate PLXND1 expression to AT morphology (FIG.

Figure 19A:
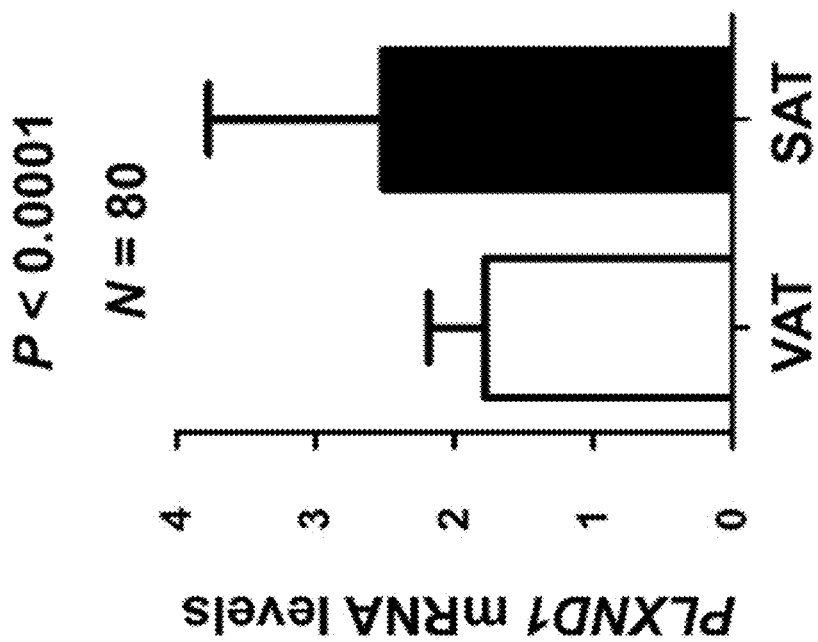
FIG. 19(A) shows qRT-PCR for PLXND1 in human VAT and SAT.
Figure 19B:
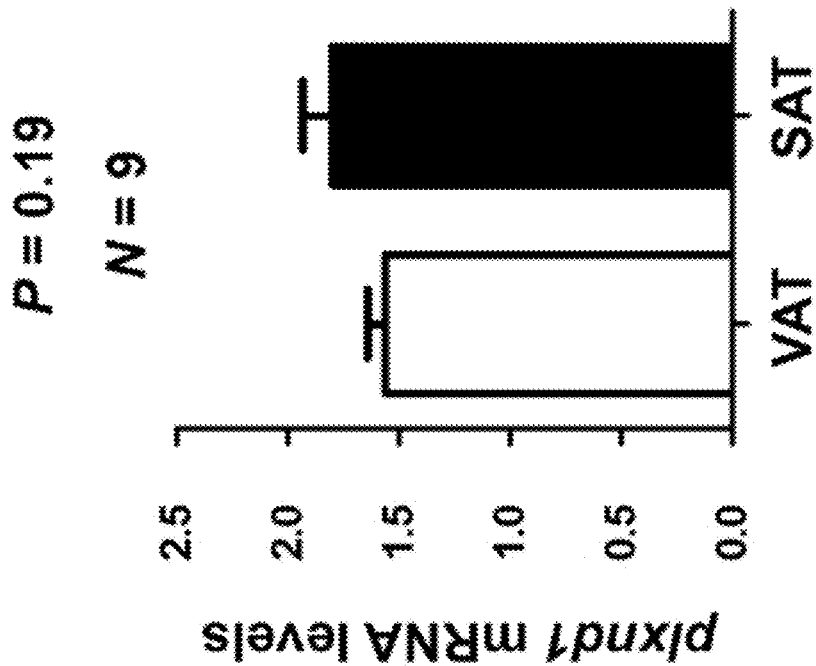
FIG. 19(B) shows qRT-PCR for plxnd1 in adult zebrafish VAT and SAT.

1(F)), VAT and SAT biopsies were taken from 79 obese women scheduled for gastric bypass surgery. Morphology in each adipose depot (hyperplastic/hypertrophic) was determined as described. (Hoffstedt J, et al. (2010), Diabetologia 53(12):2496-2503.) Neither morphology, nor hypertrophic AT were dependent on BMI. mRNA was quantified in AT as described. (Ryden M, et al. (2007), American journal of physiology. Endocrinology and metabolism 292(6):E1847-1855.) qRT-PCR was performed using pre-TaqMan kits for PLXND1 (HS 00391129 ml), and LRP10 (Hs01047362_m1) (Applied Biosystems). Expression of PLXND1 was normalized to the LRP10 internal control using the comparative $C_t$ method. PLXND1 mRNA expression was found to be slightly higher in SAT than VAT (FIG. 19(A)).

Figure 1F:
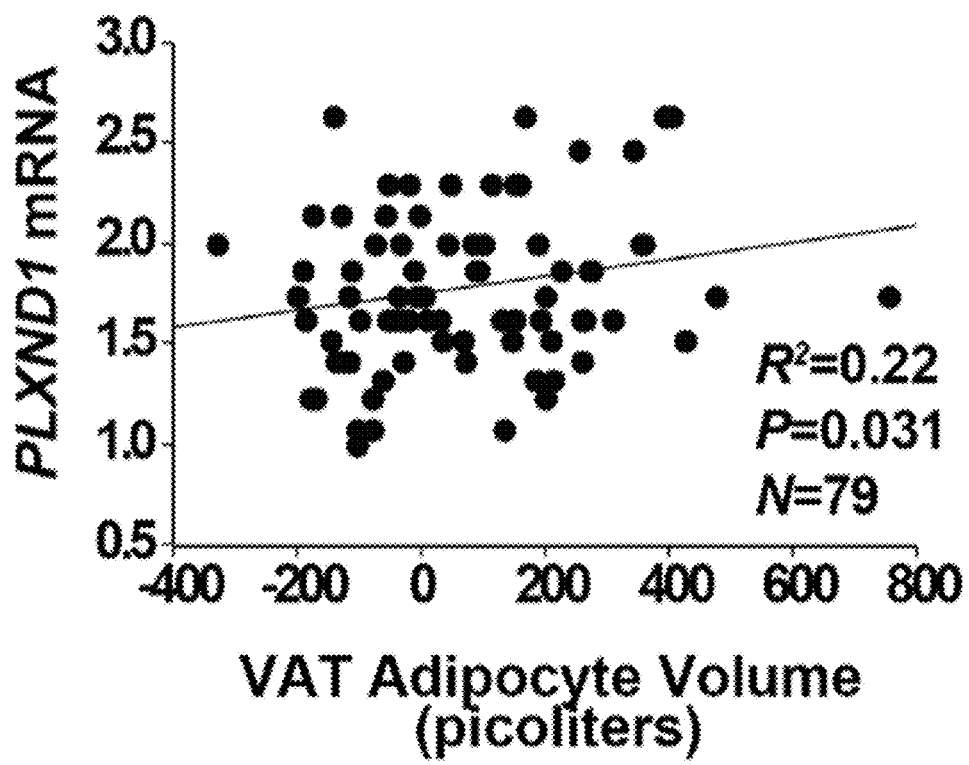
FIG. 1(F) shows a significant positive correlation was observed between VAT PLXIVD 1 mRNA and hypertrophic VAT morphology in humans.
Figure 6D:
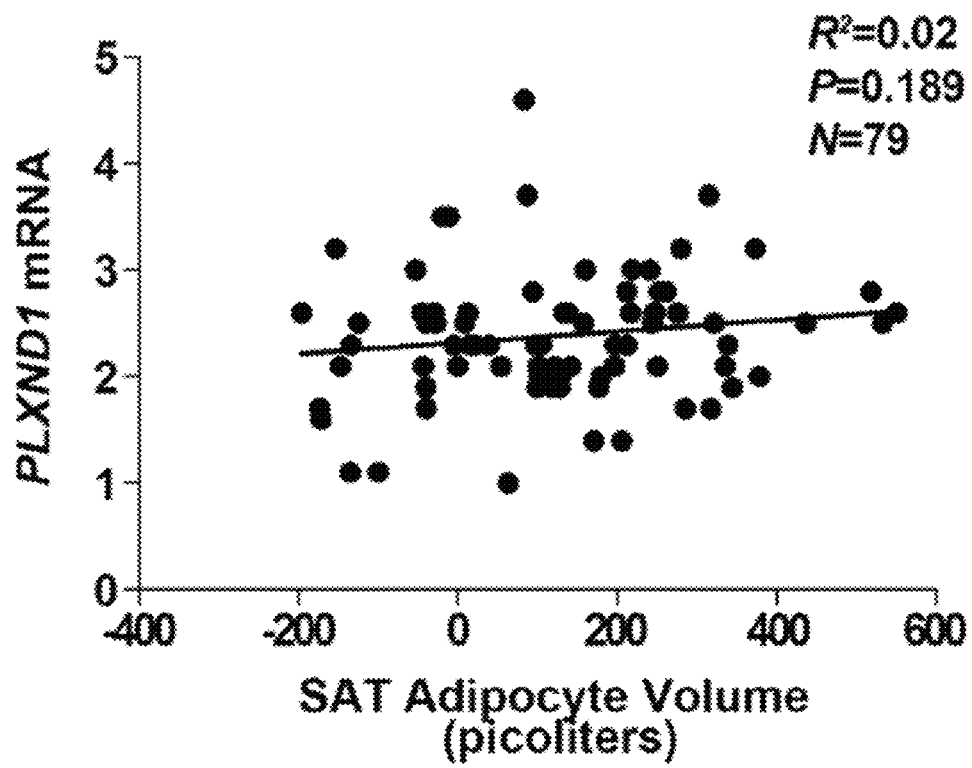
FIG. 6(D) shows no significant correlation observed in human SAT between PLXND1 and hypertrophic morphology in human SAT.

Multiple regression analysis (adjusting for age and body mass index) revealed a positive association between VAT PLXND1 mRNA and more pronounced hypertrophic morphology in VAT (R2=0.22 and P=0.031) in humans (FIG. 1(F)). Whereas, no correlation was observed between PLXND1 mRNA and morphology in SAT (FIG. 6(D)).

Example 3: ECM Dynamics in Plxnd1 Mutant Zebrafish

Figure 2A:
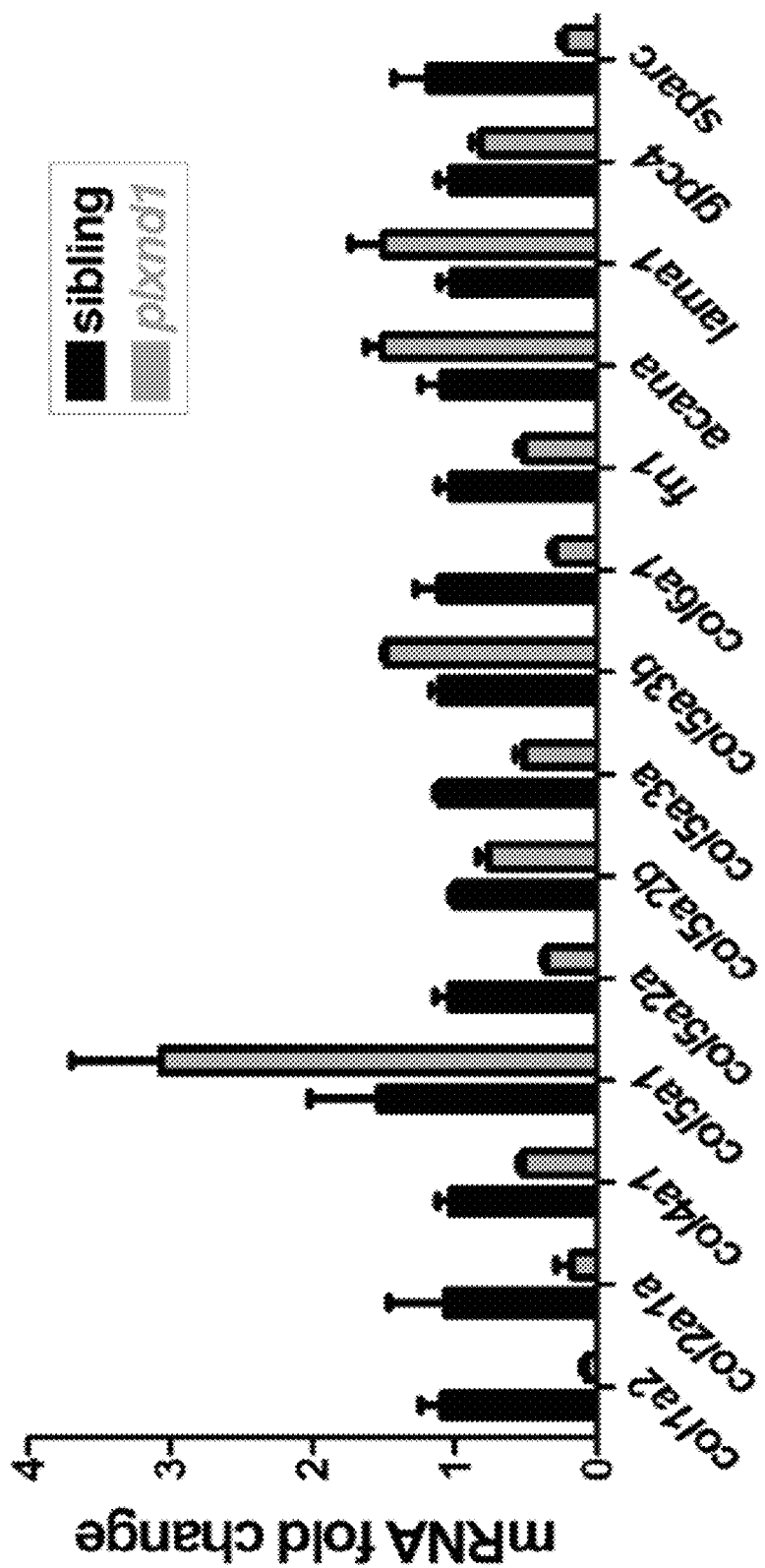
FIG. 2(A) shows qRT-PCR for ECM markers from whole zebrafish VAT. All mRNAs shown were significantly different between plxnd1 and siblings (a=0.05).

Col5a1 is Induced by Vascular Endothelial Cells of Plxnd1 Mutant Zebrafish VAT qRT-PCR revealed large-scale dysregulation of ECM components within plxnd1 mutant VAT (FIG. 2(A); see also Table 1 for qRT-PCR primers). A subset of ECM components were downregulated (FIG. 2(A)); however, the type V collagens col5a1 and col5a3b were increased (FIG. 2(A)).

Figure 2B:
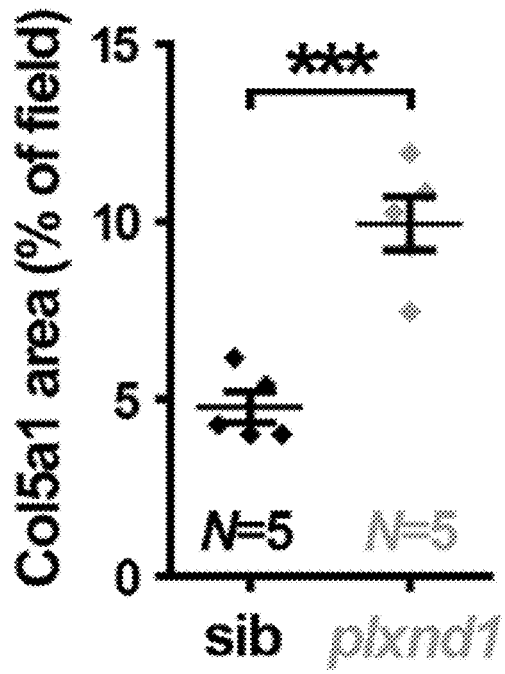
FIG. 2(B) shows quantification of Col5 area in wild-type and plxnd1 VAT as measured by confocal immunofluorescence imaging. Area is expressed as % of field of view.
Figure 2C:
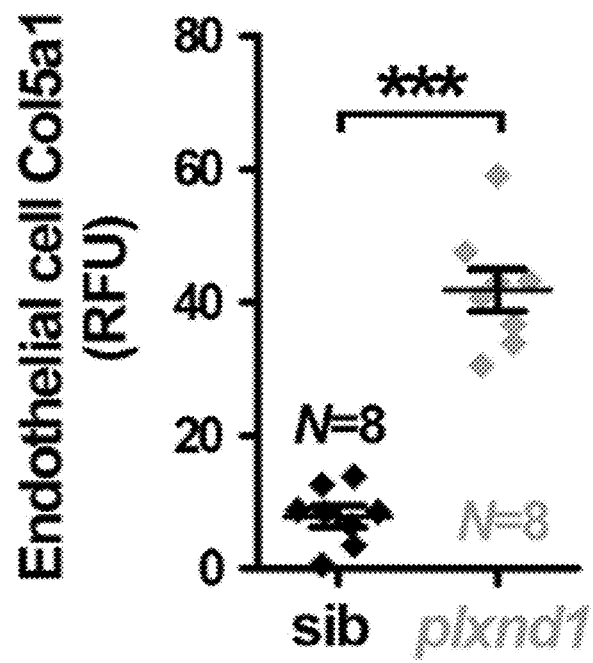
FIG. 2(C) shows quantification of Col5 signal in endothelial cells relative to background as measured by confocal immunofluorescence imaging.

Immunofluorescence confirms an increase in Col5 protein and reveals specific localization to vascular endothelial cells in plxnd1 mutant VAT (FIGS. 2(B) & 2(C)). FACS enrichment of endothelial cells followed by qRT-PCR shows that col5a1 mRNA is increased in plxnd1 mutant endothelial cells (FIG. 2(D)), supporting a vascular endothelial cell origin for Col5a1 in plxnd1 mutant VAT.

Knockdown of Col5a1 Normalizes Hyperproliferation and Hyperplastic Morphology within Plxnd1 Mutant VAT Zebrafish col5a11 was targeted with multiple, non-overlapping Vivo-Morpholinos (vMOs) (FIG. 9).

Zebrafish were raised under normal conditions until 30-50 days post fertilisation. Fish were anesthetised in 0.67 g/L MS222 and SL measured using an eyepiece reticle. Intra-abdominal injections were then performed on a Nanoject II injector (Drummond) as previously described. (McMenamin S K, et al (2013), Endocrinology 154(4):1476-1487.) At each injection, dosage was adjusted according to body weight (mg) using the following equation: mg=−48.10+ 7.36*SL+0.68*(SL-8.94)$^2$. (McMenamin S K, et al (2013), Endocrinology 154(4):1476-1487.) Concentration of individual compounds at injection were (relative to volume/ mass of fish): 80 ng/mg col5a1-ile2 vMO (5'-GAAACATG-GATGCTACAGAGAGAGA-3'; SEQ ID NO.: 55) or col5a1-e3i3 vMO (5'-GAGTTCCTACTTACCT-CAAACACCT-3'; SEQ ID NO.: 56) (Gene-Tools, LLC), 100 µM EDHB (Sigma) and 80 ng/mg EdU. Control animals were injected with either a standard control vMO (5'-CCTCTTACCTCAGTTACAATTTATA-3'; SEQ ID NO.: 57) (Gene-Tools) or 0.1% DMSO.

Figure 2D:
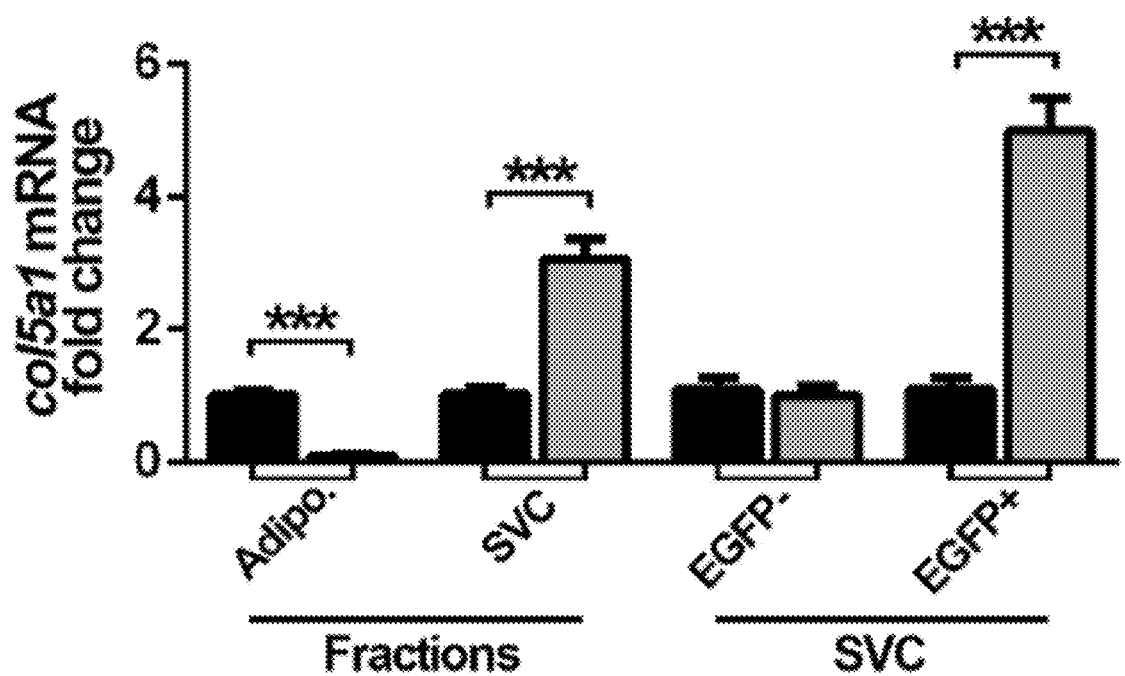
FIG. 2(D) shows qRT-PCR on adipocyte (Adipo.) and stromal vascular cell (SVC) fractions reveals col5a1 is enriched in SVCs of plxnd1 VAT. FACS enrichment of EGFP+ endothelial cells from fli1a:EGFP plxnd1 mutant and sibling VAT show that SVC-derived col5a1 is upregulated in plxnd1 endothelial cells.
Figure 9A:
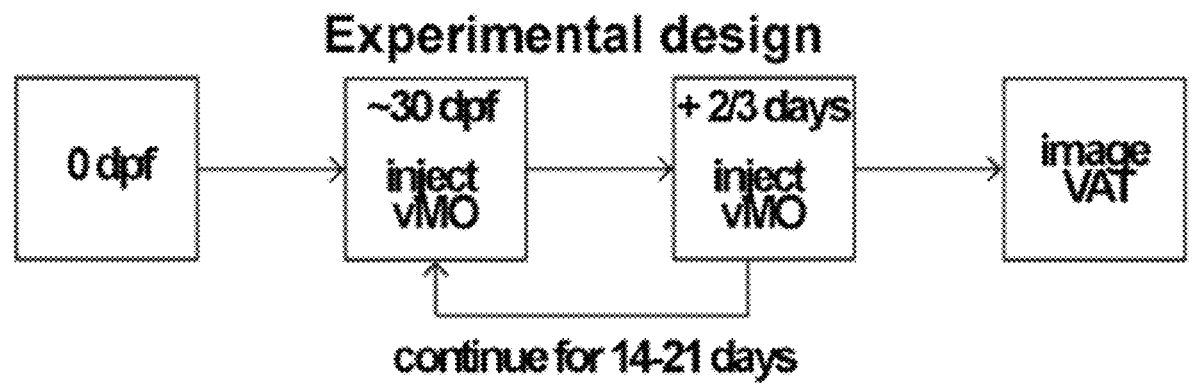
FIG. 9(A) shows a schematic depicting the experimental design of col5a1 vMO injection.
Figure 9B:
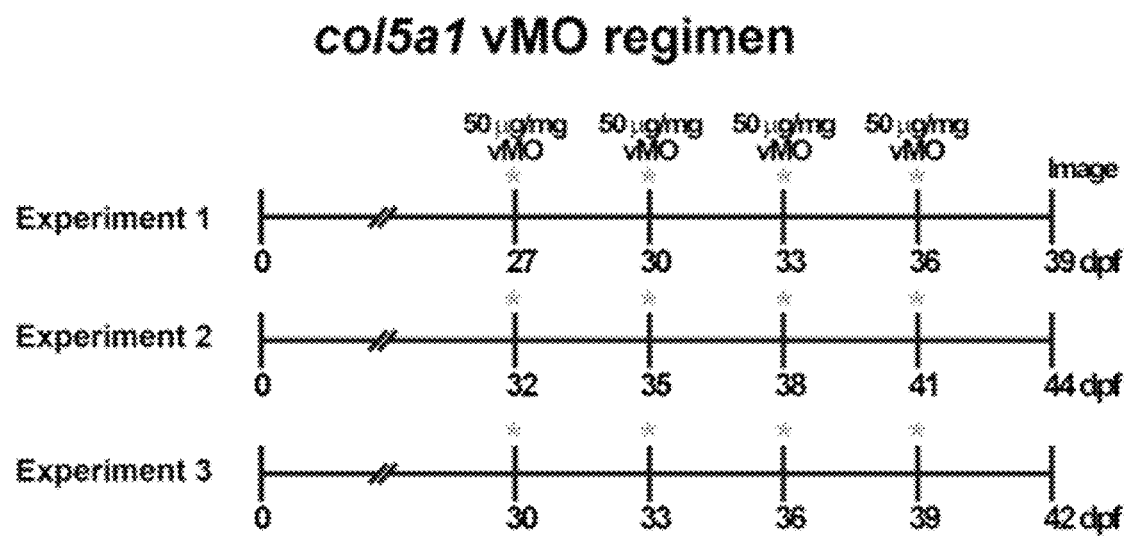
FIG. 9(B) shows a schematic depicting the col5a1 vMO injection regimens. Regimens were performed with two different col5a1 vMOs.
Figure 9C:
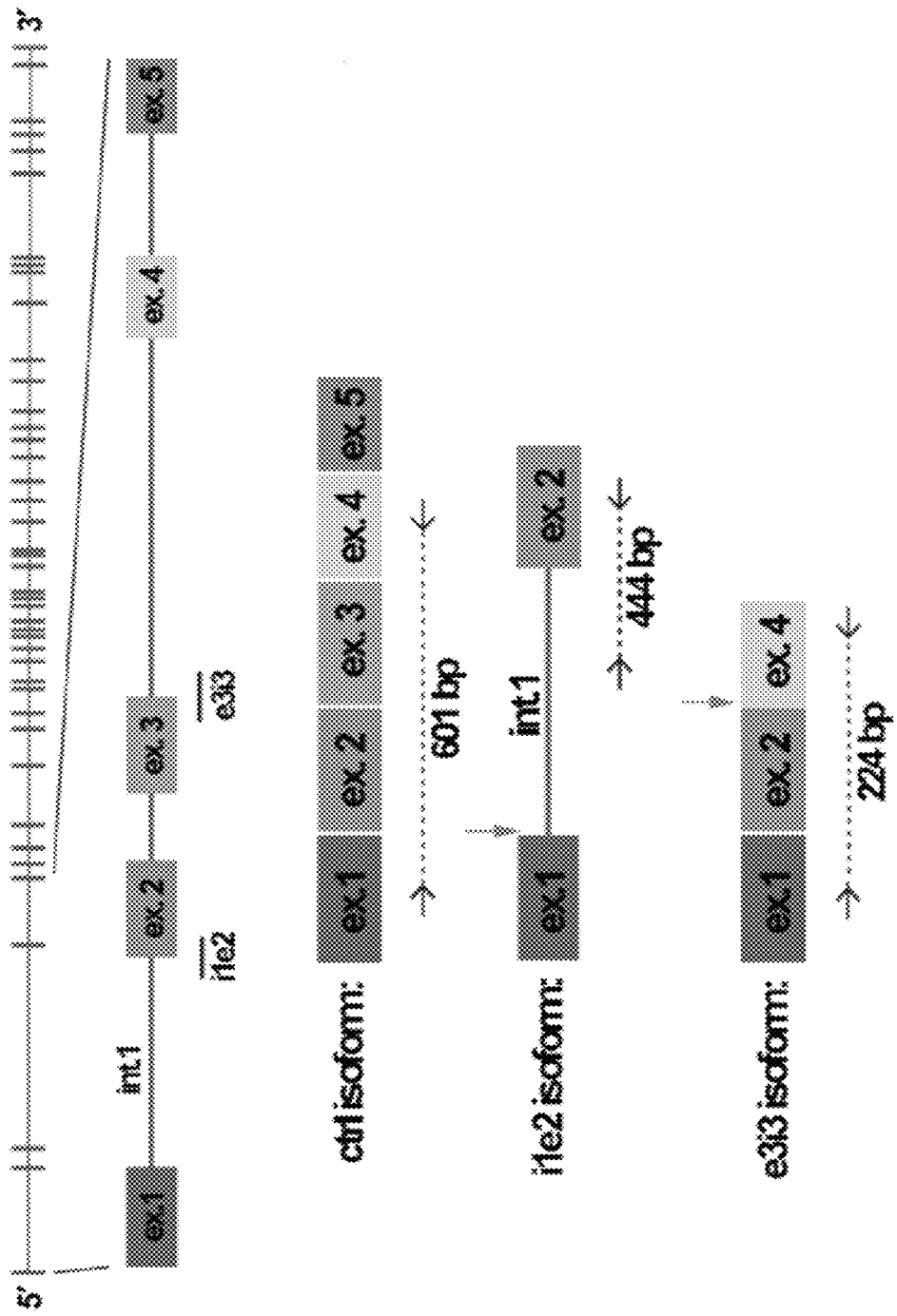
FIG. 9(C) shows a schematic depicting zebrafish col5a1 gene structure. vMOs were designed to target the intron 1-exon 2 (ile2) and exon 3-intron 3 (e3i3) boundaries. Observed isoforms are schematised below the gene structure. A predicted stop codon was found at the immediate start of intron 1 for the col5a1-ile2 isoform leading to a truncated 55 amino acid col5a1 containing only exon 1 and a partial Concanavelin-A like lectin and Laminin G domains. For the col5a1-e3i3 isoform, a premature stop codon was found at the start of exon 4 producing a 112 amino acid col5a1 containing a truncated Concanavelin-A like lectin and Laminin G domains. Arrows indicate the location of premature stop codons. Locations of PCR primers used to determine isoform structure are shown and sequences are given in Table 1. Expected product sizes are 601 bp for control (ctrl) col5a1 isoform, 444 bp for col5a1-ile2 and 224 bp for col5a1-e3i3. Isoforms were confirmed by sequencing.
Figure 9D:
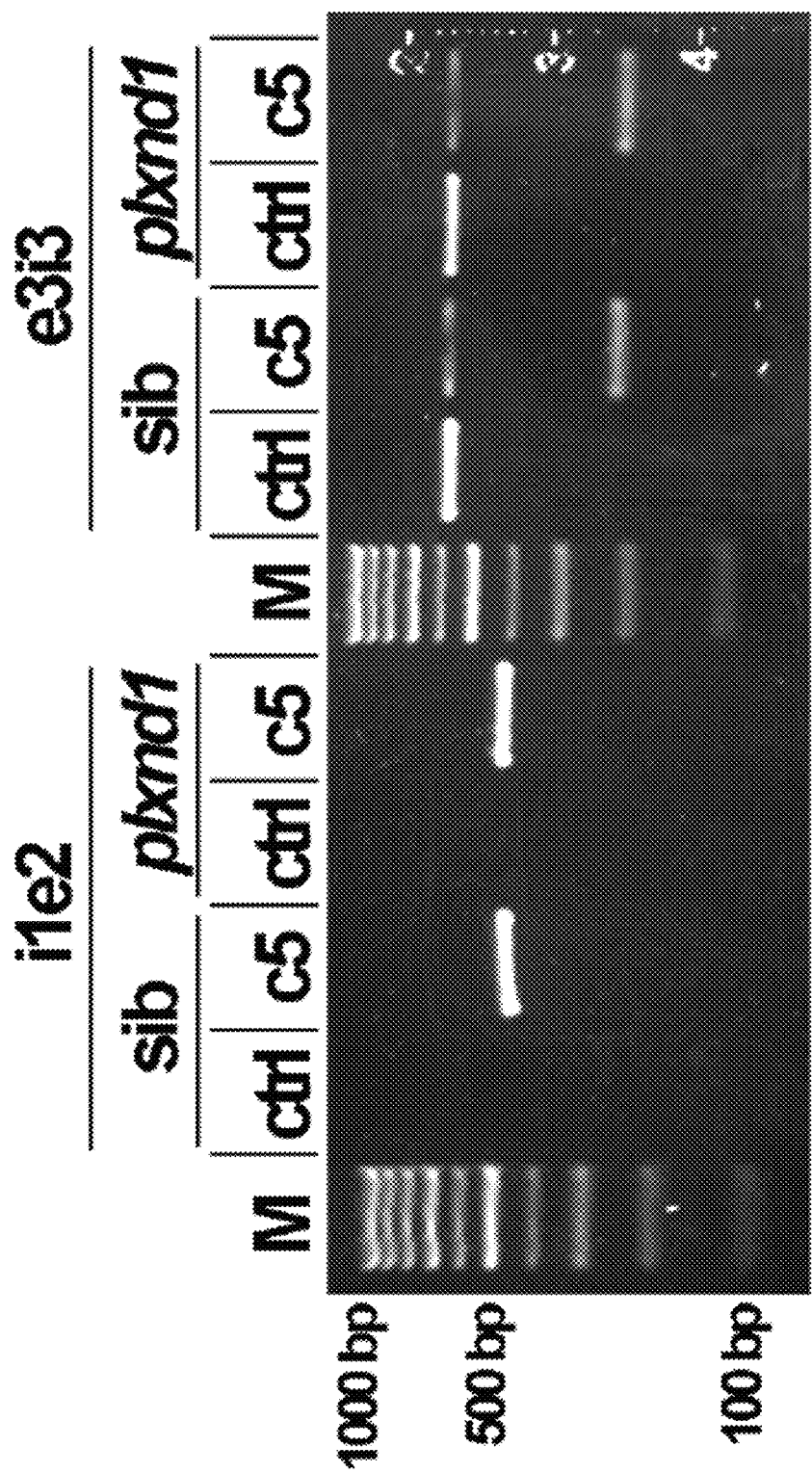
FIG. 9(D) shows RT-PCR depicting the inclusion of part of intron 1 after injection of col5a1-ile2, and the skipping of exon 3 after injection of col5a1-e3i3. M=marker (100-1000 bp in 100 bp increments). The induced col5a1 mRNA isoforms are predicted to lead to a reduction in col5a1 function based on previous published literature. (Marchant J K, Hahn R A, Linsenmayer T F, & Birk D E (1996), The Journal of cell biology 135(5):1415-1426.)
Figure 10:
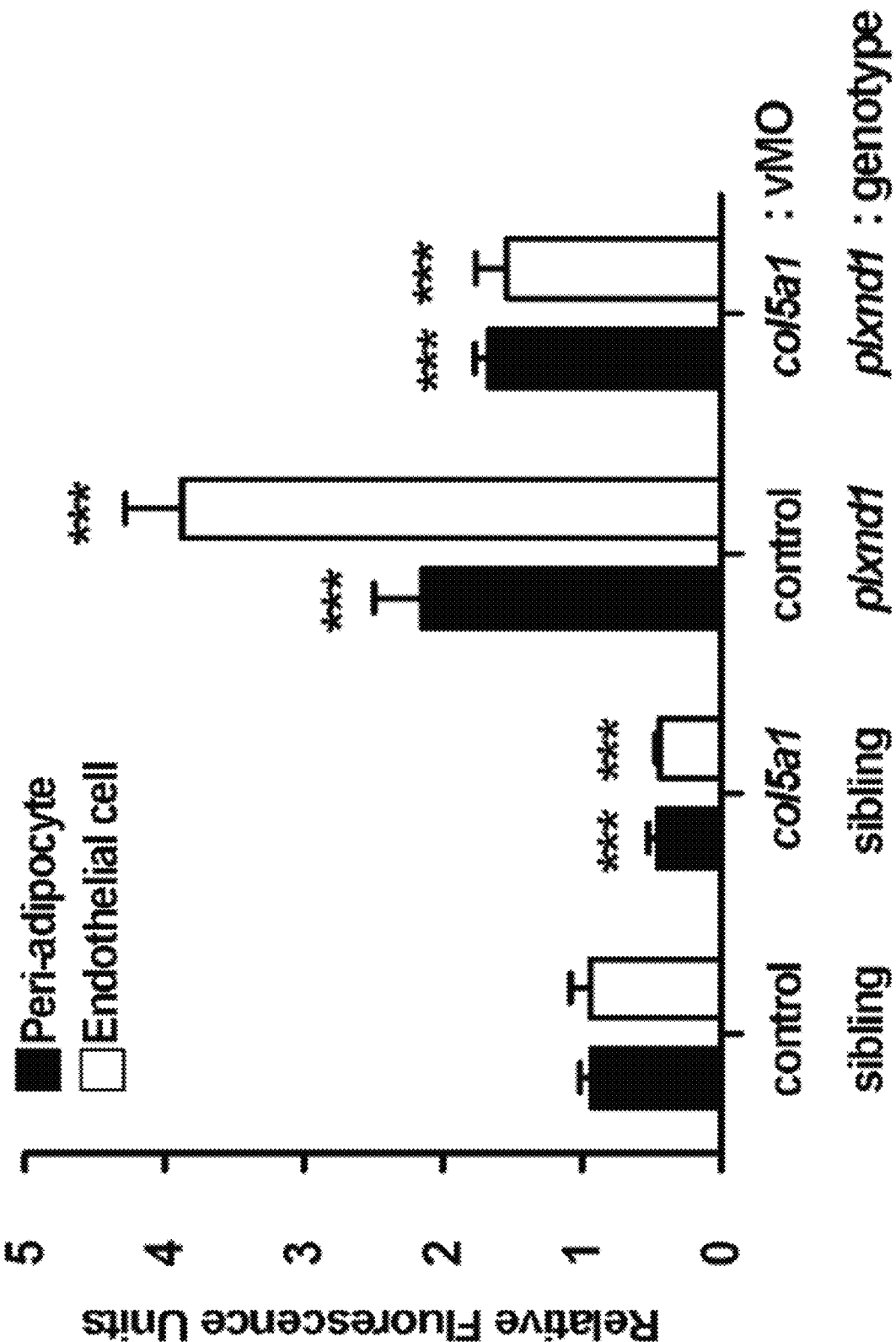
FIG. 10 shows Col5 reactivity is reduced after injection of col5a1 vMOs. Maximum intensity projections of immunofluorescently labelled Col5 in VAT were quantified relative to background in both endothelial cell and peri-adipocyte locations with or without col5a1 vMOs in for the indicated genotypes.

Serial injection of either vMO disrupted splicing of col5a1, and RT-PCR followed by sequencing confirmed the production of truncated col5a1 mRNAs predicted to be nonfunctional (cola5a1-ile2, 55 amino acid; col51-e3i3, 112 amino acid) (FIGS. 9(C) & 9(D)). Assessment of Col5 reactivity after injection of col5a1-ile2 vMO revealed significantly reduced Col5 protein levels in both endothelial cell and peri-adipocyte locations (FIG. 10). Injection of either col5a1 vMO did not affect proliferation or morphology of sibling VAT (FIGS. 2(E) & 2(F)). However, in hyperplastic plxnd1 mutant VAT, injection of col5a1 vMO increased LD hypertrophy and induced the appearance of an additional population of very large LDs (µ3=122.59 pm; FIG. 2(D)). Further, col5a1 vMO normalized levels of EdU+ nuclei in plxnd1 mutant VAT (FIG. 2(F)), and volumetric analysis revealed a partial rescue of lipid storage in plxnd1 mutant VAT (FIG. 2(G)), and increasing VAT:SAT ratio (FIG. 2(H)).

Figure 3A:
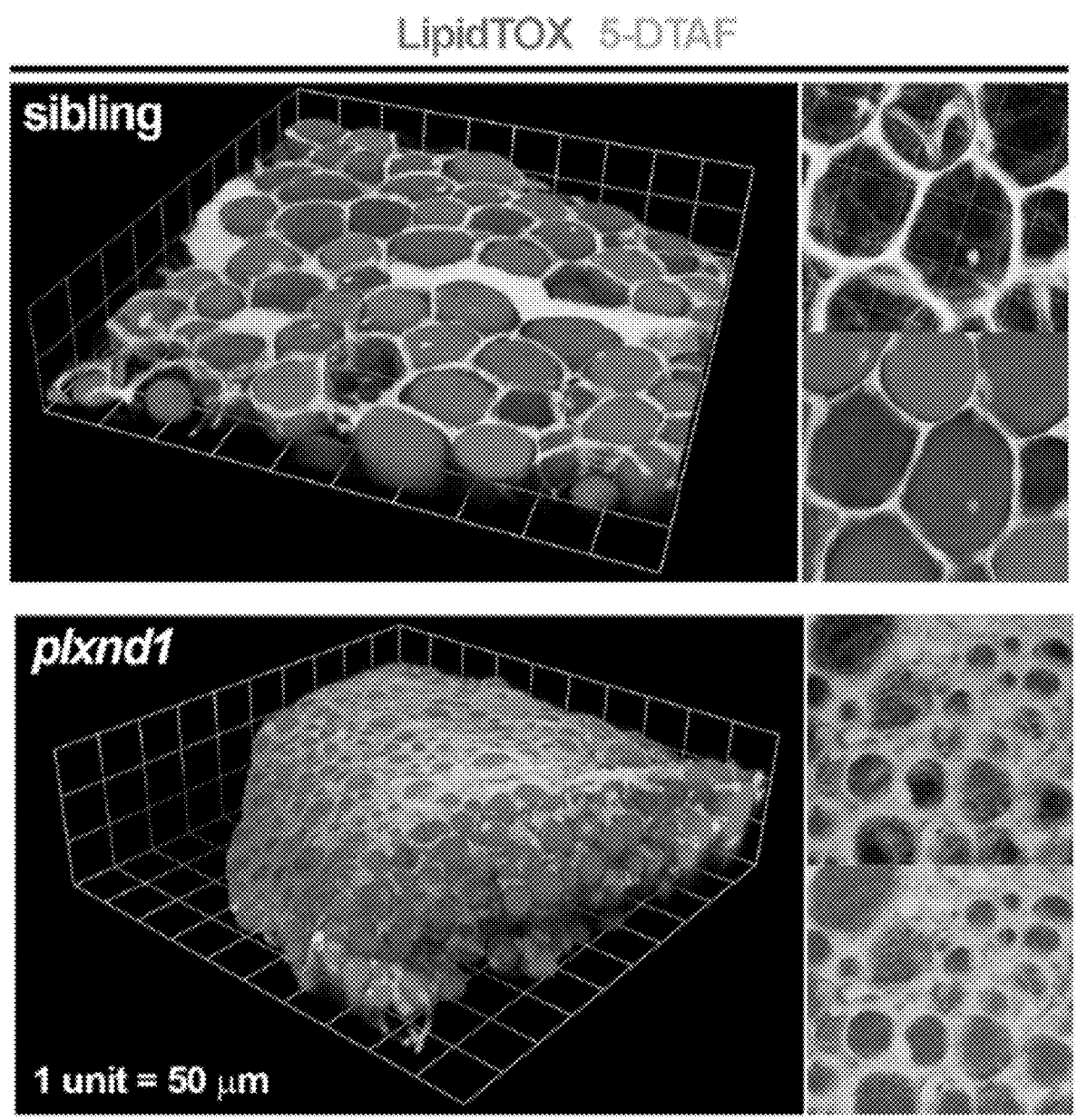
FIG. 3(A) shows 3D renderings of sibling or plxnd1 mutant VAT stained with LipidTOX (lipid droplets, dark grey/black) and 5-DTAF (collagen, light grey/white).
Figures 11A, 11B:
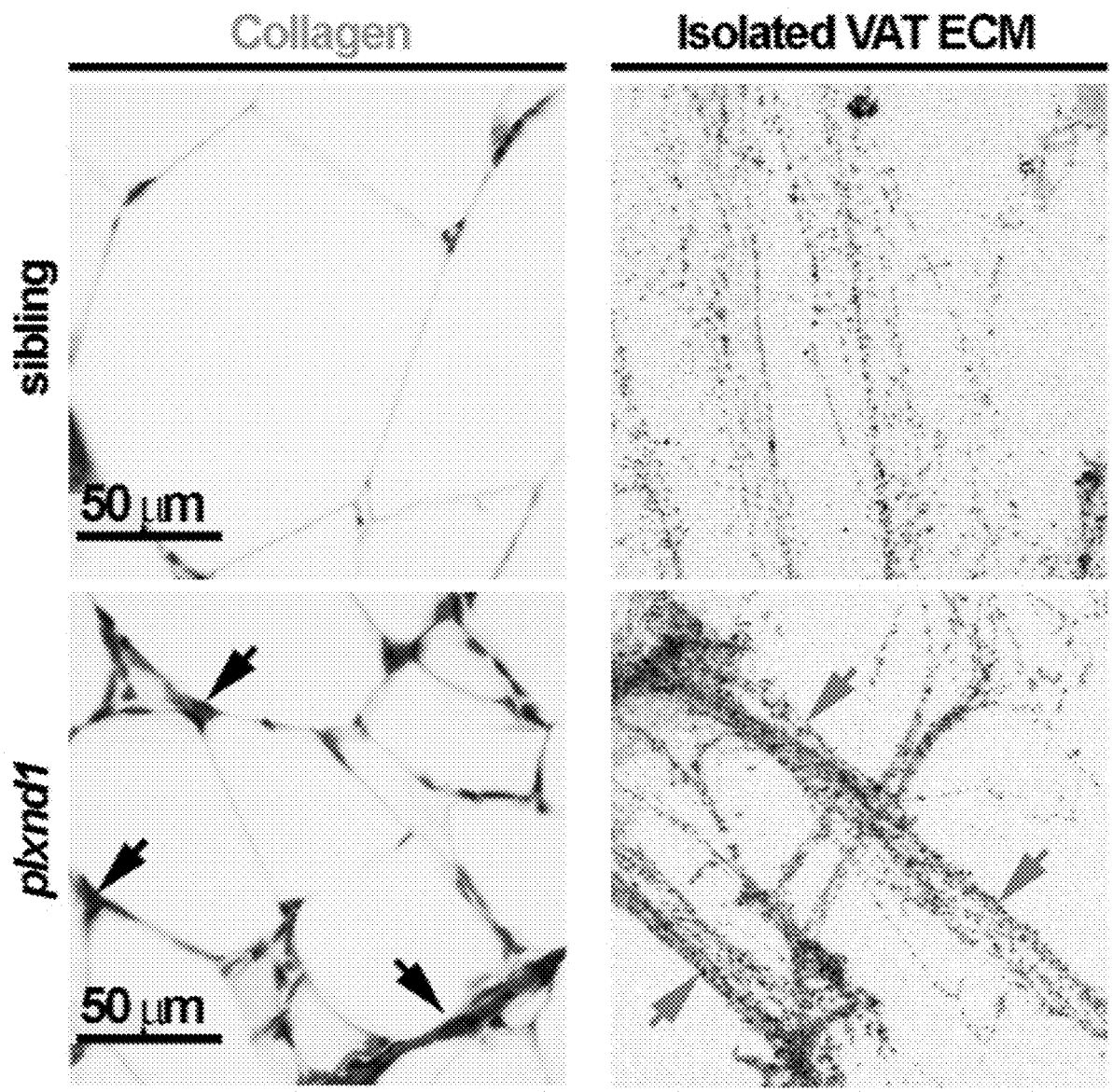
FIG. 11(A) shows Masson's trichrome staining (collagen, dark stain, arrows) is increased in VAT of plxnd1 mutants.
FIG. 11(B) shows isolated ECM from plxnd1 VAT and stained with 5-DTAF exhibits increased fibrous structures. Arrows indicate the increased diameter of plxnd1 fibers.
Figure 11D:
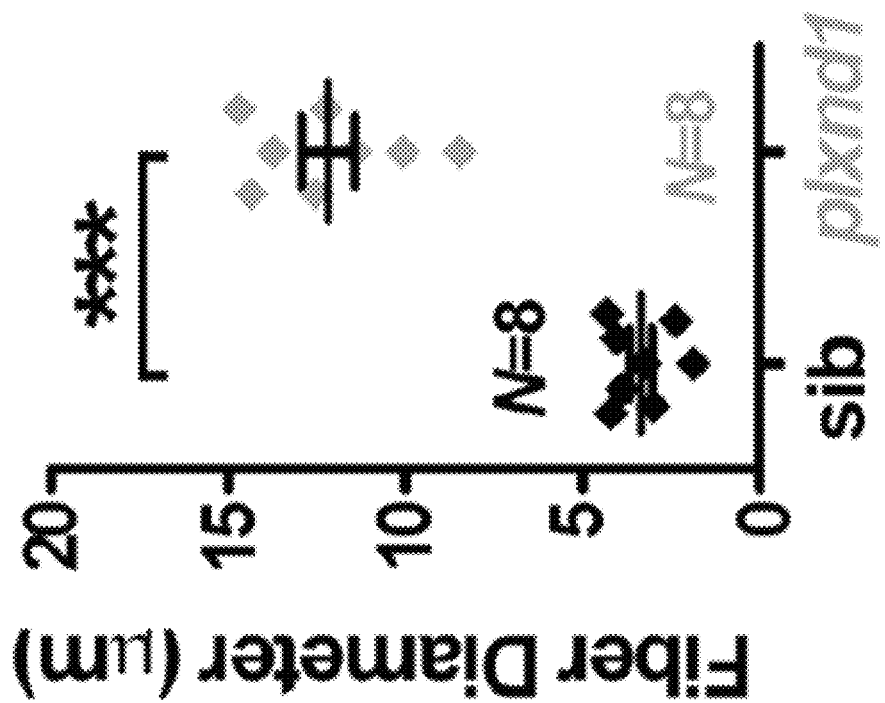
FIG. 11(D) shows mean fiber diameter. Measurements were taken on maximum intensity projects of 5-DTAF stained isolated ECM.
Figure 11C:
FIG. 11(C) shows % collagen area. Measurements were taken on Masson's trichrome stained sections, and area is expressed as % of total field.
Figures 12A, 12B, 12C:
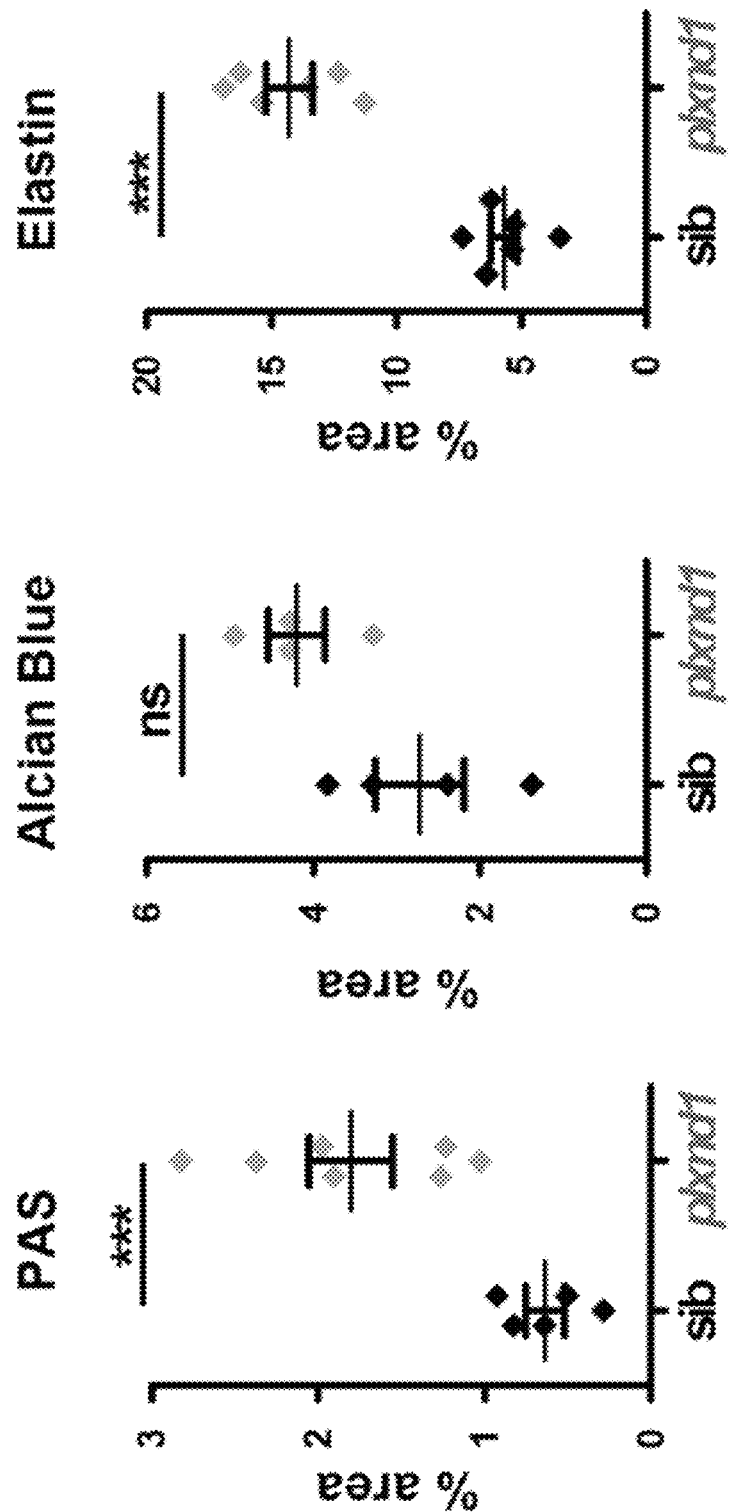
FIG. 12(A) shows quantification of the area of Periodic acid Schiff (PAS) stained VAT in wild type (sib) and plxnd1 strains.
FIG. 12(B) shows quantification of the area of Alcian blue stained VAT in wild type (sib) and plxnd1 zebrafish.
FIG. 12(C) shows quantification of the area of Elastin stained VAT in wild type (sib) and plxnd1 zebrafish.
Figure 12D:
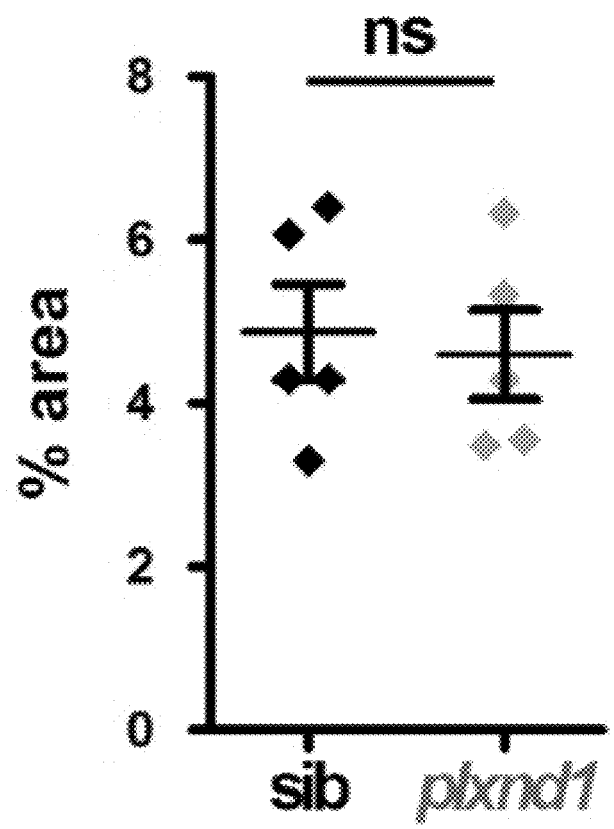
FIG. 12(D) shows quantification of collagen stained SAT (Masson's trichrome histology) in wild type (sib) and plxnd1 zebrafish.

Plxnd1 Mutant VAT Undergoes Augmented Fibrillogenesis in a Col5a1-Dependent Manner The fluorescent collagen probe 5-(4,6-Dichlorotriazinyl) Aminofluorescein (5-DTAF) labels VAT-localized collagen fibers to reveal the architectural properties of ECM. (Lackey D E, et al. (2014), American journal of physiology. Endocrinology and metabolism 306(3):E233-246.) The ECM architecture of plxnd1 mutant VAT was markedly different from sibling VAT (FIG. 3(A)), and characterised by larger and more numerous interstitial collagen fibers (FIG. 3(A), FIG. 11). Moreover, plxnd1 mutant VAT had increased glycoprotein, Elastin content (FIG. 12(C)) and a greater abundance of fibrous ECM (FIG. 12). plxnd1 mutant SAT did not have altered collagen or fibrous ECM (FIG. 12(D)).

Figure 3B:
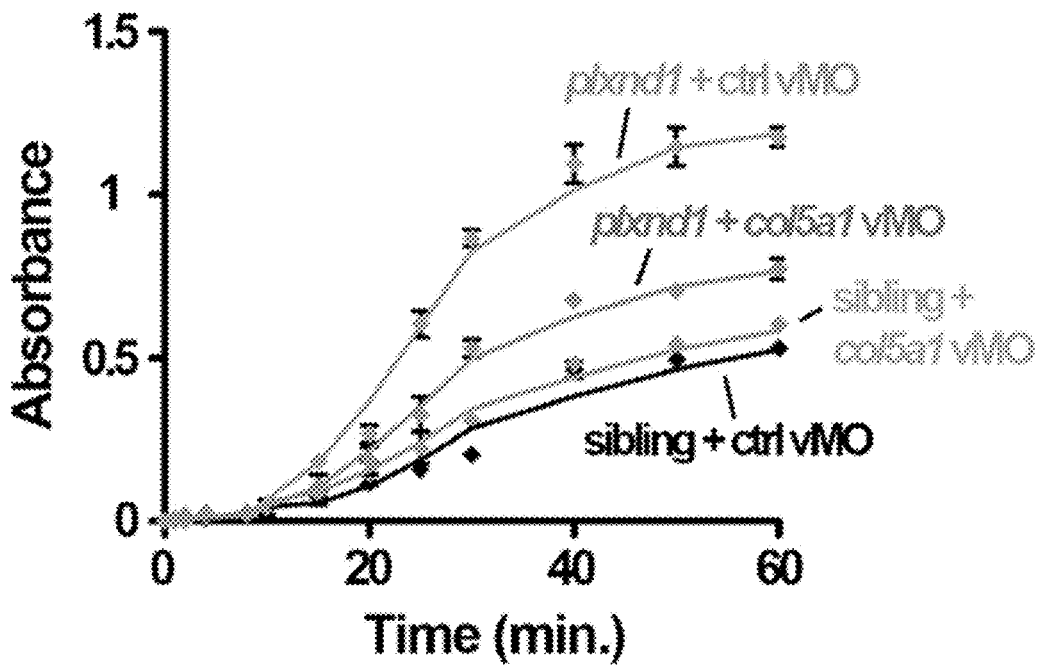
FIGS. 3(B) & 3(C) show turbidity assays using ECM extracted from zebrafish VAT and induced polymerization and gel formation in vitro. These results reveal a Col5a1-dependent increase in FIG. 3(B) the rate of fibrillogenesis, and 3(C) greater ultimate turbidity suggesting increased collagen fibrils within plxnd1 VAT.
Figure 3C:
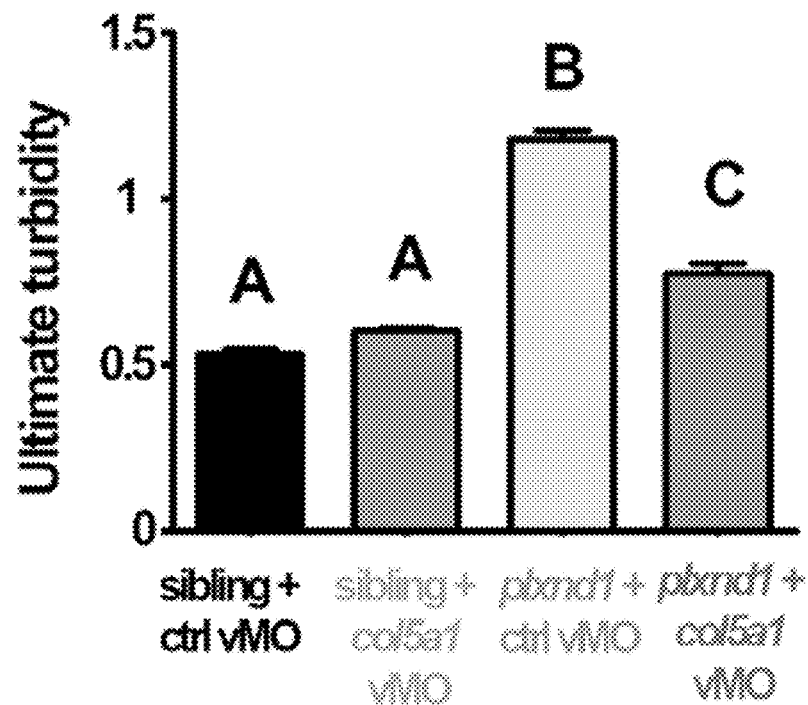
Figure 13A:
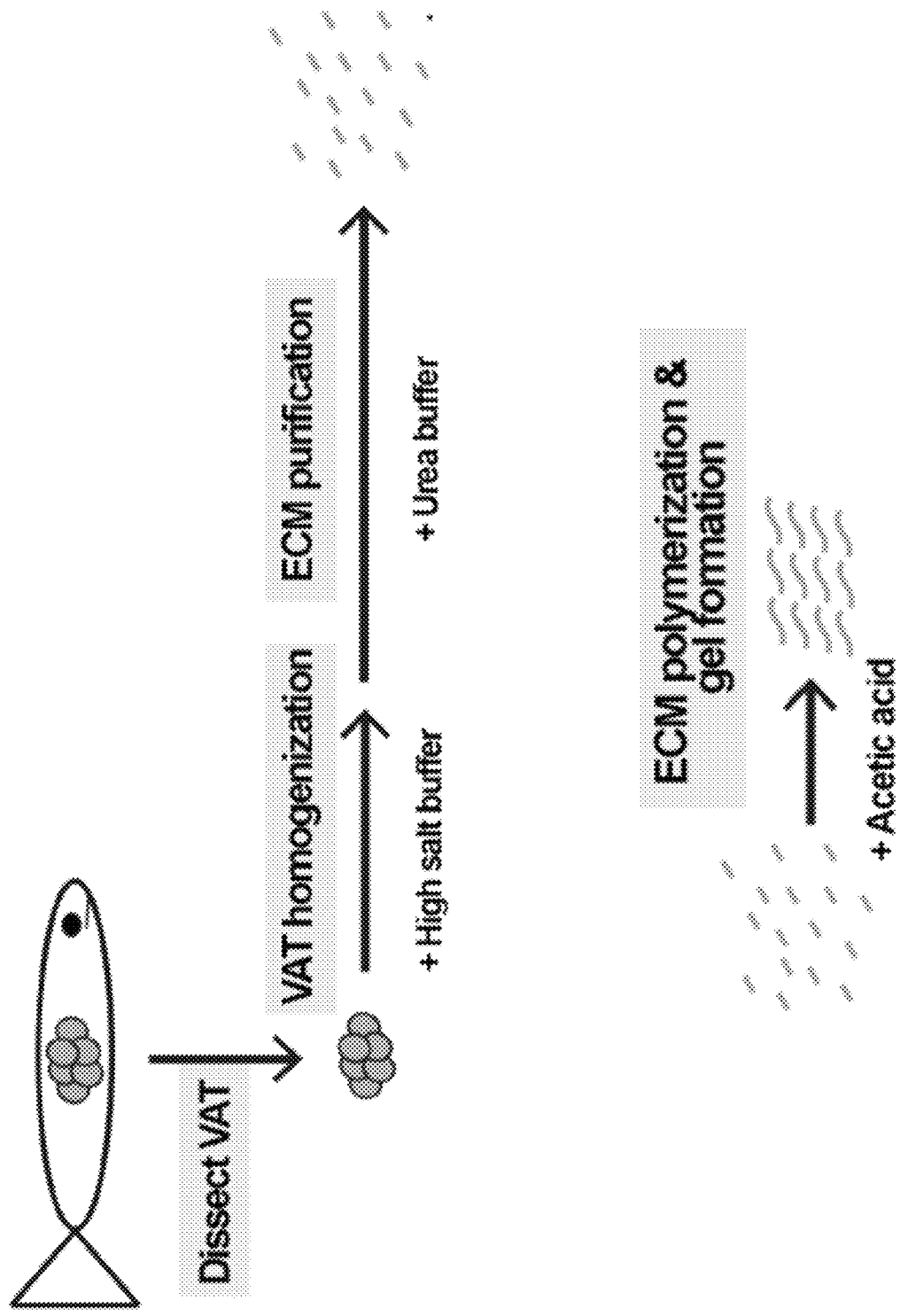
FIG. 13(A) shows a schematic illustrating the process of ECM extraction from VAT.

To assess fibrillogenesis in plxnd1 mutant VAT, ECM is extracted from zebrafish VAT, and fibril polymerization and gel formation is induced in vitro (FIG. 13). Turbidity assays are used to determine the rate and ultimate extent of fibrillogenesis. ECM was purified from dissected zebrafish VAT (~100 VATS per tube, triplicate tubes per condition) as previously described. (Uriel S, et al. (2009), Tissue engineering. Part C, Methods 15(3):309-321.) Urea extraction was allowed to proceed for 14-21 days at 4° C. Protein concentration (~7 mg/ml) was assessed by the Bradford assay (Thermo Scientific). Protein concentrations were not significantly different between groups. To induce fibril polymerization and gel formation, acetic acid was added to a pH of 7. Turbidity assays were conducted as previously described using a Spectronic 20D+ spectrometer (Thermo Scientific). (Wood G C & Keech M K (1960), The Biochemical journal 75:588-598.)

plxnd1-deficient VAT underwent an increased rate of fibrillogenesis compared to sibling ECM (FIG. 3(B)), and plxnd1 mutant VAT attained a higher ultimate turbidity than sibling VAT (FIG. 3(C)). Injection of col5a1-ile2 vMO did not affect in vitro fibrillogenesis of sibling VAT; however, col5a1 vMO injection significantly reduced both the rate of fibrillogenesis and turbidity in plxnd1 mutant VAT (FIGS. 3(B) & 2(C)).

Figure 3D:
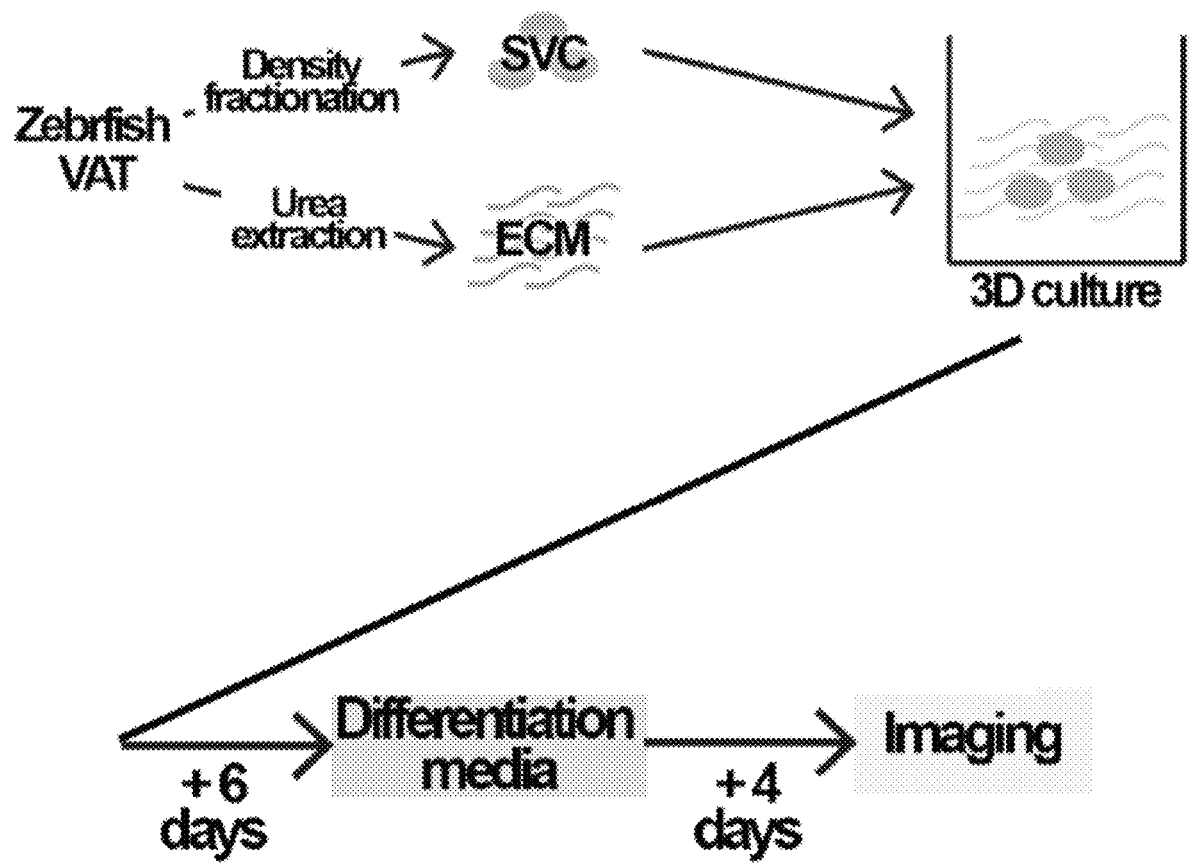
FIG. 3(D) shows a schematic of ECM and SVC 3D co-culture experimental design. Briefly, ECM and SVCs were isolated from either sibling or plxnd1 mutant VAT. The isolated ECM was then used as a 3D substrate for SVC culture.

Plxnd1 Mutant ECM is Sufficient to Induce Hyperproliferation and Hyperplastic Morphology of SVCs In Vitro Isolated ECM from zebrafish VAT was used as a substrate for the culture of primary stromal vascular cells (SVCs) also isolated from zebrafish VAT (FIG. 3(D)). Isolation of SVCs was conducted largely as described previously (~50 VATs per tube, triplicate tubes per condition) (Bouraoui L, et al. (2008), The Journal of endocrinology 198(3):459-469), except collagenase incubation was undertaken at 28.5° C. and the cell suspension was passed through a 70 m cell strainer. Zebrafish SVCs were counted using a hemocytometer and resuspended in actively polymerizing ECM at 5×10$^5$ cells/ml. Prior to addition of SVCs, purified zebrafish VAT ECM was diluted to 4 mg/ml. 100 µl of ECM gel and SVCs were used per well of a 96-well plate. The 3D co-culture was maintained in DMEM growth media (Sigma, #D5796) containing 10% FBS, 2 mM L-glutamine, 10 mM TIEPES as described (Bouraoui L, et al. (2008), The Journal of endocrinology 198(3):459469) for 6 days at 28.5° C./5% $CO_2$ with the addition of Pen/Strep (5K/5K) (Cambrex, #17-603E), 10 mg/ml Gentamycin (Sigma, #G1272) and 250 µg/ml Fungizone (Fisher, #BP928-250). Media was changed daily. After 6 days, media was changed to differentiation media-growth media supplemented with 0.2 mg/ml human recombinant Insulin (Sigma, #I2643), 1 M 3-isobutyl-1-methylxanthine (Sigma, #I5879), 250 µM dexamethasone (Sigma, #D4902), 45 µg/ml cholesterol (Sigma, #C8667), 100 µg/ml cod liver oil (Sigma, #C5650), 250 µg/ml polyoxyethylene sorbitan monooleate (Sigma, #P8074) and 20 µg/ml D-a-tocopherol acetate (Sigma, #T3634). Cultures were maintained in differentiation media for 4 days before fixing in 4% paraformaldehyde followed by brightfield or confocal imaging. Culture confluency was measured by thresholding brightfield images of whole wells based on pixel intensity, and LD sizes were measured as described above.

Figure 3F:
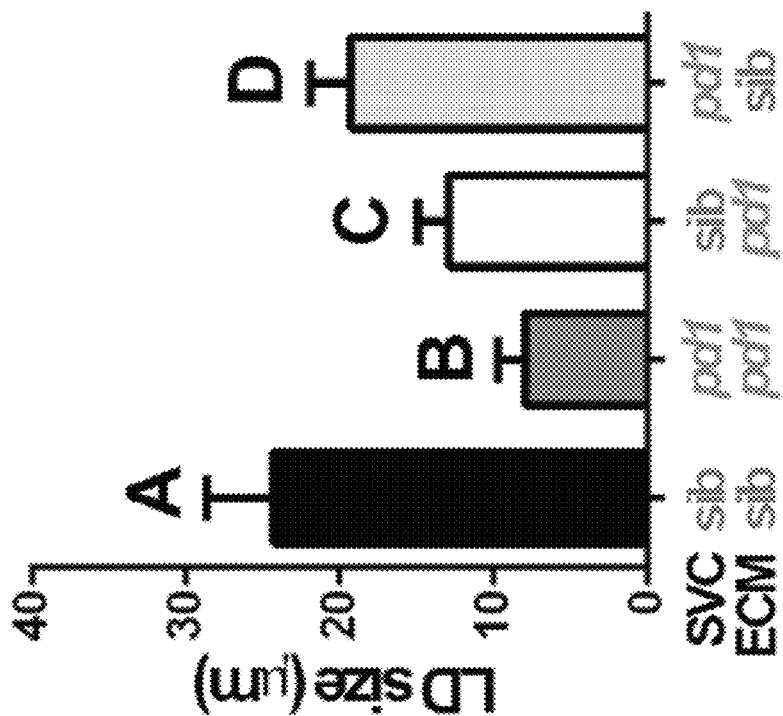
FIG. 3(F) shows mean LD size of 3D cultures for the conditions described for 3(F). LD sizes were normally distributed.
Figure 3E:
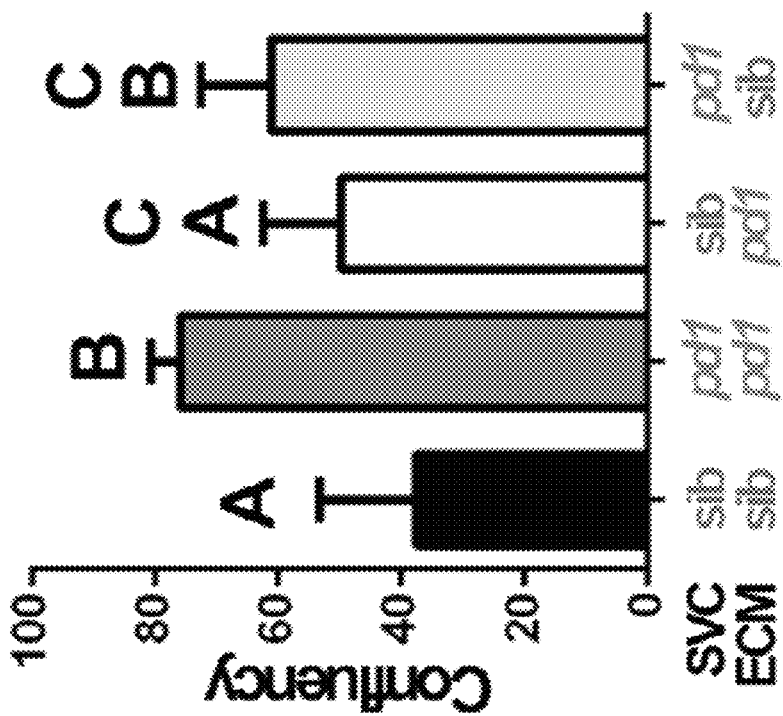
FIG. 3(E) shows confluency (% of field occupied by cells) of adipogenic clusters after 10 days of SVC 3D co-culture. SVCs were isolated from either sibling or plxnd1 VAT and used to seed either sibling or plxnd1 ECM gels (indicated on the x-axis).
Figure 14A:
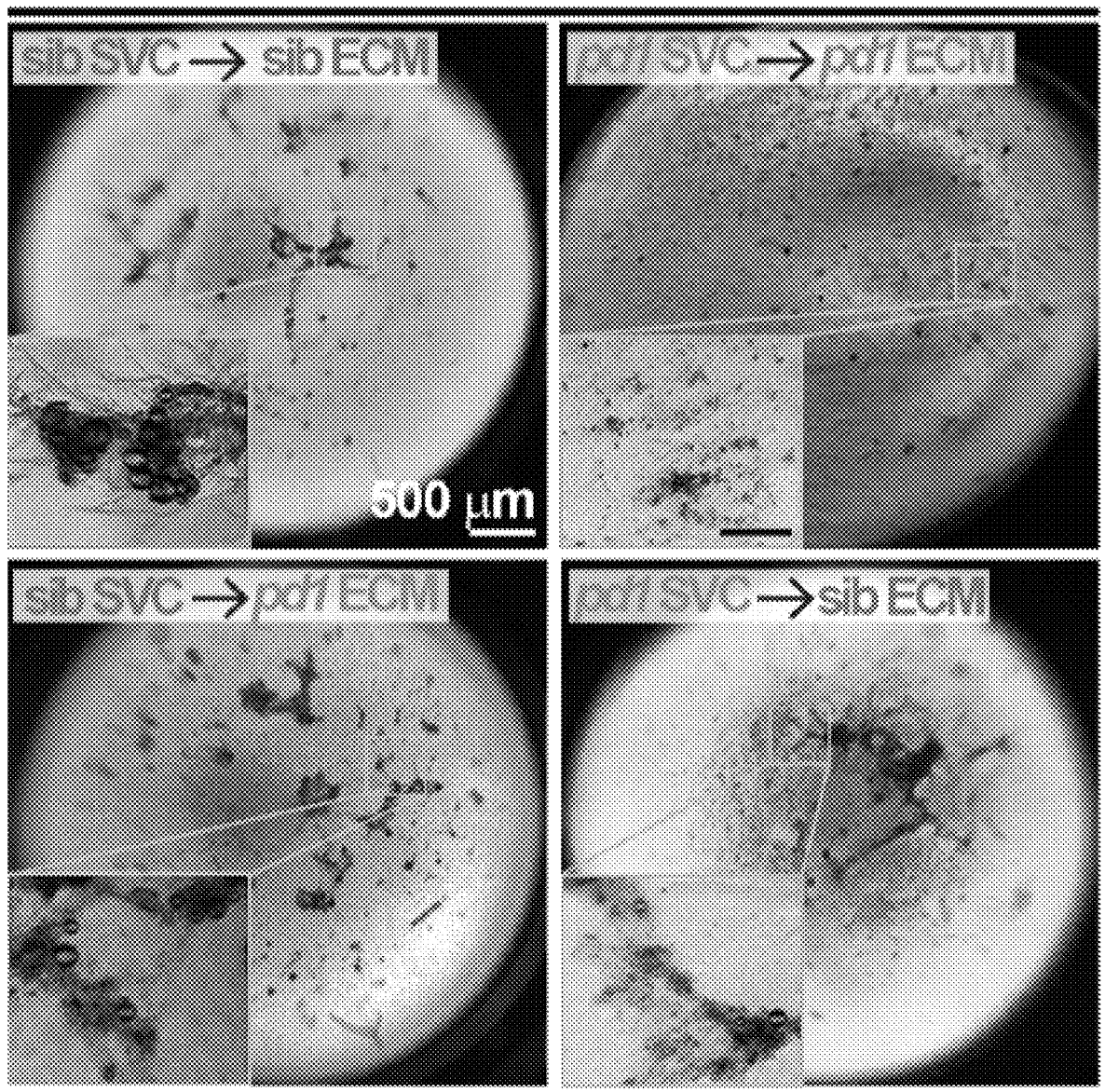
FIG. 14(A) shows brightfield images of representative 3D cultures after 10 days of culture.
Figure 14C:
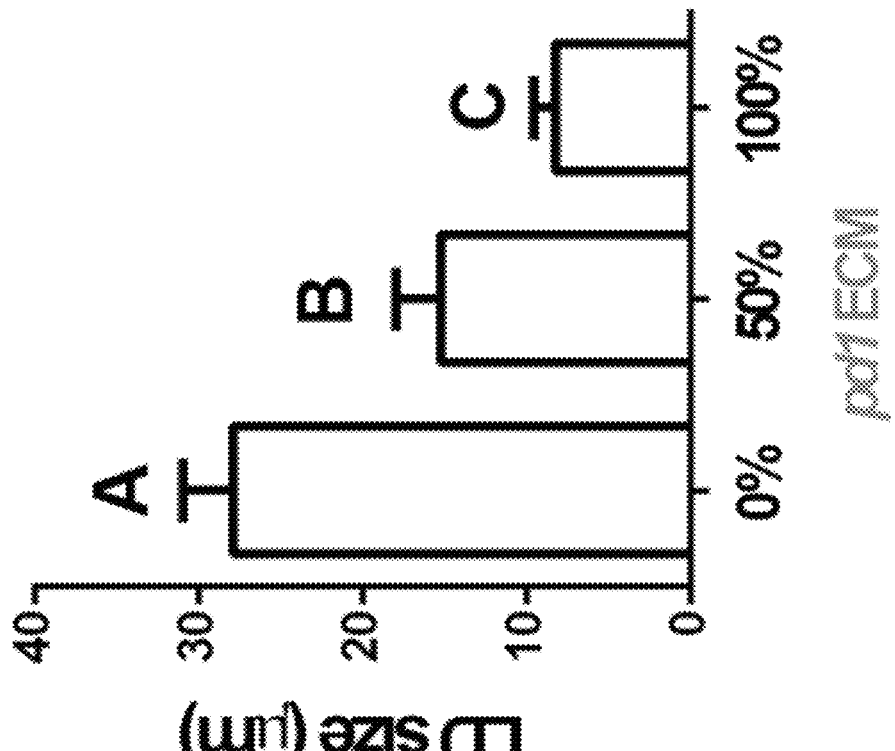
FIG. 14(C) shows mean LD size within cultures after 10 days of incubation.
Figure 14B:
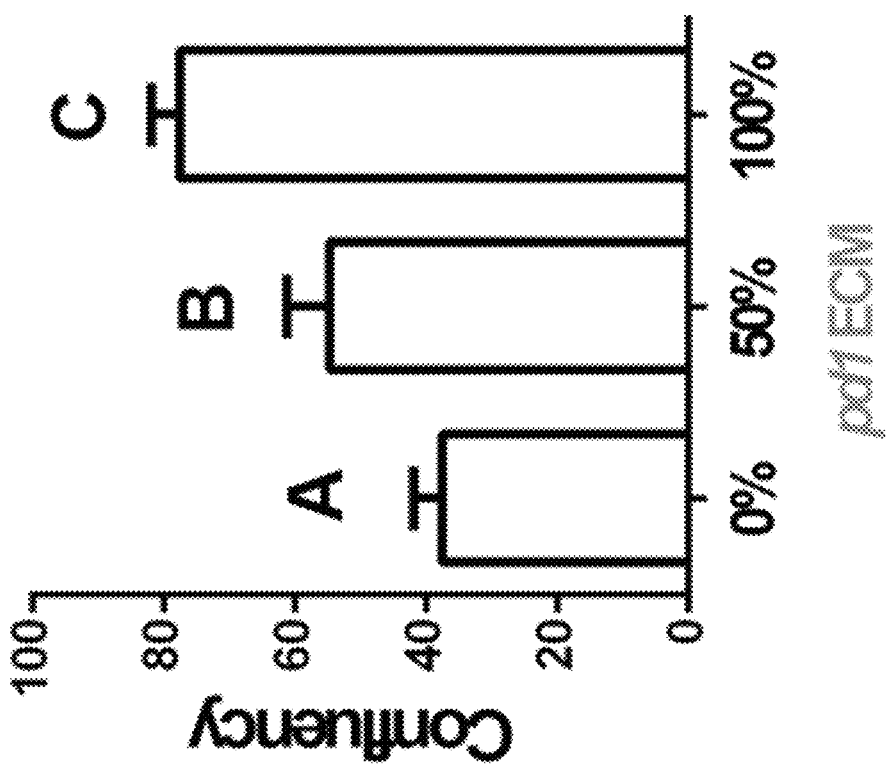
FIG. 14(B) shows confluency of cultures after 10 days of incubation.
Figure 14E:
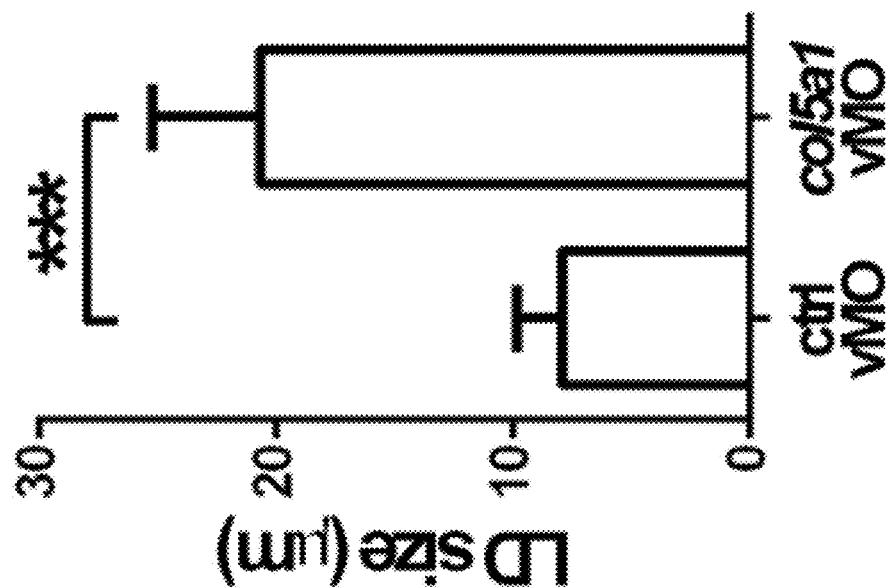
FIG. 14(E) shows mean LD size within cultures after 10 days of incubation. Cultures were from plxnd1-derived SVCs cultured with either plxnd1+control vMO (ctrl) or col5a1 vMO (col5a1).
Figure 14D:
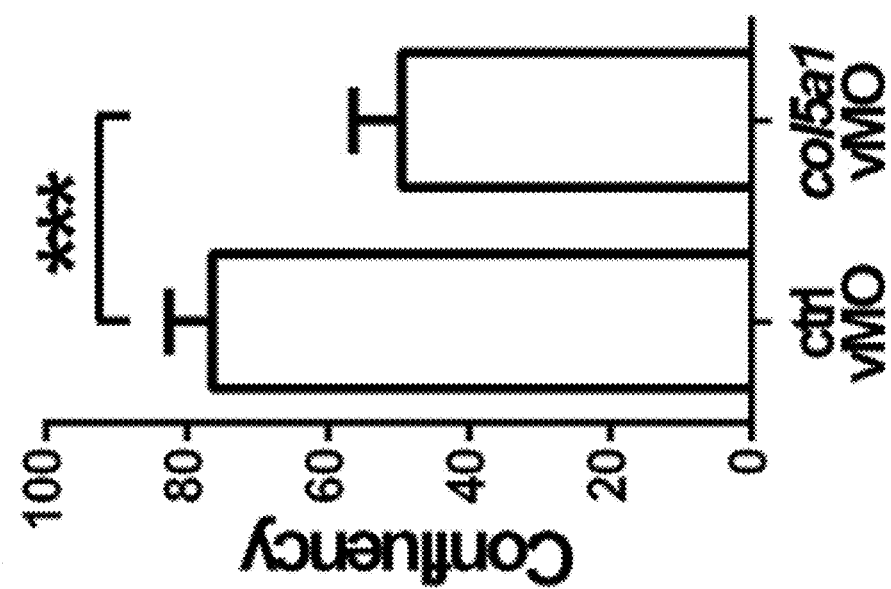
FIG. 14(D) shows confluency of cultures after 10 days of incubation. Cultures were from plxnd1-derived SVCs cultured with either plxnd1+control vMO (ctrl) or col5a1 vMO (col5a1).

When cultured within a 3D ECM substrate obtained from sibling VAT, sibling SVCs were able to proliferate and readily differentiate into adipocytes containing large LDs (FIG. 3(F)). By contrast, plxnd1 mutant SVCs cultured on ECM derived from plxnd1 mutant ECM reached a higher level of confluency (FIGS. 3(E), 3(F) and SI Appendix, Fig. S13(A) together with strikingly smaller LDs (FIG. 3(G) and FIG. 14(A)). The degree of confluency and LD hypertrophy were ECM extract dependent, as culturing sibling SVCs within ECM from plxnd1 mutants increased confluency and reduced LD size (FIGS. 3(E) & 3(F)). Conversely, culturing plxnd1 mutant SVCs in sibling ECM abrogated the hyperproliferation and smaller LD size observed in the mutant experiment, leading to larger LDs more reminiscent of sibling:sibling co-cultures (FIGS. 3(E) & 3(F)). Moreover, combining ECM extract from siblings and plxnd1 mutants produced intermediate morphologies dependent on the proportion of wild-type sibling:plxnd1 mutant ECM (FIGS. 14(B) & 14(C)), suggesting that the capacity of plxnd1 mutant ECM to induce proliferation and hyperplastic morphology is proportional to the amount of plxnd1 mutant ECM present. Injection of col5a1 vMO prior to ECM extraction abrogated the ability of plxnd1 mutant ECM to induce proliferation and hyperplastic morphology in cultured plxnd1 mutant SVCs (FIGS. 14(D) & 14(F)). These data demonstrate that plxnd1 mutant ECM is sufficient to induce hyperproliferation of SVCs and a smaller overall size of LDs.

Example 4: Regional Lipid Deposition is Controlled by Plxnd1

Lipid is Preferentially Deposited in SAT of Plxnd1 Mutants Fed a High-Fat Diet

Daily immersion in 5% chicken egg yolk over the course of 2-3 weeks is used as a high-fat dietary supplement (HFD) to induce lipid accumulation and metabolism in zebrafish (Semova I., et al. (2012), Cell host & microbe 12(3):277-288; Walters J W, et al. (2012), Chemistry & biology 19(7):913-925; Carten J D, et al. (2011), Developmental biology 360(2):276-285; Marza E, et al. (2005), Developmental dynamics 232(2):506-518.)

Zebrafish were subjected to daily exposures of 5% chicken egg yolk over the course of 14-21 days. Wild-type Ekkwill, plxnd1 heterozygotes or plxnd1 homozygous mutant zebrafish were raised under normal conditions until 30 days post-fertilization (dpf), then ~10 size matched fish were transferred to 'nursery' mesh bottom tubes (Aquatic Habitats, #RC33A) suspended within a regular 10 L tank on the main recirculating system. Use of nursery tubes allows the segregation of experimental groups whilst maintaining identical environmental exposures and improved water conditions afforded by a recirculating aquatic system. Whilst contained within the nursery tubes, fish were fed a normal diet (see above) with the following supplement: on a daily basis, nursery tubes were moved to tanks containing either 5% (% v/v) chicken egg yolk in system water (high-fat diet; HFD) (Latta's Egg Ranch, Hillsborough, N.C.) or system water (control diet). Nursery tubes were incubated in their respective dietary regimen for ~2-4 hours daily, before being rinsed with system water and placed back in the original 10 L tank where they continued to receive normal diet. These daily supplements were continued for between 14 and 21 days.

Figure 4A:
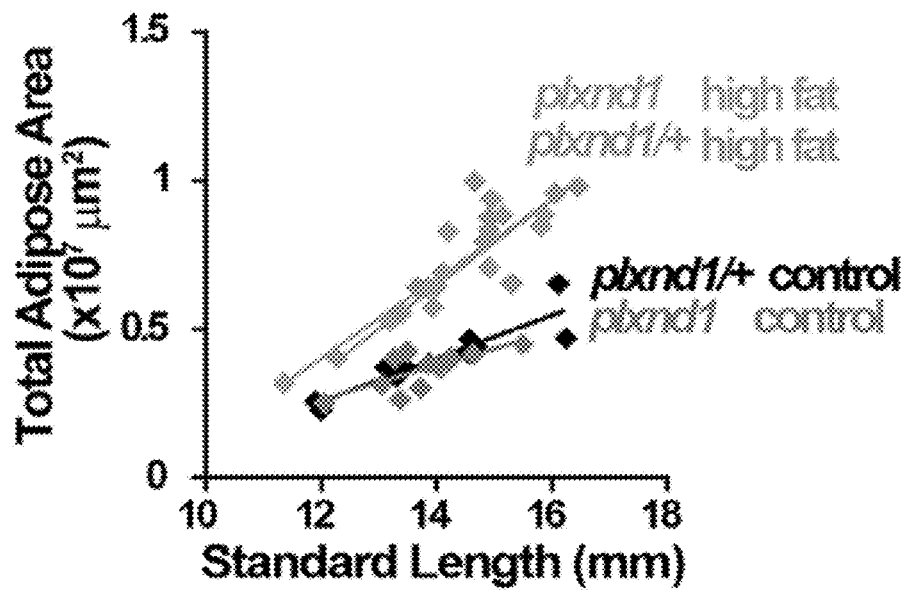
FIG. 4(A) shows quantitated total adipose area (Nile Red stained) relative to standard length after 14 days of normal or high-fat diet (HFD). Groups were either plxnd1 homozygous mutants (plxnd1) or plxnd1 heterozygotes (plxnd1/+). Left panels indicate whole animal body fat distribution, with areas enlarged on the right denoted by boxes. Experimental groups are: plxnd1/+ fed control diet (top row); plxnd1/+ fed high-fat diet (second row); plxnd1 fed control diet (third row); plxnd1 fed high fat diet (bottom row). Results show greater lipid storage and deposition after HFD intervention.
Figure 4B:
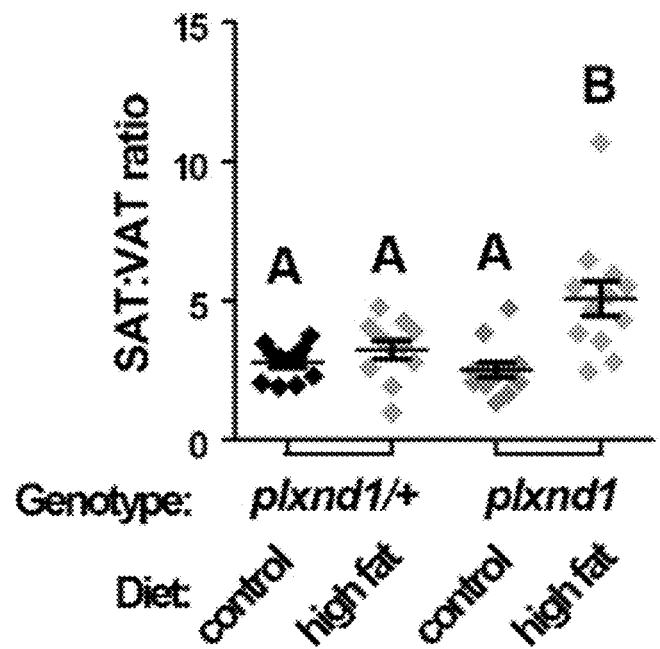
FIG. 4(B) shows plxnd1 mutants fed a HFD had a greater VAT:SAT ratio indicating disproportionate lipid storage in SAT.
Figure 15A:
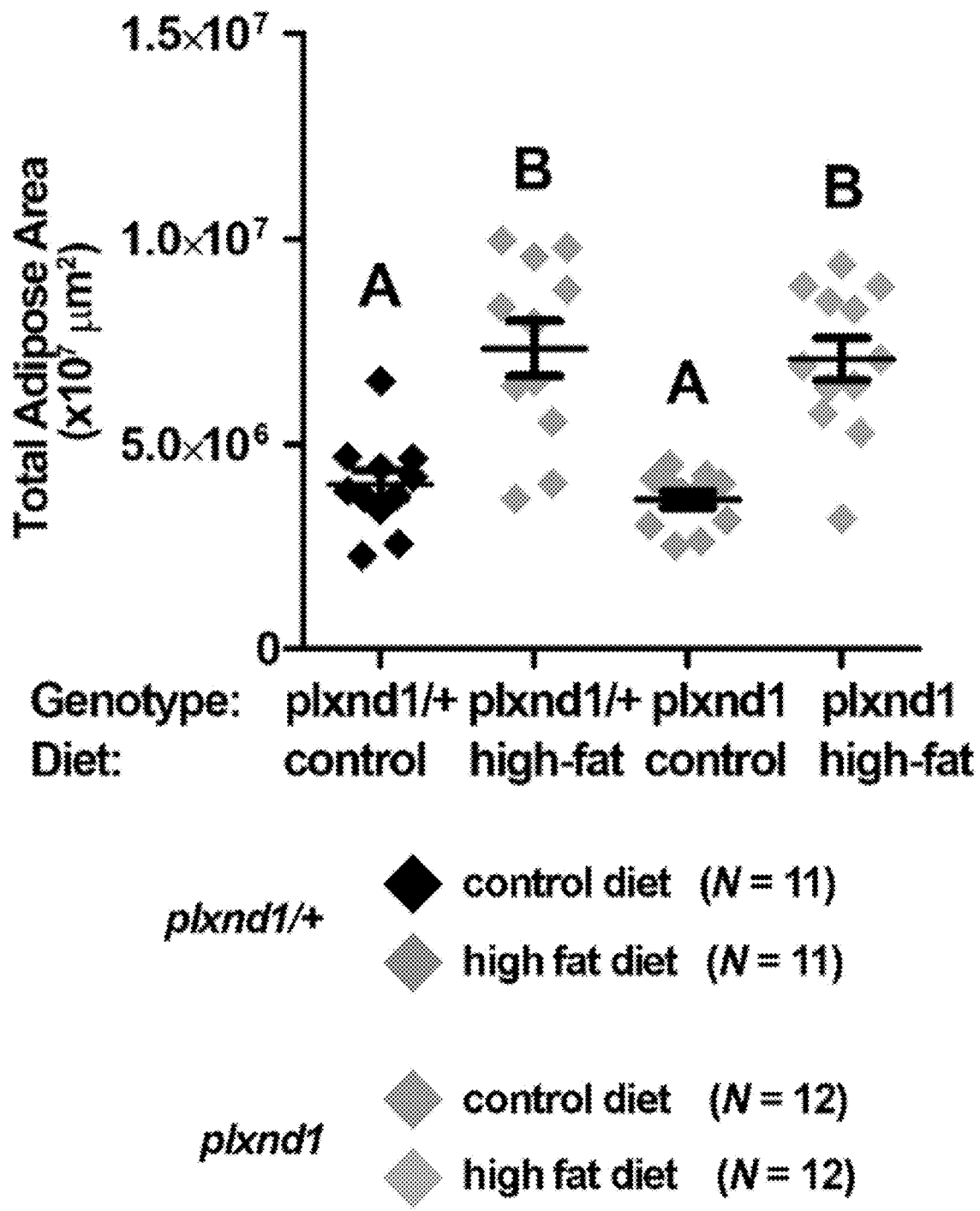
FIG. 15(A) shows quantification of total adipose area in plxnd1 homozygotes and plxnd1/+ heterozygotes fed either a control or high-fat diet.
Figure 15B:
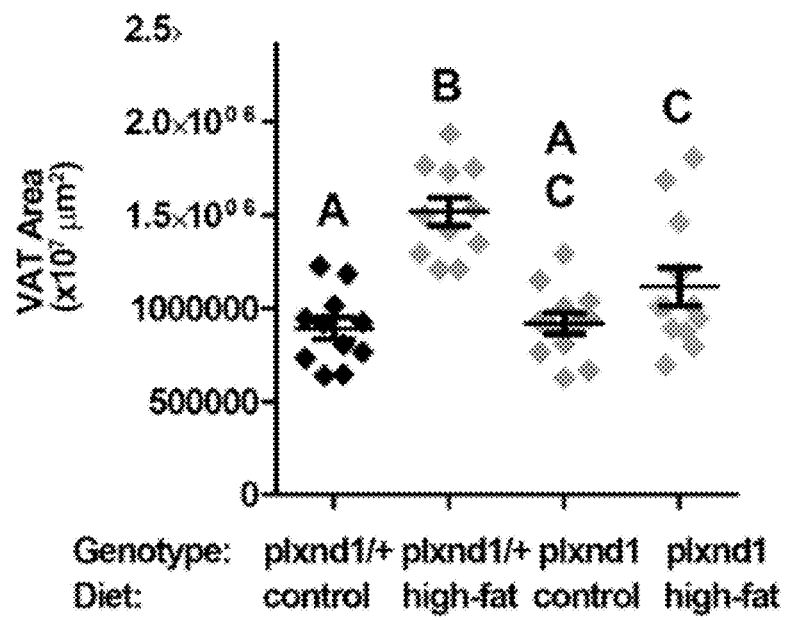
FIG. 15(B) shows quantification of VAT area in plxnd1 homozygotes and plxnd1/+ heterozygotes fed either a control or high-fat diet.
Figure 15C:
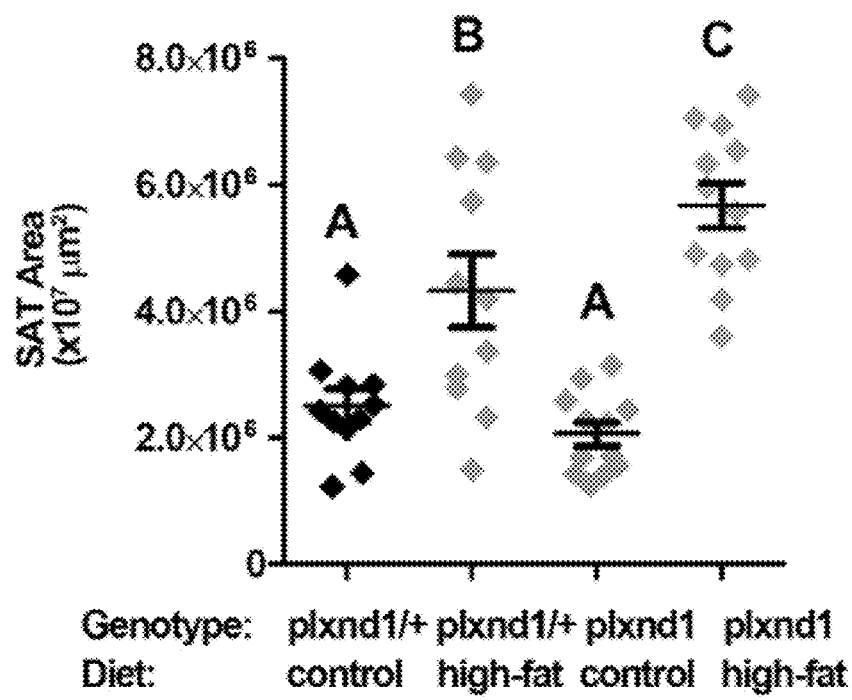
FIG. 15(C) shows quantification of SAT area in plxnd1 homozygotes and plxnd1/+ heterozygotes fed either a control or high-fat diet.

HFD treatment led to equivalent increases in lipid accumulation in both plxnd1/+ heterozygotes and homozygous plxnd1 mutants (FIG. 4(A), FIG. 15(A)). A substantial increase in total VAT and SAT area (FIGS. 15(B) & 15(C)) and VAT and SAT LD size was observed in heterozygotes (FIGS. 4(C) & 4(D)). However, VAT in HFD fed plxnd1 mutants did not expand (FIG. 15(B)), and VAT-LDs did not substantially increase in size (FIGS. 4(C) & 4(D)) plxnd1 mutants underwent a larger expansion of SAT when compared to heterozygotes (FIG. 15(C)), leading to supersized SAT-LDs (FIG. 4(D)) and an decreased VAT:SAT ratio (FIG. 4(B)). Together these data show that absence of Plxnd1 results in a preferential expansion of SAT in response to HFD, and thus leads to further exacerbation of altered body fat distribution.

Plxnd1 Deficiency Protects Zebrafish from High-Fat Diet Induced Insulin Resistance Glucose assessment and glucose tolerance test (GTT). Adult zebrafish were weighed as described. (Eames S C, et al. (2010), Zebrafish 7(2):205-213.) 1 mg/g glucose (fish weight) was injected intra-abdominally. 5 µl of blood was collected by cardiac puncture, and glucose levels assessed using the FreeStyle Lite monitor (Abbot Diabetes Care Inc) as described. (Eames S C, et al. (2010), Zebrafish 7(2):205-213.) For basal blood glucose assessments, zebrafish were fasted for 4 h prior to blood collection.

Figure 5A:
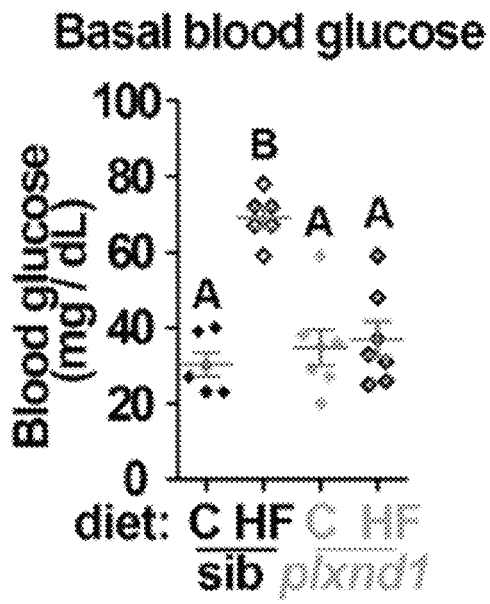
FIG. 5(A) shows basal blood glucose measurements revealing that wild-type siblings fed a high-fat (HF) diet are hyperglycaemic compared to controls.
Figure 5B:
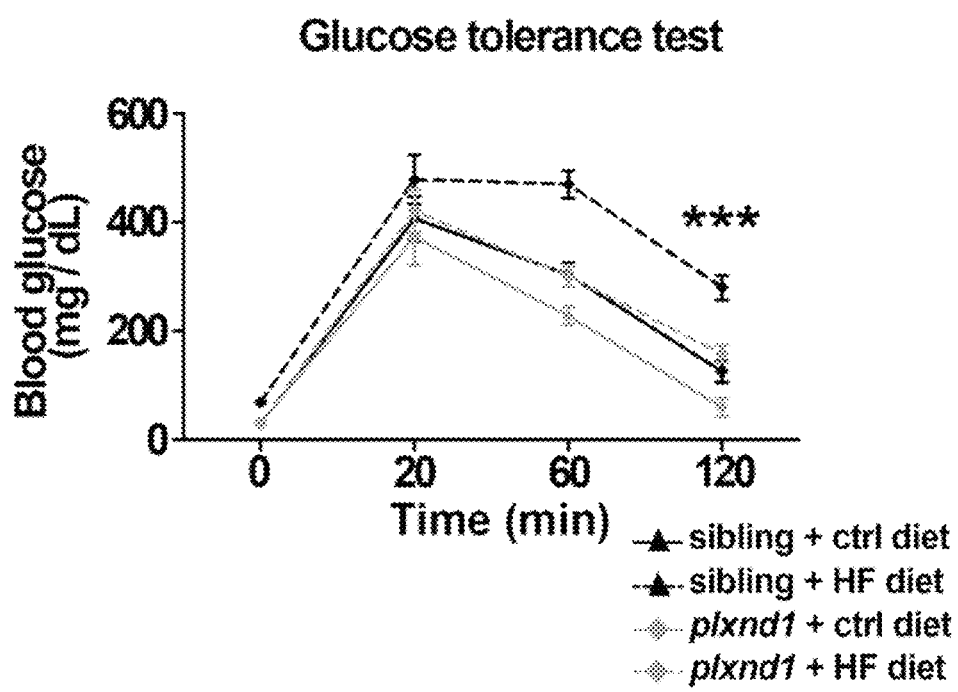
FIG. 5(B) shows glucose tolerance tests that reveal wild-type siblings fed a high-fat (HF) diet have a decreased capacity to normalize blood glucose relative to control fed siblings (P<0.001). plxnd1 mutants fed a control diet have an enhanced capacity to normalize blood glucose relative to control fed siblings (P<0.01); whereas, plxnd1 mutants fed a HF diet have equivalent capacity to normalize experimentally-induced hyperglycemia to control fed siblings (P>0.05). One factor ANOVA followed by Tukey's HSD test (a=0.05) was used to determine statistical significance at 120 min.
Figure 5C:
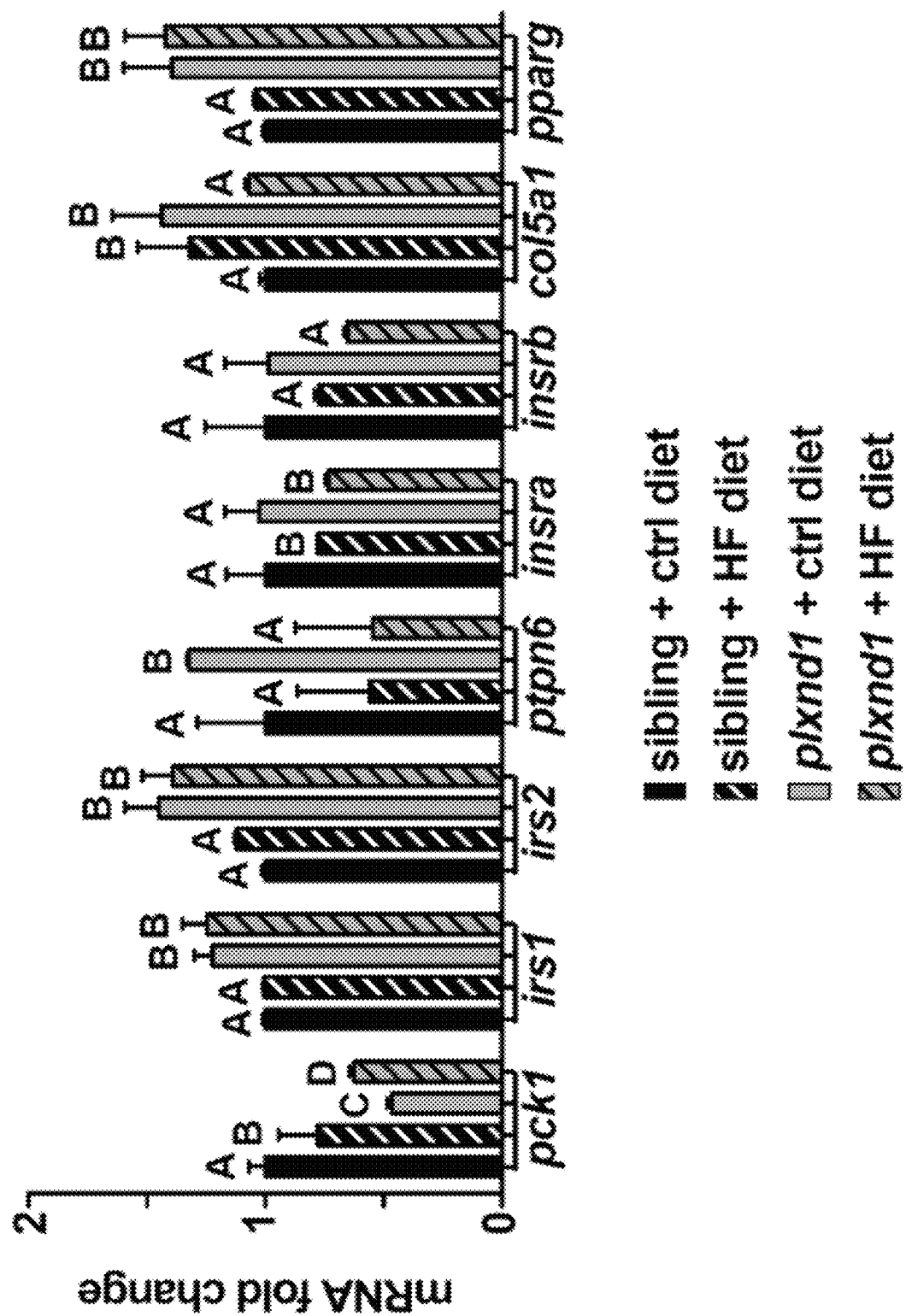
FIG. 5(C) shows qRT-PCR analysis of markers of insulin signalling and metabolism in zebrafish VAT.

HFD-fed wild-type siblings had hyperglycaemia (FIG. 5(A)). Further, after a glucose tolerance test (GTT) siblings fed a HFD failed to normalize blood glucose levels, suggesting a degree of systemic insulin resistance (FIG. 5(B)). By contrast, plxnd1 mutants fed a HFD did not exhibit hyperglycaemia (FIG. 5(A)) and efficiently normalized hyperglycemia after a GTT (FIG. 5(B). The insulin receptor substrates 1 and 2 (irs1, irs2) are negatively regulated in insulin resistance. (Capiotti K M, et al. (2014), Comparative biochemistry and physiology. Part B, Biochemistry & molecular biology 171:58-65; Goodyear L J, et al. (1995), The Journal of clinical investigation 95(5):2195-2204; Ruiz-Alcaraz A J, et al. (2005), The Biochemical journal 392(Pt 2):345-352.) However, in both control and HFD fed plxnd1 VAT, irs1 and irs2 mRNAs were increased compared to siblings supporting augmented insulin signalling in plxnd1 mutants (FIG. 5(C)).

Example 5: Increased PLXND1 mRNA in Human VAT is Associated with Type 2 Diabetes Correlation between PLXND1 expression and adipocyte insulin sensitivity (FIG. 16) was examined in another cohort of 56 individuals comprising 30 obese (BMI>30 kg/m$^2$) otherwise healthy and 26 non-obese (BMI<30 kg/m$^2$) healthy women. (Arner E, et al. (2012), Diabetes 61(8): 1986-1993.) All were pre-menopausal and free of continuous medication. An abdominal SAT biopsy was obtained by needle aspiration. Adipocyte in vitro insulin sensitivity was determined by quantifying the uptake of glucose into lipids in response to insulin as previously described. (Dahlman I, et al. (2004) alpha2-Heremans-Schmid glycoprotein gene polymorphisms are associated with adipocyte insulin action. Diabetologia 47(11):1974-1979.) Microarray analysis was performed exactly as described on fractionated abdominal SAT adipocytes (Arner E, et al. (2012), Diabetes 61(8).1986-1993) using the Affymetrix GeneChip mRNA Array protocol. Gene expression results are accessible at GEO (accession number GSE25402). Multiple regression analysis was performed to assess correlation of PLXND1 and insulin sensitivity, adjusting for age and BMI.

Figure 5D:
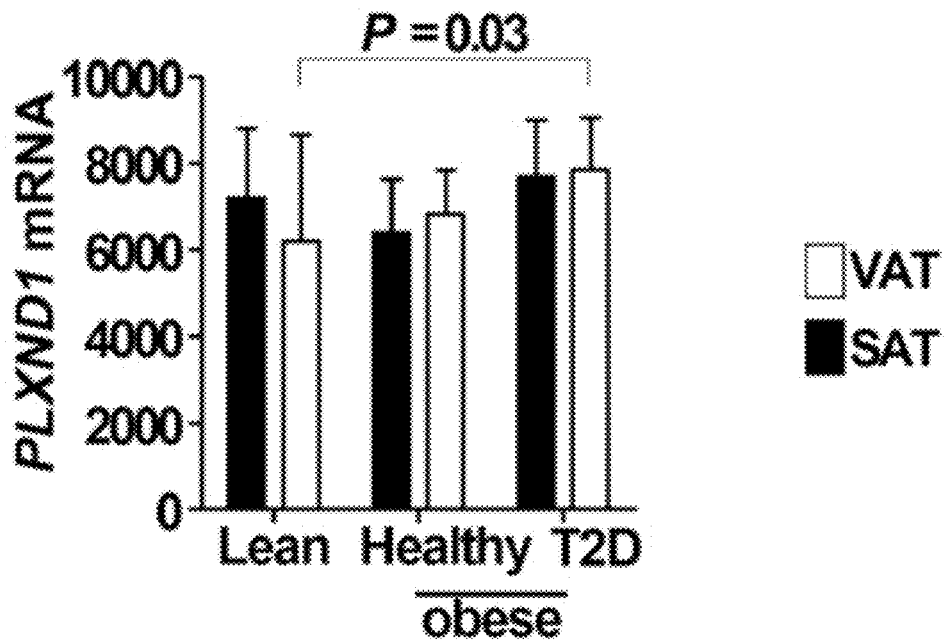
FIG. 5(D) shows human PLXND1 mRNA is significantly upregulated in VAT, but not SAT, of obese patients with type 2 diabetes.
Figure 5E:
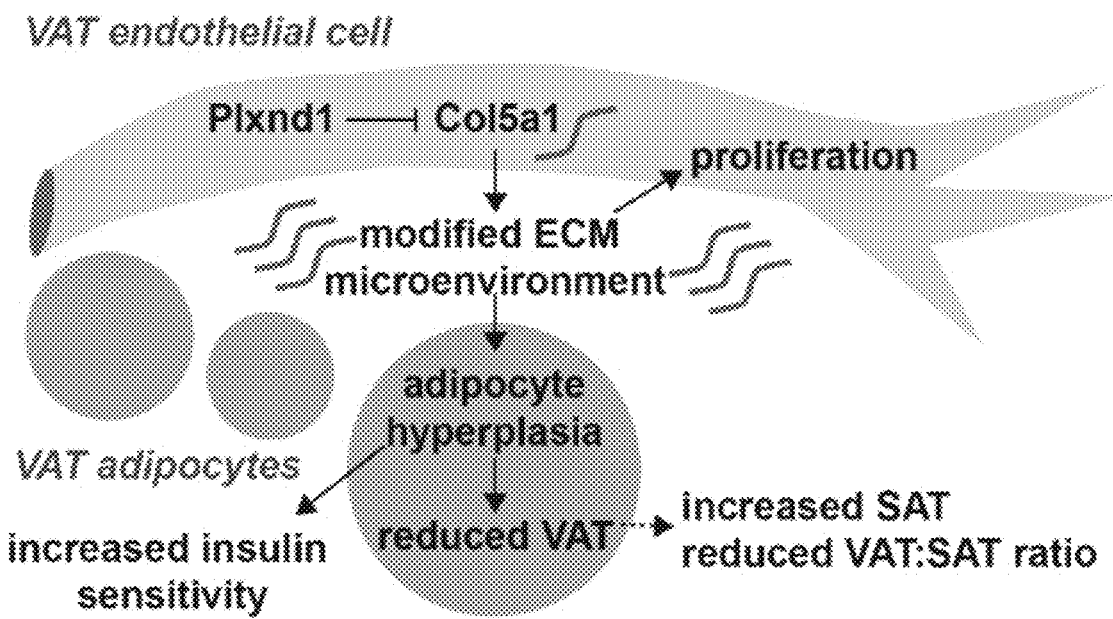
FIG. 5(E) shows schematic illustrating the current working model of Plxnd1-mediated regulation of VAT morphology.
Figure 16B:
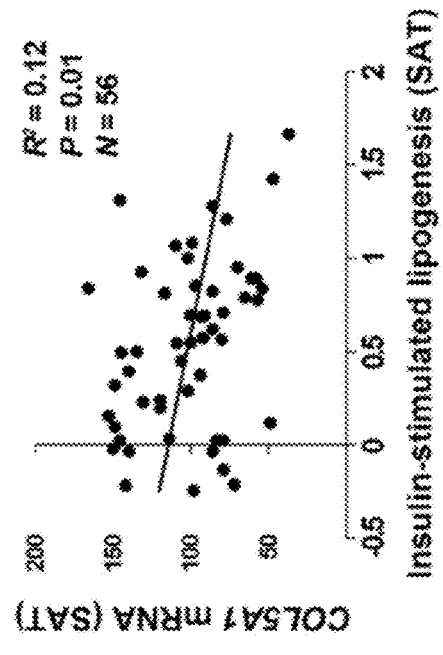
FIG. 16(B) shows SAT COL5A1 mRNA is inversely associated with insulin-stimulated lipogenesis in SAT adipocytes.
Figure 16A:
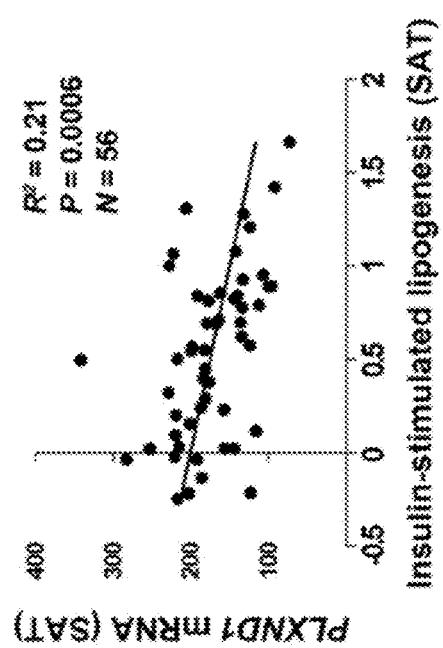
FIG. 16(A) shows SAT PLXND1 mRNA is inversely associated with insulin-stimulated lipogenesis in SAT adipocytes.
Figure 16D:
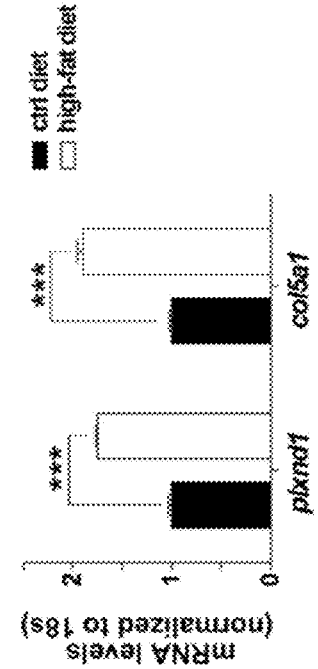
FIG. 16(D) shows qRT-PCR reveals plxnd1 and col5a1 mRNAs are increased after feeding zebrafish a HFD for 14 days.
Figure 16C:
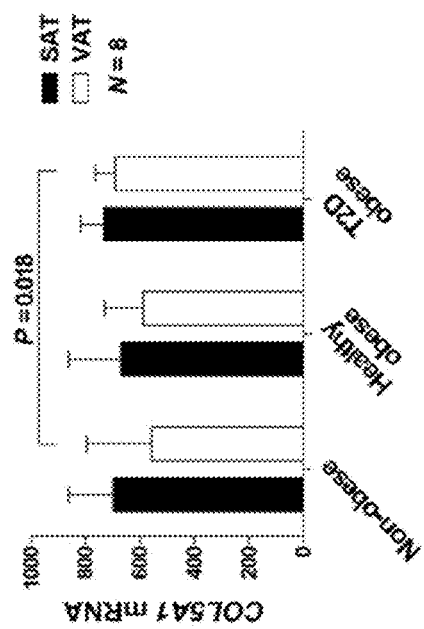
FIG. 16(C) shows COL5A1 mRNA is significantly upregulated in VAT, but not SAT, of obese patients with type 2 diabetes.
Figure 17:
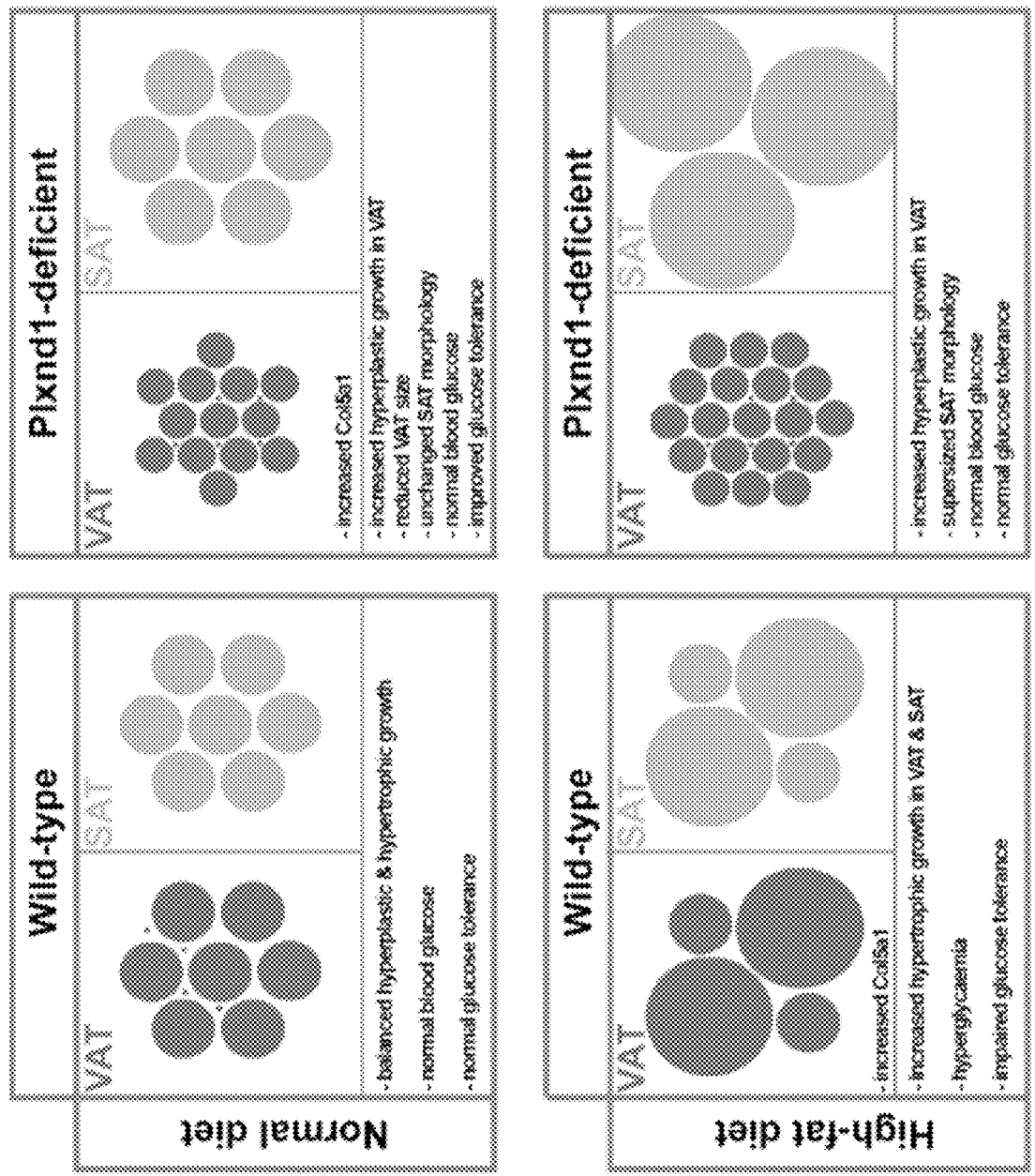
FIG. 17 shows a schematic model depicting VAT and SAT dynamics after Plxnd1 manipulation.

PLXND1 mRNA levels in VAT and SAT from lean (N=8), healthy obese (N=8), and type 2 diabetic obese (T2D, N=8) patients were quantified by microarray (FIG. 5(D) and 16(C)) exactly as described. (Dahlman I, et al. (2006), Diabetes 55(6):1792-1799.) Groups were compared by Student's t-test. Values are mean±SD.

PLXND1 mRNA was specifically increased in VAT of obese patients with type 2 diabetes (FIG. 5(D)). No change was observed in SAT (FIG. 5(D)) or in AT of healthy obese patients (FIG. 5(D)).

The invention claimed is:

1. A method of identifying a subject at risk for metabolic dysfunction, the method comprising:
 (a) isolating a biosample from a subject;
 (b) determining the level of one or more biomarkers present in the biosample, wherein the one or more biomarkers comprise
  PlexinD1 nucleic acid or protein,
  COL5A1 nucleic acid or protein, or
  a combination thereof;
 (c) identifying the subject as having a risk for metabolic dysfunction when the level of the one or more biomarkers is increased or decreased relative to a reference level or a range of reference levels of the same biomarker, and wherein the metabolic dysfunction is insulin sensitivity, insulin resistance, or type 2 diabetes; and
 (d) treating the at-risk subject by administering to the subject an interfering molecule that (i) decreases the level or activity of the PlexinD1 nucleic acid or protein, or (ii) increases the level or activity of the COL5A1 nucleic acid or protein.

2. The method of claim 1, wherein determining the level of the one or more biomarkers comprises determining the level of at least two biomarkers.

3. The method of claim 1, further comprising determining the level of at least two of visceral adipose tissue, subcutaneous adipose tissue, hypertrophic visceral adipose tissue, and hyperplastic visceral adipose tissue, and generating a ratio of the level of the at least two adipose tissues.

4. The method of claim 3, wherein the ratio of the level of the at least two biomarkers comprises the level of visceral adipose tissue and the level of subcutaneous adipose tissue.

5. The method of claim 1, wherein the metabolic dysfunction is insulin sensitivity.

6. The method of claim 1, wherein the metabolic dysfunction is insulin resistance.

7. The method of claim 1, wherein the metabolic dysfunction is type 2 diabetes.

8. The method of claim 1, wherein the biosample comprises a biopsy material, adipose tissue, bone marrow, blood, blood plasma, serum or a cellular fraction thereof, urine, feces, saliva, tears, or cells derived from a biological source.

9. The method of claim 1, wherein determining the level of the one or more biomarkers comprises using PCR, RT-PCR, ELISA, immunolabeling, in situ hybridization, or nucleic acid sequencing.

10. The method of claim 1, wherein the interfering molecule comprises a small molecule, an antibody, an antisense RNA, a cDNA, or a dominant-negative form of a molecule.

11. The method of claim 1, wherein the interfering molecule increases the level or activity of the COL5A1 nucleic acid or protein.

12. The method of claim 1, wherein the interfering molecule decreases the level or activity of the PlexinD1 nucleic acid or protein.

* * * * *